US008367325B2

(12) United States Patent
Wangh et al.

(10) Patent No.: US 8,367,325 B2
(45) Date of Patent: Feb. 5, 2013

(54) LATE-PCR

(75) Inventors: Lawrence J. Wangh, Auburndale, MA (US); Kenneth Pierce, Natick, MA (US); Cristina Hartshorn, Needham, MA (US); John Rice, Quincy, MA (US); J. Aquiles Sanchez, Framingham, MA (US)

(73) Assignee: Brandeis University, Waltham, MA (US)

( * ) Notice: Subject to any disclaimer, the term of this patent is extended or adjusted under 35 U.S.C. 154(b) by 1339 days.

(21) Appl. No.: 11/701,428

(22) Filed: Feb. 2, 2007

(65) Prior Publication Data

US 2008/0280292 A1 Nov. 13, 2008

Related U.S. Application Data

(62) Division of application No. 10/320,893, filed on Dec. 17, 2002, now Pat. No. 7,198,897.

(60) Provisional application No. 60/341,886, filed on Dec. 19, 2001.

(51) Int. Cl.
*C12Q 1/68* (2006.01)
*C12P 19/34* (2006.01)
(52) U.S. Cl. .................... 435/6.1; 435/91.2; 536/23.1
(58) Field of Classification Search .................... None
See application file for complete search history.

(56) References Cited

U.S. PATENT DOCUMENTS

| | | | |
|---|---|---|---|
| 4,965,188 | A | 10/1990 | Mullis et al. |
| 5,066,584 | A | 11/1991 | Gyllensten et al. |
| 5,210,015 | A | 5/1993 | Gelfand et al. |
| 5,538,848 | A | 7/1996 | Livak et al. |
| 5,627,054 | A | 5/1997 | Gillespie |
| 5,849,497 | A | 12/1998 | Steinman |
| 5,925,517 | A | 7/1999 | Tyagi et al. |
| 5,994,056 | A | 11/1999 | Higuchi |
| 6,365,729 | B1 | 4/2002 | Tyagi et al. |
| 6,887,664 | B2 * | 5/2005 | Chen et al. .................... 435/6 |

FOREIGN PATENT DOCUMENTS

| | | |
|---|---|---|
| WO | WO 98/59072 | 12/1998 |
| WO | WO 01/94638 | 12/2001 |

OTHER PUBLICATIONS

Vogelstein et al. (PNAS, 1999, vol. 96, p. 9236-9241, IDS reference).*
Sanchez, J. Aquiles et al., "Linear-After-The-Exponential (LATE)—PCR: An advanced method of asymmetric PCR and its uses in quantitative real-time analysis"; Proceedings of the National Academy of Sciences of USA (PNAS), Feb. 17, 2004, vol. 101, No. 7, pp. 1933-1938, XP002397153.
Search Report dated Jul. 21, 2008 from counterpart European application No. 07075653.1(7 pgs.).

Afonina, IA, et al. Minor Groove Binder-Conjugated DNA Probes for Quantitative DNA Detection by Hybridization-Triggered Fluorescence. *BioTechniques* 32: 940-949. (Apr. 2002).
Alexandersen, S. et al. Development of reverse transcription-PCR (oligonucleotide probing) enzyme-linked immunosorbent assays for diagnosis and preliminary typing of foot-and-mouth disease: a new system using simple and aqueous-phase hybridization. *Journal of Clinical Microbiology* 38: 4604-4613 (2000).
Allard, MW. et al. The production of single-stranded DNA suitable for sequencing using the polymerase chain reaction. *BioTechniques* 10: 24-26 (1991).
Allawi, Hatim et al. Thermodynamics and NMR of Interal GT Mismatches in DNA. *Biochemistry* 36: 10581-10594 (1997).
AN, HS. et al. Isolation of 88F actin mutants of *Drosophila melanogaster* and possible alterations in the mutant actin structures. *J. Mol. Biol* 260: 492-505. (1996).
Balaguer, P. et al. Quantification of DNA sequences obtained by polymerase chain reaction using a bioluminescent adsorbent. *Analytical Biochemistry* 195: 105-110. (1991).
Balauger, P. et al. "Quantification of DNA sequence obtained by polymerase chain reaction using a bioluminescent adsorbent," Analytical Biochemistry, 1991, vol. 195, p. 105-110.
Barratt, K. et al. Improving Real-Time PCR Genotyping Assays by Asymmetric Amplification. *J. Clin. Microbial* 40: 1571-1572 (2002).
Bell, DA. et al. DNA sequence analysis of revertants of the hisD3052 allele of *Salmonella typhimurium* TA98 using the polymerase chain reaction and direct sequencing: application to 1-nitropyrene-induced revertants. *Mutation Research* 252: 35-44 (1991).
Bianchi, N. et al. Biosensor technology and surface plasmon resonance for real-time detection of HIV-1 genomic sequences amplified by polymerase chain reaction. *Clinical and Diagnostic Virology* 8: 199-208 (1997).
Bianchi, N. et al. Capillary electrophoresis: detection of hybridization between synthetic oligonucleotides and HIV-1 genomic DNA amplified by polymerase-chain reaction. *Journal of Virological Methods* 47: 321-329 (1994).
Bianchi, N. et al. Detection of hepatitis C virus by unbalanced polymerase-chain reaction, hybridization to synthetic oligonucleotides and capillary electrophoresis. *International Journal of Oncology* 4: 903-907 (1994).
Bianchi, N. et al. Polymerase-chain reaction: analysis of DNA/DNA hybridization by capillary electrophoresis. *Nucleic Acids Research* 21: 3595-3596. (1993).
Bonnet, S. et al. Efficient reamplification of differential display products by transient ligation and thermal asymmetric PCR. *Nucleic Acids Research* 26: 1130-1131 (1998).

(Continued)

*Primary Examiner* — Stephanie K Mummert
(74) *Attorney, Agent, or Firm* — Casimir Jones, S.C.

(57) ABSTRACT

A non-symmetric polymerise chain reaction (PCR) amplification method employing a limiting primer in low concentration whose concentration-adjusted melting point at least equals, and preferably exceeds, that of the excess primer, the latter in turn not being more than 25° C. below the melting temperature of the amplicon. Assays employing such amplification and labeled hybridization probes, including assays that include a detection step following primer extension or a low-temperature probe, or both. Kits for performing such assays and primer or primer-and-probe sets for performing the foregoing amplifications and assays.

30 Claims, 18 Drawing Sheets

OTHER PUBLICATIONS

Boysen, M. et al. Identification at strain level of *Rhizoctonia solani* AG4 isolates by direct sequence of asymmetric PCR products of the ITS regions. *Curr Genet* 29: 174-181. (1996).

Breslauer, Kenneth J. et al. Predicting DNA duplex stability from the base sequence. *Proc. Natl. Acad. Sci.* USA 83: 3746-3750 (1986).

Burggraf, S. et al. Unexplained DNA Melting Behavior in a Genotyping Assay. *Clinical Chemistry* 48: 199-201 (2002).

Debenardi, S. et al. Introduction of magnetic beads in diagnosis: a simple and rapid method to detect mutations of beta globin gene, directly amplified from blood. *Boll. Chim Farmaceufico* 132: 478-480 (1993).

Dicker, A P. et al. Mutational analysis of human NRAS genes in malignant melanoma: rapid methods for oligonucleotide hybridization and manual and automated direct sequencing of products generated by the polymerase chain reaction. *Genes, Chromosomes & Cancer* 1: 257-269 (1990).

Ding, J. et al. Single-strand conformation polymorphism for analysis of genomic variability of hepatitis C virus nonstructure 5A region. *Chinese Medical Journal* (Engl) 111: 1114-1117 (1998).

Eggerding, F A. et al. Detection of rubella virus gene sequences by enzymatic amplification and direct sequencing of amplified DNA. *Journal of Clinical Microbiology* 29: 945-952 (1991).

Eick, S. et al. Sequence analysis of amplified t(14; 18) chromosomal breakpoints in B-cell lymphomas. *Journal of Pathology* 162: 127-133 (1990).

Feriotto, G. et al. Biosensor technology and surface plasmon resonance for real-time detection of genetically modified Roundup Ready soybean gene sequences. *J. Agric. Food Chem.* 50: 955-962 (2002).

Feriotto, G. et al. Biosensor technology for real-time detection of the cystic fibrosis W 1282X mutation in CFTR. *Human Mutation* 18: 70-81 (2001).

Feriotto, G. et al. Detection of the ΔF508 (F508del) mutation of the cystic fibrosis gene by surface plasmon resonance and biosensor technology. *Human Mutation* 13: 390-400 (1999).

Fujii, T. et al. Rapid detection of the gene of *Legionella pneumophila* using the fluorescence polarization with the asymmetric PCR. *Nucleic Acids Symposium Series* 42: 59-60 (1999).

Fujita, T. et al. Identification of DNA polymorphism by asymmetric-PCR SSCP. *BioTechniques* 19: 532-534 (1995).

Gandrille, S. et al. Identification of 15 different candidate causal point mutations and three polymorphisms in 19 patients with protein S deficiency using a scanning method for the analysis of the protein S active gene. *Blood* 85: 130-138. (1995).

Gandrille, S. et al. Molecular basis for hereditary antithrombin III quantitative deficiencies: a stop codon in exon IIIa and a frameshift in exon VI. *British Journal of Haematology* 78: 414-420. (1991).

Garcia-Quintanilla, A. et al. Single-tube balanced heminested PCR for detecting *Mycobacterium tuberculosis* in smear-negative samples. *Journal of Clinical Microbiology* 38: 1166-1169. (2000).

Gavilondo-Cowley, J V et al. Specific amplification of rearranged immunoglobulin variable region genes from mouse hybridoma cells. *Hybridoma* 9: 407-417. (1990).

Gilbertson, R L et al. Use of the asymmetric polymerase chain reaction and DNA sequencing to determine genetic variability of bean golden mosaic geminivirus in the Dominican Republic. *Journal of General Virology* 72: 2843-2848. (1991).

Glavac, D. et al. Optimization of the single-strand conformation polymorphism (SSCP) technique for detection of point mutations. *Human Mutation* 2: 404-414. (1993).

Gorski B, et al. LDL-R and Apo-B-100 gene mutations in Polish familial hypercholesterolemias. *Huma Genet* 102: 562-565. (1998).

Gyllensten, UB. PCR and DNA sequencing. *BioTechniques* 7: 700-708. (1998).

Gyllensten, UB. et al. Generation of single-stranded DNA by the polymerase chain reaction and its application to direct sequencing of the HLA-DQA locus. *Proc Natl Acad Sci USA* 85: 7652-7656. (1998).

Gyllensten, UB. et al. Sequencing of in vitro amplified DNA. *Methods in Enzymology* 218: 3-16. (1993).

Hamelin, R. et al. Efficient screening of p53 mutations by denaturing gradient gel electrophoresis in colorectal tumors. *Oncogene* 8: 2213-2220. (1993).

Hattori K. et al. Age-dependent increase in deleted mitochondrial DNA in the human heart: possible contributory factor to presbycardia. *American Heart Journal* 121: 1735-1742. (1991).

Hofmann, MA. et al. Sequencing PCR DNA amplified directly from a bacterial colony. *BioTechniques* 11:30-31. (1991).

Holzenberger, M. et al. Quantitation of tropoelastin mRNA and assessment of alternative splicing in human skin fibroblasts by reverse transcriptase-polymerase chain reaction. *PCR Methods and Applications* 3: 107-114. (1993).

Houge, G. Simplified construction of a subtracted cDNA library using asymmetric PCR. *PCR Method and Applications* 2: 204-209. (1993).

Igarashi, K. et al. Sequence analysis of the proximal promoter region of the human alpha-fetoprotein gene in hepatocellular carcinoma. *Cancer Letters* 76: 93-99. (1994).

Innis, MA, et al. DNA sequencing with *Thermus aquaticus* DNA polymerase and direct sequencing of polymerase chain reaction-amplified DNA. *Proc Natl Acad Sci USA* 85: 9436-9440. (1988).

Innis, MA. et al. Optimization of PCR's. *PCR Protocols: A Guide to Methods and Applications; Part One. Basic Methodology* pp. 3-12. (1990).

Jurinke, C. et al. Asymmetric polymerase chain reaction improves streptavidin-biotin based purification of polymerase chain reaction products prior to matrix-assisted laser desorption/ionization time-of-flight mass spectrometric analysis. *Rapid Communications in Mass Spectrometry* 12: 50-52. (1998).

Kai, E. et al. Detection of PCR products in solution using surface plasmon resonance. *Anal. Chem.* 71: 796-800. (1998).

Kai, E. et al. Purification of single stranded DNA from asymmetric PCR product using the SMART system. *Biotechnology Techniques* 12: 935-939 (1998).

Kang, JH. et al. Asymmetric polymerase chain reaction-single strand conformation polymorphism (asymmetric PCR-SSCP) as a simple method for allele typing of HLA-DRB. *Journal of Biochemistry and Molecular Biology* 32, 529-534. (1999).

Kido, C. et al. Rapid and simple detection of PCR product DNA: a comparison between Southern hybridization and fluorescence polarization analysis. *Gene* 259: 123-127. (2000).

Kinjo, M. Detection of asymmetric PCR products in homogeneous solution by fluorescence correlation spectroscopy. *BioTechniques* 25: 706-715. (1998).

Kiyama, M. et al. High-throughput asymmetric-PCR SSCP analysis using well-controlled temperature conditions. *BioTechniques* 21: 710-7116. (1996).

Kreitman, M. et al. A strategy for producing single-stranded DNA in the polymerase chain reaction. A direct method for genomic sequencing. *Gene Anal Techn* 6: 84-88 (1989).

Kropp, GL. et al. Asymmetrically primed selective amplification/temperature shift fluorescence polymerase chain reaction to detect the hemoglobin Constant Spring mutation. *Blood* 78: 26-29. (1991).

LaFlamme, N. et al. Mutation R96W in cytochrome P450c17 gene causes combined 17 alpha-hydroxylase/17-20-lyase deficiency in two French Canadian patients. *Journal of Clinical Endocrinology and Metabolism* 81: 264-268 (1996).

Landweber, LF. et al. Producing single-stranded DNA in polymerase chain reaction for direct genomic sequencing. *Methods in Enzymology* 218: 17-26. (1993).

Lay, MJ et al. Real-time fluorescence genotyping of factor V Leiden during rapid-cycle PCR. *Clinical Chemistry* 43: 2262-2267 (1997).

Le Novere, Nicolas. Melting, computing the melting temperature of nucleic acid duplex. *Bioinformatics Applications Note* 17: 1226-1227 (2001).

Lee, FK. et al. The R-type pyocin of *Pseudomonas aeruginosa* C is a bacteriophage tail-like particle that contains single-stranded DNA. *Infection and Immunity* 67: 717-725. (1999).

Li, Qingge et al. A new class of homogeneous nucleic acid probes based on specific displacement hybridization. *Nucleic Acids Research* 30: e5 (2002).

Loewy, ZG. et al. Enhancement of *Borrelia burgdorferi* PCR by uracil N-glycosylase. *Journal of Clinical Microbiology* 32: 135-138. (1994).

Logan, JM. et al. Rapid Identification of *Campylobacter* spp. By Melting Peak Analysis of Biprobes in Real-Time PCR. *Journal of Clinical Microbiology* 39: 2227-2232 (2001).

Lopez-Crapez E. et al. Rapid and large-scale method to detect K-ras gene mutations in tumor samples. *Clinical Chemistry* 43: 936-942. (1997).

Magome, H. et al. Single-strand conformation polymophism analysis of apple stem grooving capillovirus sequence variants. *Phytopathology* 89: 136-140 (1999).

Mao, H. et al. Synthesis of radioactive single-stranded DNA probes using asymmetrical PCR and oligonucleotide random priming. *BioTechniques* 27: 674-678. (1999).

Mason, IJ. Rapid and direct sequencing of DNA from bacteriophage plaques using sequential linear and asymmetric PCR. *BioTechniques* 12: 60, 62. (1992).

McCabe, PC. Production of single-stranded DNA by asymmetric PCR. In: PCR Protocols.. *A guide to methods and applications*, (Innis MA, Gelfand DH, Sninsky JJ, White TJ, eds.), pp. 76-83, Academic Press, NY. (1990).

Medori, R. et al. Production of single-stranded DNA for sequencing: an alternative approach. *BioTechniques* 12: 346-350. (1992).

Mgone, CS. et al. Detection of seven point mutations in the porphobilinogen deaminase gene in patients with acute intermittent porphyria, by direct sequencing of in vitro amplified cDNA. *Human Genetics* 90: 12-16. (1992).

Mgone, CS. et al. Identification of five novel mutations in the porphobilinogen deaminase gene. *Human Molecular Genetics* 3: 809-811. (1994).

Millican, DS. et al. A general method for single-stranded DNA probe generation. *Analytical Biochemistry* 249: 114-117. (1997).

Millican, DS. et al. Preparation of single-stranded antisense cDNA probes by asymmetric PCR. *Methods in Molecular Biology* 105: 337-350. (1998).

Millikan, R. et al. p53 mutations in benign breast tissue. *Journal of Clinical Oncology* 13: 2293-2300. (1995).

Millward, H. et al. Homogeneous Amplification and Mutation Scanning of the p53 Gene Using Fluorescent Melting Curves. *Clinical Chemistry* 48: 1321-1328 (2002).

Moller, A. et al. PCR-amplification of D2S44 alleles. *International Journal of Legal Medicine* 106: 294-297.(1994).

Mubumbila, MV. et al. Isolation by asymmetric polymerase chain reaction and partial sequencing of the common bean chloroplast trnL (UAA) gene and pseudogene. *Phytochemical Analysis* 4: 145-148. (1993).

Murakami, A. et al. Specific detection and quantitation of SCC antigen 1 and SCC antigen 2 mRNAs by fluorescence-based asymmetric semi-nested reverse transcription PCR. *TumorBiology* 21: 224-234. (2000).

Nichols, WC. et al. Direct sequencing of the gene for Maryland/German familial amyloidotic polyneuropathy type II and genotyping by allele-specific enzymatic amplification. *Genomics* 5: 535 540. (1989).

Nikitin, AY. et al. Early mutation of the neu (erbB-2) gene during ethylnitrosourea-induced oncogenesis in the rat Schwann cell lineage. *Proc. Natl Acad. Sci. USA* 88: 9939-9943. (1991).

Nolasco, G. et al. Asymmetric PCR ELISA: increased sensitivity and reduced costs for the detection of plant viruses. *European Journal of Plant Pathology* 108: 293-298. (2002).

Nurmi, J. et al. A new label technology for the detection of specific polymerase chain reaction products in a closed tube. *Nucleic Acids Research* 28: e28 i-vi. (2000).

Ohiso, I. et al. A fluorescence polarization assay using oligonucleotide probes for the rapid detection of verotoxin-producing *Escherichia coli*. *Journal of biotechnology* 81: 15-25. (2000).

Oroskar, AA. et al. Detection of immobilized amplicons by ELTSA-like techniques. *Clinical Chemistry* 42: 1547-1555. (1996).

Orru, D. et al. An improved protocol to generate high-efficiency single-stranded DNA probes by PCR. *BioTechniques* 14: 905-906. (1993).

Ota, Y. et al. Detection of platelet mitochondriai DNA deletions in Kearns-Sayre Syndrome. *Investigative Ophthalmology & Visual Science* 32: 2667-2675. (1991).

Oto, M. et al. Analysis of a polyadenine tract of the transforming growth factor-beta type II receptor gene in colorectal cancers by non-gel-sieving capillary electrophoresis. *Clinical Chemistry* 43: 759-763. (1997).

Owczarzy, Richard et al. Predicting Sequence-Dependent Melting Stability of Short Duplex DNA Oligomers. *Biopolymers* 44: 217-239 (1998).

Perrin, S. et al. Site-specific mutagenesis using asymmetric polymerase chain reaction and a single mutant primer. *Nucleic Acids Research* 18: 7433-7438. (1990).

Poddar, SK. Symmetric vs asymmetric PCR and molecular beacon probe in the detection of a target gene of adenovirus. *Molecular and Cellular Probes* 14: 25-32. (2000).

Rasmussen, SR. et al. Combined polymerase chain reaction-hybridization microplate assay used to detect bovine leukemia virus and *Salmonella*. *Clin Chem* 40: 200-205. (1994).

Reincke, M. et al. No evidence for oncogenic mutations in guanine nucleotide-binding proteins of human adrenocortical neoplasms. *Journal of Clinical Endocrinology and Metabolism* 77: 1419-1422. (1993).

Rheaume, E. et al. Congenital adrenal hyperplasia due to point mutations in the type II 3 beta-hydroxysteroid dehydrogenase gene. *Nature Genetics* 1: 239-245. (1992).

Santalucia, John Jr. A unified view of polymer, dumbbell, and oligonucleotide DNA nearest-neighbor thermodynamics. *Proc. Natl. Acad. Sci. USA* 95: 1460-1465 (1998).

Santalucia, John Jr. et al. Improved Nearest-Neighbor Parameters for Predicting DNA Duplex Stability. *Biochemistry* 35: 3555-3562 (1996).

Sawata, S. et al. Novel detection system of flow injection analysis (1). The existence of significant relation between secondary structure of DNA and sensitivity in signal detection. *Nucleic Acids Symposium Series* 37: 247-248 (1997).

Schuster, H. et al. Allele-specific and asymmetric polymerase chain reaction amplification in combination: a one step polymerase chain reaction protocol for rapid diagnosis of familial defective apolipoprotein B-100. *Analytical Biochemistry* 204: 22-25. (1992).

Scott, DL. et al. The differentiation of *Phytophthora* species that are pathogenic on potatoes by an asymmetric PCR combined with single-strand conformation polymorphism analysis. *Letters in Applied Microbiology* 27: 39-44. (1998).

Scully, SP. et al. The use of polymerase chain reaction generated nucleotide sequences as probes for hybridization. *Molecular and Cellular Probes* 4: 485-495. (1990).

Shayiq, RM. et al. Multiple in vitro site-directed mutagenesis using asymmetric polymerase chain reaction. *Analytical Biochemistry* 221: 206-208. (1994).

Shyamala, V. et al. Amplification of bacterial genomic DNA by the polymerase chain reaction and direct sequencing after asymmetric amplification: application to the study of periplasmic permeases. *Journal of Bacteriology* 171: 1602-1608. (1989).

Simard, J. et al. Molecular basis of congenital adrenal hyperplasia due to 3 beta-hydroxysteroid dehydrogenase deficiency. *Molecular Endocrinology* 7: 716-728. (1993).

Soh, J. et al. Hybrid selection of mRNA with biotinylated DNA. *Genetic Analysis, Techniques and Applications* 7:80-86. (1990).

Sugo, T. et al. Fibrinogen Niigata with impaired fibrin assembly: an inherited dysfibrinogen with a Bbeta Asn-160 to Set substitution associated with extra glycosylation at Bbeta Asn-158. *Blood* 94: 3806-3813.(1999).

Takagi, S. et al. Direct sequencing of PCR products using unlabeled primers, *BioTechniques* 14: 218-221. (1993).

Tavassoli, K. et al. Molecular diagnostics of 15 hemophilia A patients: characterization of eight novel mutations in the factor VII gene, two of which result in exon skipping. *Human Mutation* 12: 301-3. (1998).

Tavassoli, K. et al. Mutational analysis of ectopic factor VIII transcripts from hemophilia A patients: identification of cryptic splice site, exon skipping and novel point mutations. *Hum Genet* 100: 508-511. (1997).

Todd, AV. et al. DzyNA-PCR: use of DNAzymes to Detect and Quantify Nucleic Acid Sequences in a Real-Time Fluorescent Format. *Clinical Chemistry* 46: 625-630. (2000).

Tromp, G. et al. Sequencing of cDNA from 50 unrelated patients reveals that mutations in the triple helical domain of type II procollagen are an Infrequent cause of aortic aneurysms. *J. Clin Invest.* 91: 2539-2545. (1993).

Tsuruoka, M. et al. The extremely rapid oligonucleotide hybridization and high throughput detection of microbial gene sequences using fluorescence polarization. *Biosensors & Bioelectronics* 16: 695-699. (2001).

Van Kuppeveld, FJ. et al. Genus-and species-specific identification of mycoplasmas by 16S rRNA amplification. *Applied and Environmental Microbiology* 58: 2606-2615. (1992).

Vogelstein B, et al. "Digital PCR," PNAS, 1999, vol. 96, p. 9236-9241.

Wade, JA. et al. Combinatorial diversity in DR2 haplotypes. *Tissue Antigens* 41: 113-1 18. (1993).

Wang, H. et al. Label-free hybridization detection of a single nucleotide mismatch by immobilization of molecular beacons on an agarose film. *Nucleic Acids Research* 30: e61. (2002).

Wetmur, James G. DNA Probes: Applications of the Principles of Nucleic Acid Hybridization. *Critical Reviews in Biochemistry and Molecular Biology* 36: 227-259 (1991).

Wilson, RK. et al. Optimization of asymmetric polymerase chain reaction for rapid fluorescent DNA sequencing. *BioTechniques* 8: 184-189. (1990).

Wong, DM. et al. Branch capture reactions: displacers derived from asymmetric PCR. *Nucleic Acids Research* 19: 2251-2259. (1991).

Wooddell, CI. et al. Use of asymmetric PCR to generate long primers and single-stranded DNA for incorporating cross-linking analogs into specific sites in a DNA probe. *Genome Research* 6: 886-892. (1996).

Yamanaka, K. et al. T-cell receptor V beta selectivity in T-cell clones alloreactive to HLA-Dw14. *Human Immunology* 33: 57-64. (1992).

Ye, B-C. et al. Detection of *Escherichia coli* 015:H7 DNA using two fluorescence polarization methods. *Fresenius J Anal. Chem* 365: 452-457. (1999).

Zevin-Sonkin, D. et al. DENS (differential extension with nucleotide subsets): application to the sequencing of human genomic DNA and cDNA. *DNA Sequence* 10: 245-254. (1999).

Zuo, L. et al. A new mutation responsible for severe G6PD deficiency in two ethnic Chinese with different clinical presentations: determination by a direct PCR sequencing technique. *International Journal of Hematology* 55: 39-44. (1992).

\* cited by examiner

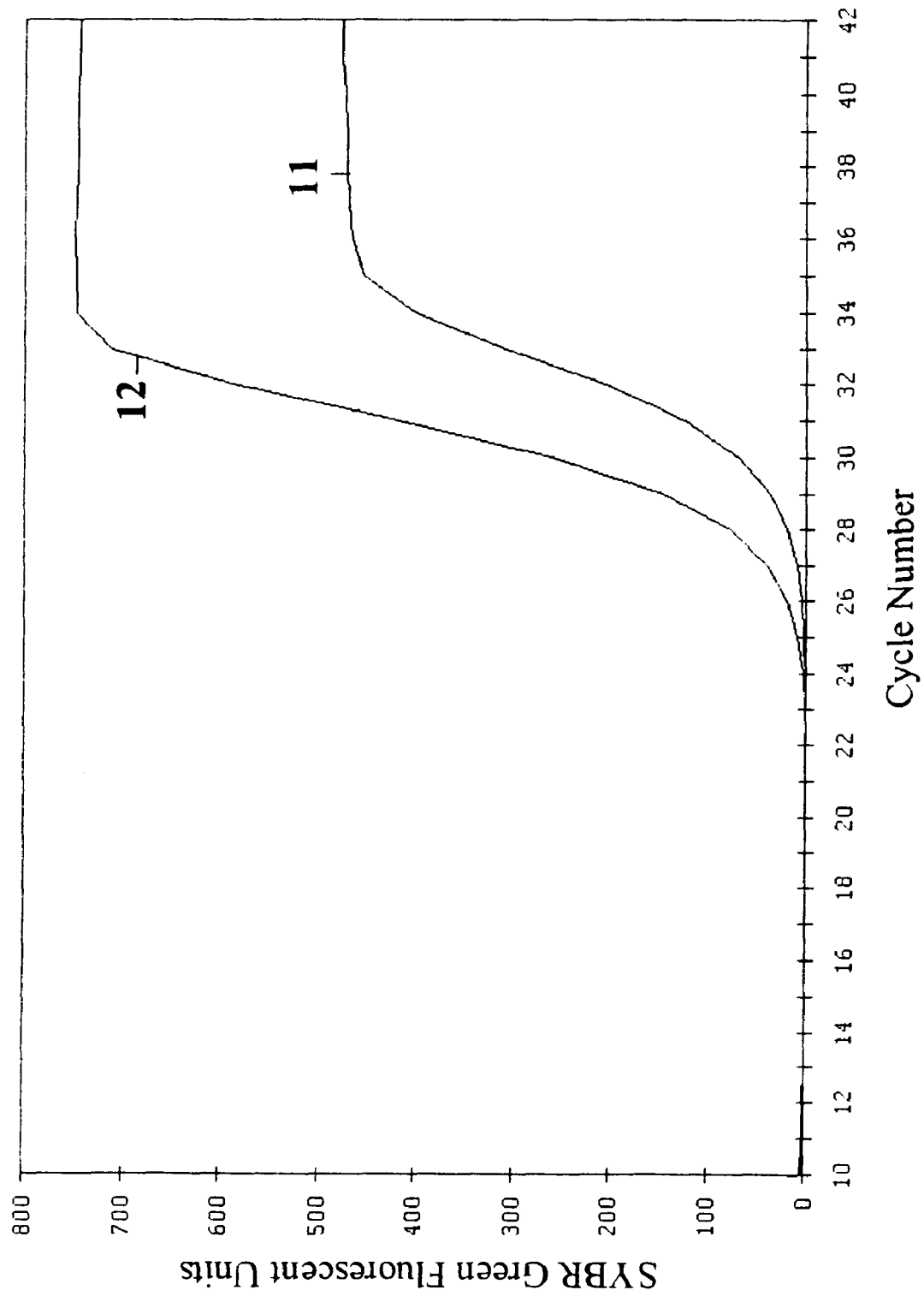

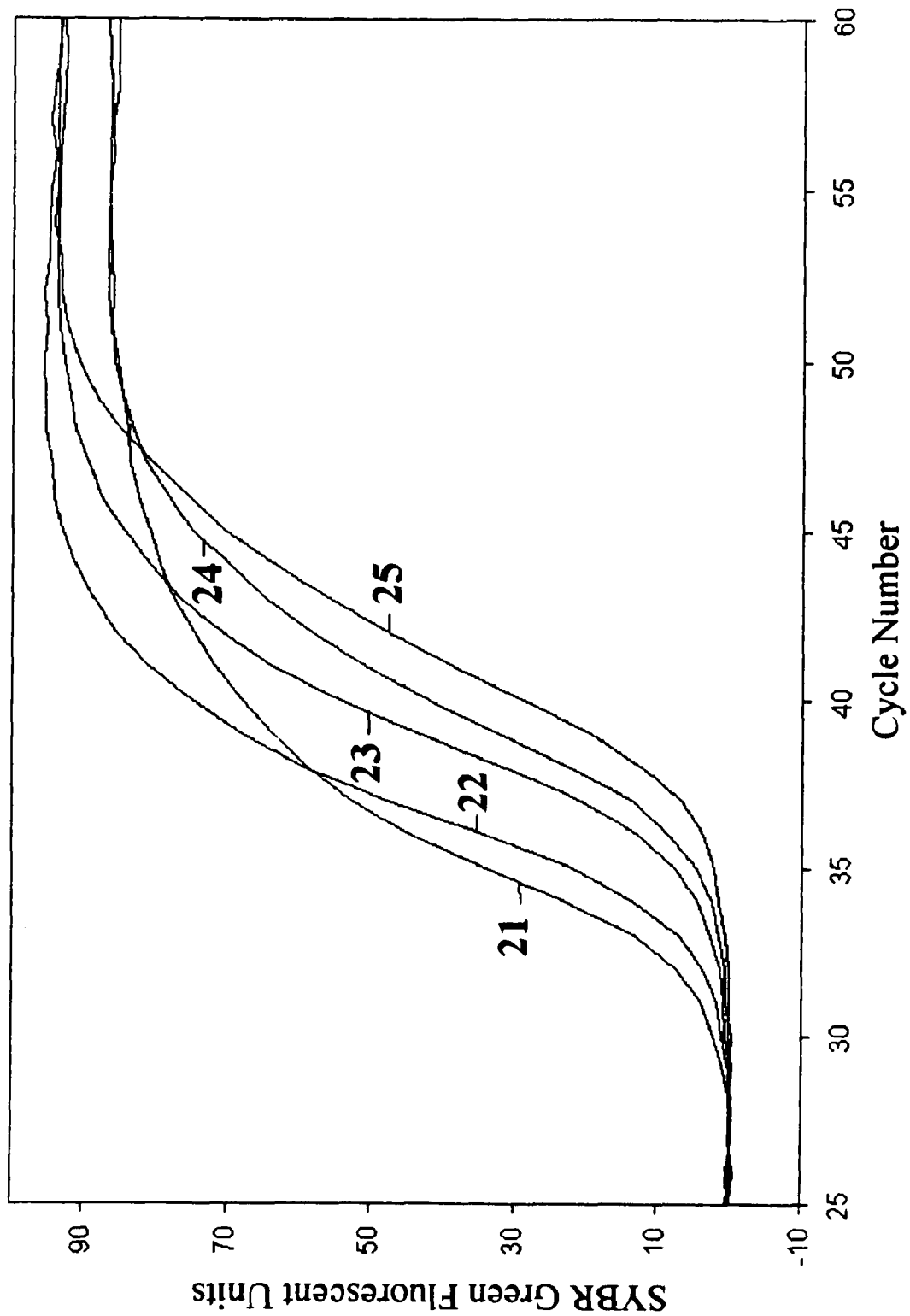

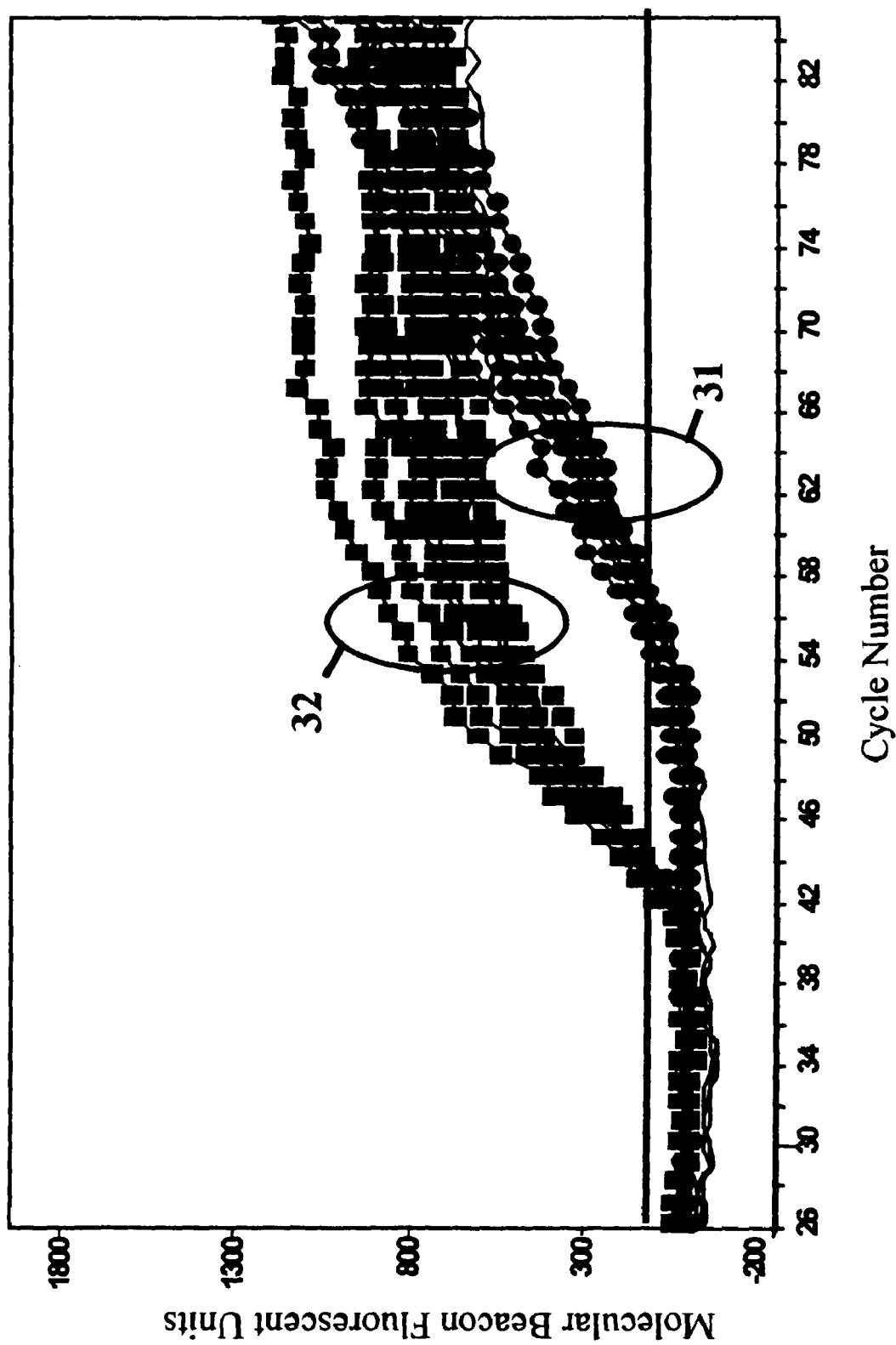

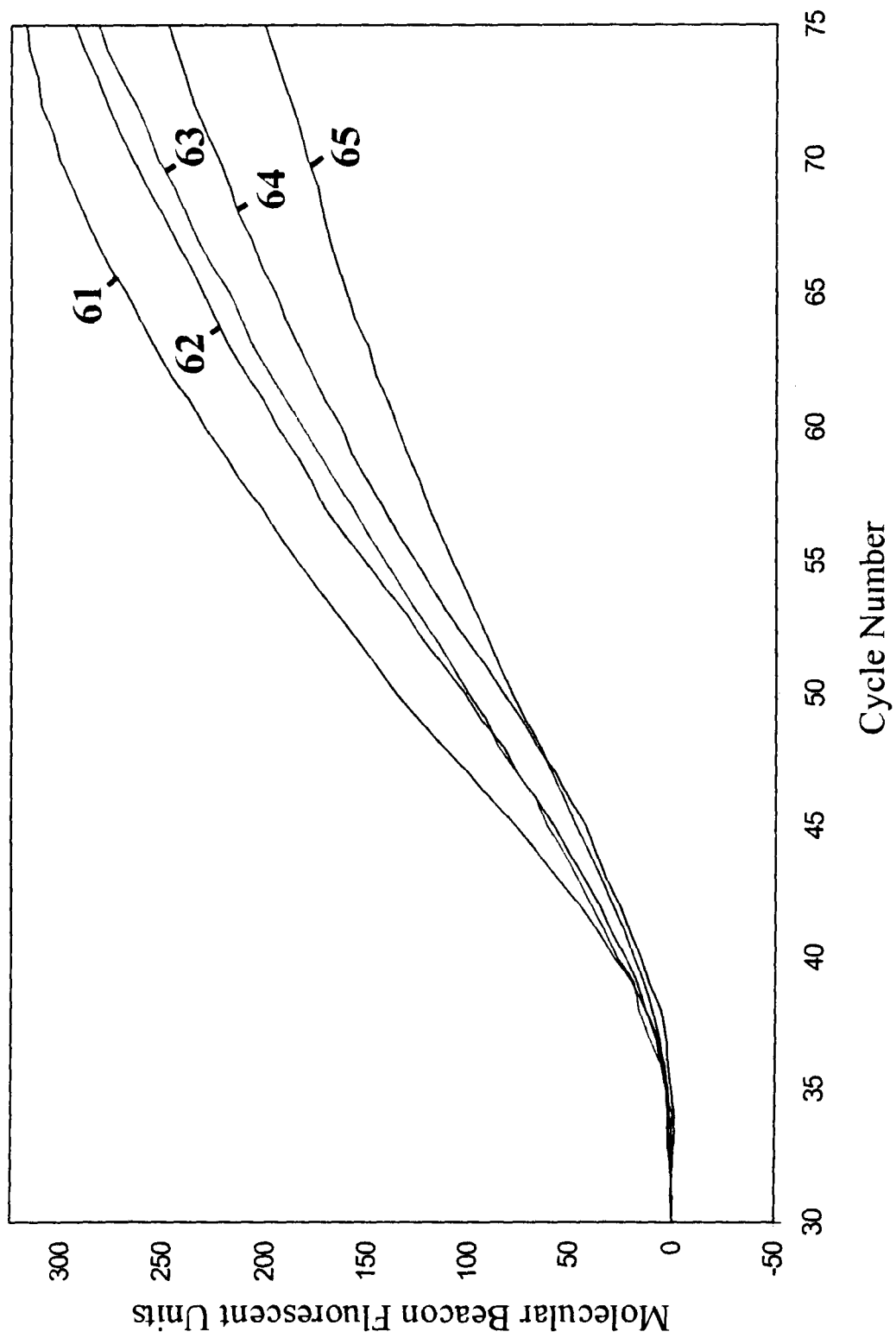

LATE-PCR

This application is a divisional application of U.S. application Ser. No. 10/320,893, filed Dec. 17, 2002, which claims the benefit of U.S. Provisional Application Ser. No. 60/341,886, filed Dec. 19, 2001, all of which are incorporated herein by reference.

TECHNICAL FIELD

This invention relates to amplification of nucleic acid sequences by methods employing, in whole or part, exponential amplification by the polymerase chain reaction (PCR) process.

BACKGROUND

The polymerase chain reaction (PCR) is widely used to amplify stretches of DNA, including cDNA reverse transcribed from RNA, for assays for diagnostic and other purposes. See U.S. Pat. Nos. 4,683,202, 4,683,195 and 4,965,188. See, generally, PCR PROTOCOLS, a Guide to Methods and Applications, Innis et al. eds., Academic Press (San Diego, Calif. (USA) 1990). PCR reactions are generally designed to be symmetric, that is, to make double-stranded copies by utilizing a forward primer and a reverse primer in equimolar concentrations. The two primers are designed to have "melting temperatures," or "$T_m$'s" that are "balanced" (Innis et al., page 9), which is generally understood to mean equal or within a few degrees (° C.) of one another. A commonly used computer software program for primer design warns users to avoid high $T_m$ difference, and has an automatic $T_m$ matching feature. (Oligo® Primer Analysis Software Manual, version 6.0 for Windows, Molecular Biology Insights, Inc., Sixth Edition, March 2000). The $T_m$'s of linear primers comprised of deoxyribonucleotides (DNA) have been commonly determined by the "percent GC" method (Innis et al., page 9) or the "2 (A+T) plus 4 (G+C)" method (Wallace et al. (1979) "Hybridization of Synthetic Oligodeoxyribonucletides to phi chi 174 DNA: the Effect of a Single Base Pair Mismatch," Nucleic Acids Res. 6 (11): 35433557) or the "Nearest Neighbor" method (SantaLucia, J. (1998) "A Unified view of Paymer, Dumbbell, and Oligonucleotide DNA Nearest Neighbor Thermodynamics," Proc. Natl. Acad. Sci. USA 95: 1460-1465; Allawi, H. T. and SantaLucia, J. (1997) "Thermodynamics and NMR of Internal G·T Mismatches In DNA," Biochem. 36: 10581-10594).

PCR is a repeated series of steps of denaturation, or strand melting, to create single-stranded templates; primer annealing; and primer extension by a thermally stable DNA polymerase such as *Thermus aguaticus* (Taq) DNA polymerase. A typical three-step PCR protocol (see Innis et al., Chapter 1) may include denaturation, or strand melting, at 93-95° C. for more than 5 sec, primer annealing at 55-65° C. for 10-60 sec, and primer extension for 15-120 sec at a temperature at which the polymerase is highly active, for example, 72° C. for Taq DNA polymerase. A typical two-step PCR protocol may differ by having the same temperature for primer annealing as for primer extension, for example, 60° C. or 72° C. For either three-step PCR or two-step PCR, an amplification involves cycling the reaction mixture through the foregoing series of steps numerous times, typically 25-40 times. During the course of the reaction the times and temperatures of individual steps in the reaction may remain unchanged from cycle to cycle, or they may be changed at one or more points in the course of the reaction to promote efficiency or enhance selectivity. In addition to the pair of primers and target nucleic acid a PCR reaction mixture typically contains each of the four deoxyribonucleotide 5' triphosphates (dNTPs) at equimolar concentrations, a thermostable polymerase, a divalent cation, and a buffering agent. A reverse transcriptase is included for RNA targets, unless the polymerase possesses that activity. The volume of such reactions is typically 25-100 μl. Multiple target sequences can be amplified in the same reaction. In the case of cDNA amplification, PCR is preceded by a separate reaction for reverse transcription of RNA into cDNA, unless the polymerase used in the PCR possesses reverse transcriptase activity. The number of cycles for a particular PCR amplification depends on several factors including: a) the amount of the starting material, b) the efficiency of the reaction, and c) the method and sensitivity of detection or subsequent analysis of the product. Cycling conditions, reagent concentrations, primer design, and appropriate apparatuses for typical cyclic amplification reactions are well known in the art (see, for example, Ausubel, F. Current Protocols in Molecular Biology (1988) Chapter 15: "The Polymerase Chain Reaction," J. Wiley (New York, N.Y. (USA)).

Ideally, each strand of each amplicon molecule binds a primer at one end and serves as a template for a subsequent round of synthesis. The rate of generation of primer extension products, or amplicons, is thus exponential, doubling during each cycle. The amplicons include both plus (+) and minus (−) strands, which hybridize to one another to form double strands. To differentiate typical PCR from special variations described herein, we refer to typical PCR as "symmetric" PCR. Symmetric PCR thus results in an exponential increase of one or more double-stranded amplicon molecules, and both strands of each amplicon accumulate in equal amounts during each round of replication. The efficiency of exponential amplification via symmetric PCR eventually declines, and the rate of amplicon accumulation slows down and stops. Kinetic analysis of symmetric PCR reveals that reactions are composed of: a) an undetected amplification phase (initial cycles) during which both strands of the target sequence increase exponentially, but the amount of the product thus far accumulated is below the detectable level for the particular method of detection in use; b) a detected amplification phase (additional cycles) during which both strands of the target sequence continue to increase in parallel and the amount of the product is detectable; c) a plateau phase (terminal cycles) during which synthesis of both strands of the amplicon gradually stops and the amount of product no longer increases. Symmetric reactions slow down and stop because the increasing concentrations of complementary amplicon strands hybridize to each other (reanneal), and this out-competes the ability of the separate primers to hybridize to their respective target strands. Typically reactions are run long enough to guarantee accumulation of a detectable amount of product, without regard to the exact number of cycles needed to accomplish that purpose.

Analysis of the amplified product is done by any of several means. For instance, gel electrophoresis or, more recently, capillary electrophoresis has been widely used to separate amplified target sequences, or "amplicons", according to size. Bands on a gel are typically made visible by use of an intercalating dye, such as ethidium bromide or SYBR® Green, or by transferring the nucleic acid to a membrane and then visualizing it with a radioactively or fluorescently labeled hybridization probe. Analysis by sequencing most commonly involves further amplification, using one primer in each of four reaction vessels together with a different dideoxy dNTP. Under these conditions each reaction generates a linear amplification product comprised of a set of oligonucleotides ending in A, T, C or G depending on which dideoxy dNTP was included in the reaction. See, for example, U.S. Pat. No. 5,075,216.

"Real-time" PCR refers to PCR reactions in which a reporter, typically a fluorescent moiety, is present to monitor the accumulation of the amplicon by a change in signal during the reaction. Such moieties include an intercalating dye, such as SYBR® Green, or a hybridization probe (whether or not extendable as a primer). One real-time PCR method, the 5' nuclease process, utilizes labeled linear probes, for example dual fluorescent labeled probes ("TaqMan™ probes"), that are digested by the DNA polymerase during the primer extension step, resulting in a detectable signal change (see U.S. Pat. Nos. 5,210,015, 5,487,972 and 5,538,848). Another method utilizes a dye that fluoresces when in contact with double-stranded DNA (see U.S. Pat. No. 5,994,056). A third method utilizes dual fluorescent labeled probes such as "molecular beacon probes", which are hairpin probes having a fluorophore at one end and a quencher at the other end, and which open and fluoresce when hybridized to their target sequence (see U.S. Pat. Nos. 5,925,517, 6,103,476 and 6,365,729). Other fluorescent labeled probes useful for real-time PCR include Scorpion primers, (primers that have a hairpin probe sequence (containing a fluorophore and a quencher moieties located in close proximity on the hairpin stem) linked to their 5' end via a PCR stopper such that fluorescence occurs only when the specific probe sequence binds to its complement within the same strand of DNA after extension of the primers during PCR; Whitcombe et al. (1999) "Detection of PCR Products Using Self-Probing Amplicons and Fluorescence," Nat. Biotechnol. 17: 804-807), Amplifluor primers (primers that have a hairpin probe sequence (containing a fluorophore and a quencher moieties located in close proximity on the hairpin stem) linked to their 5' end such that fluorescence occurs only when the hairpin unfolds upon replication of the primer following its incorporation into an amplification product; Nazarenko et al. (1997) "A Closed Tube Format for Amplification and Detection of DNA Based on Energy Transfer," Nucleic Acids Res. 15: 2516-21, Eclipse probes (linear DNA probes that have a minor-groove binding (MGB) protein-quencher complex positioned at the 5'-end of the probe and a fluorophore located at the 3'-end of the probe such that fluorescence only occurs when the probe anneals to a target sequence aided by the MGB protein binding to NDA and the quencher moves away from the fluorophore, (Afonina et al., (2002) "Minor Groove Binder-Conjugated DNA Probes for Quantitative DNA Detection by Hybridization-Triggered Fluorescence," Biotechniques 32: 946-9), FRET probes (a pair of random coil, or linear, probes, each of which is fluorescently labeled, that hybridize adjacently on a target sequence, causing their labels to interact by fluorescence resonance energy transfer ("FRET") and produce a detectable signal change), and double-stranded fluorescent probes, (Li, Q. et al. (2002) "A New Class of Homogeneous Nucleic Acid Probes Based on Specific Displacement Hybridization," Nucl. Acid Res. 30: (2)e5). Probes that are not to be cut, hydrolyzed, or extended (that is, probes that are not primers) are typically designed to disengage from their template either prior to or during the primer extension step of PCR so they will not interfere with this phase of the reaction. For probes such as molecular beacon probes, the melting temperature of the probe is generally 7-10° C. higher than the temperature used to anneal the primers. In practice this means that the melting temperature of the probe is higher than the melting temperature of the primer which hybridizes to the same strand as the probe (Mackay, I. M. (2002) "Survey and Summary: Real-time PCR in Virology", Nucleic Acids Res. 30(6): 1292-1305). Thus, as the temperature of the reaction is cooled following strand-melting at 95° C. the probe hybridizes to its target strand (hereafter (+) strand) followed by hybridization of the primer for the (+) strand, as the reaction approaches the annealing temperature. As the reaction is warmed again at the end of the annealing step the probe should fall off of the (+) strand while the primer extends along the (+) strand. Thus, the intent is that the probe should not interfere with primer extension. Hybridization and extension of the other primer on the complementary (−) strand also takes place during these steps. A second probe targeted to the (−) strand may also be present in the reaction.

A technique that has found limited use for making single-stranded DNA directly in a PCR reaction is "asymmetric PCR." Gyllensten and Erlich, "Generation of Single-Stranded DNA by the polymerase chain reaction and its application to direct sequencing of the HLA-DQA Locus," Proc. Natl. Acad. Sci. (USA) 85: 7652-7656 (1988); Gyllensten, U. B. and Erlich, H. A. (1991) "Methods for generating single stranded DNA by the polymerase chain reaction" U.S. Pat. No. 5,066,584, Nov. 19, 1991. Asymmetric PCR differs from symmetric PCR in that one of the primers is added in limiting amount, typically $\frac{1}{100}$ to $\frac{1}{5}$ of the concentration of the other primer. Double-stranded amplicon accumulates during the early temperature cycles, as in symmetric PCR, but one primer is depleted, typically after 15-25 PCR cycles, depending on the number of starting templates. Linear amplification of one strand takes place during subsequent cycles utilizing the undepleted primer. Primers used in asymmetric PCR reactions reported in the literature, including the Gyllensten patent, are often the same primers known for use in symmetric PCR. Poddar (Poddar, S. (2000) "Symmetric vs. Asymmetric PCR and Molecular Beacon Probe in the Detection of a Target Gene of Adenovirus," Mol. Cell Probes 14: 25-32 compared symmetric and asymmetric PCR for amplifying an adenovirus substrate by an end-point assay that included 40 thermal cycles. He reported that a primers ratio of 50:1 was optimal and that asymmetric PCR assays had better sensitivity that, however, dropped significantly for dilute substrate solutions that presumably contained lower numbers of target molecules.

Although asymmetric PCR has been known since 1988, it has not been extensively used as a technique because of the need to spend a great deal of time optimizing the experimental conditions for each amplicon. J. K. Ball and R. Curran (1997) "Production of Single-Stranded DNA Using a Uracil-N-glycosylase-Mediated Asymmetric Polymerase Chain Reaction Method," Analytical Biochemistry 253: 264-267, states: "To ensure that asymmetric amplification occurs several replicate tubes containing different concentrations of each primer are set up, and for this reason the technique is not used extensively."

SUMMARY

As used herein, certain terms have defined meanings, as follows:

$T_m$, or melting temperature, of an oligonucleotide describes the temperature (in degrees Celsius) at which 50% of the molecules in a population of a single-stranded oligonucleotide are hybridized to their complementary sequence and 50% of the molecules in the population are not-hybridized to said complementary sequence. The $T_m$ of a primer or probe can be determined empirically by means of a melting curve. In some cases it can also be calculated. For the design of symmetric and asymmetric PCR primer pairs, balanced $T_m$'s are generally calculated by one of the three methods discussed earlier, that is, the "% GC", or the "2(A+T) plus 4 (G+C)", or "Nearest Neighbor" formula at some chosen set of conditions of monovalent salt concentration and primer concentration. In the case of Nearest Neighbor calculations the $T_m$'s of both primers will depend on the concentrations chosen for use in calculation or measurement, the difference between the $T_m$'s of the two primers will not change substantially as long as the primer concentrations are equimolar, as they normally are with respect to PCR primer measurements and calculations. $T_{m[1]}$ describes the calculated $T_m$ of a PCR primer at particular standard conditions of 1 micromolar (1 µM=$10^{-6}$ M) primer concentration, and 0.07 molar monovalent cations. In this application, unless otherwise stated, $T_{m[1]}$ is calculated using Nearest Neighbor formula, $T_m=\Delta H/(\Delta S+R \ln (C/2))-273.15+12 \log [M]$. This formula is based on the published formula (Le Novere, N. (2001), "MELTING, Computing the Melting Temperature of Nucleic Acid Duplex," Bioinformatics 17: 1226-7). $\Delta H$ is the enthalpy and $\Delta S$ is the entropy (both $\Delta H$ and $\Delta S$ calculations are based on Allawi and SantaLucia, 1997), C is the concentration of the oligonucleotide ($10^{-6}$ M), R is the universal gas constant, and [M] is the molar concentration of monovalent cations (0.07). According to this formula the nucleotide base composition of the oligonucleotide (contained in the terms $\Delta H$ and $\Delta S$), the salt concentration, and the concentration of the oligonucleotide (contained in the term C) influence the $T_m$. In general for oligonucleotides of the same length, the $T_m$ increases as the percentage of guanine and cytosine bases of the oligonucleotide increases, but the $T_m$ decreases as the concentration of the oligonucleotide decreases. In the case of a primer with nucleotides other than A, T, C and G or with covalent modification, $T_{m[1]}$ is measured empirically by hybridization melting analysis as known in the art.

$T_{m[0]}$ means the $T_m$ of a PCR primer or probe at the start of a PCR amplification taking into account its starting concentration, length, and composition. Unless otherwise stated, $T_{m[0]}$ is the calculated $T_m$ of a PCR primer at the actual starting concentration of that primer in the reaction mixture, under assumed standard conditions of 0.07 M monovalent cations and the presence of a vast excess concentration of a target oligonucleotide having a sequence complementary to that of the primer. In instances where a target sequence is not fully complementary to a primer it is important to consider not only the $T_{m[0]}$ of the primer against its complements but also the concentration-adjusted melting point of the imperfect hybrid formed between the primer and the target. In this application, $T_{m[0]}$ for a primer is calculated using the Nearest Neighbor formula and conditions stated in the previous paragraph, but using the actual starting micromolar concentration of the primer. In the case of a primer with nucleotides other than A, T, C and G or with covalent modification, $T_{m[0]}$ is measured empirically by hybridization melting analysis as known in the art.

As used herein superscript X refers to the Excess Primer, superscript L refers to the Limiting Primer, superscript A refers to the amplicon, and superscript P refers to the probe.

$T_m^A$ means the melting temperature of an amplicon, either a double-stranded amplicon or a single-stranded amplicon hybridized to its complement. In this application, unless otherwise stated, the melting point of an amplicon, or $T_m^A$, refers to the $T_m$ calculated by the following % GC formula: $T_m^A=81.5+0.41$ (% G+% C)$-500/L+16.6 \log [M]/(1+0.7 [M])$, where L is the length in nucleotides and [M] is the molar concentration of monovalent cations.

$T_{m[0]}^P$ refers to the concentration-adjusted melting temperature of the probe to its target, or the portion of probe that actually is complementary to the target sequence (e.g., the loop sequence of a molecular beacon probe). In the case of most linear probes, $T_{m[0]}^P$ is calculated using the Nearest Neighbor formula given above, as for $T_{m[0]}$, or preferably is measured empirically. In the case of molecular beacons, a rough estimate of $T_{m[0]}^P$ can be calculated using commercially available computer programs that utilize the % GC method, see Marras, S. A. et al. (1999) "Multiplex Detection of Single-Nucleotide Variations Using Molecular Beacons," Genet. Anal. 14:151-156, or using the Nearest Neighbor formula, or preferably is measured empirically. In the case of probes having non-conventional bases and for double-stranded probes, $T_{m[0]}^P$ is determined empirically.

$C_T$ means threshold cycle and signifies the cycle of a real-time PCR amplification assay in which signal from a reporter indicative of amplicons generation first becomes detectable above background. Because empirically measured background levels can be slightly variable, it is standard practice to measure the $C_T$ at the point in the reaction when the signal reaches 10 standard deviations above the background level averaged over the 5-10 preceding thermal cycles.

As used herein, the terms "hybridize" or "hybridization" are art-known and include the hydrogen bonding of complementary DNA and/or RNA sequences to form a duplex molecule. As used herein, hybridization takes place under conditions that can be adjusted to a level of stringency that reduces or even prevents base-pairing between a first oligonucleotide primer or oligonucleotide probe and a target sequence, if the complementary sequences are mismatched by as little as one base-pair. Thus, the term "stringent conditions" for hybridization includes conditions that minimize or prevent base-pairing between an oligonucleotide primer or oligonucleotide probe and another sequence if the complementary sequences are mismatched. When hybridization probes such as differently-labeled sequence-specific molecular beacon probes are used under stringent conditions they are observed to be "allele-discriminating" because mismatches as little as one base-pair are sufficient to destabilize hybridization of the incorrect probe. In the context of real-time PCR "allele discrimination" is achieved by careful attention to the design of the probe, the concentration of magnesium, and the temperature at which it hybridizes to its target. Single base pair mismatches between the loop sequence of the probe and its target sequence tend to have greater destabilizing effects in the case of molecular beacons with short rather than long loop sequences. For this reason molecular beacons with short rather than long loop sequences are usually more "allele discriminating."

As used herein "amplification target sequence" for PCR amplification means a DNA sequence that provides a template for copying by the steps of PCR. An amplification target sequence may be single-stranded or double-stranded. If the starting material is RNA, for example messenger RNA, the DNA amplification target sequence is created by reverse transcription of RNA to create complementary DNA, and the amplification target sequence is a cDNA molecule. Thus, in a PCR assay for RNA a hybridization probe signals copying of a cDNA amplification target sequence, indirectly signifying the presence of the RNA whose reverse transcription produced the cDNA molecules containing the amplification target sequence. An amplification target sequence is bracketed in length by the pair of primers used to amplify it. There will be a small amount of longer extension product, as explained in Mullis U.S. Pat. No. 4,683,202, that is not exponentially amplified, but the extension product of interest, whether double-stranded or, in non-symmetric PCR, single-stranded, is the exponentially amplified sequence, the amplicon, bracketed by the primer pair. An amplification target sequence may be a single sequence. However, in some cases an amplification target sequence will contain allelic variations and, thus, not be a single sequence, even though amplified by a single primer pair. An assay for an amplification target sequence containing variations may utilize one detector probe for all variations, a single allele-discriminating probe for one variant, or multiple allele-discriminating probes, one for each variant.

As used interchangeably herein, the terms "nucleic acid primer", "primer molecule", "primer", and "oligonucleotide primer" include short (usually between about 16 and about 50 bases) single-stranded oligonucleotides which, upon hybridization with a corresponding template nucleic acid molecule, serve as a starting point for synthesis of the complementary nucleic acid strand by an appropriate polymerase molecule. Primer molecules may be complementary to either the sense or the anti-sense strand of a template nucleic acid molecule. A primer may be composed of naturally occurring or synthetic oligonucleotides, or a mixture of the two. If the primers in a pair of PCR primers are used in unequal concentrations, the primer added at the lower concentration is the "Limiting Primer", and the primer added at the higher concentration is the "Excess Primer."

As used interchangeably herein, the terms "nucleic acid probe", "probe molecule", and "oligonucleotide probe" and "hybridization probe" include defined nucleic acid sequences complementary to a target nucleic acid sequence to be detected such that the probe will hybridize to the target. Probes are typically detectably labeled, such that the hybridization of the probe to the target sequence may be readily assessed. Probes can be composed of naturally occurring or synthetic oligonucleotides and include labeled primers. Some hybridization probes, for example molecular beacon probes, emit a detectable signal upon hybridizing to their complementary sequence without enzymatic action to hydrolyze the probes to generate a signal. We refer to such probes as probes that hybridize to their target and "signal upon hybridization." Other probes, for example TaqMan™ dual fluorescently labeled random coil probes are cut, or hydrolyzed, during the amplification reaction, and hydrolysis leads to a signal change, which is detected. Probes that rely on hydrolysis as part of signal generation are not probes that "signal upon hybridization."

A "molecular beacon probe" is a single-stranded oligonucleotide, typically 25-35 bases-long, in which the bases on the 3' and 5' ends are complementary, typically for 5-8 bases. A molecular beacon probe forms a hairpin structure at temperatures at and below those used to anneal the primers to the template (typically below about 60° C.). The double-helical stem of the hairpin brings a fluorophore attached to the 5' end of the probe very close to a quencher attached to the 3' end of the probe. The probe does not fluoresce in this conformation. If a probe is heated above the temperature needed to melt the double stranded stem apart, or the probe is allowed to hybridize to a target oligonucleotide that is complementary to the sequence within the single-strand loop of the probe, the fluorophore and the quencher are separated, and the resulting conformation fluoresces. Therefore, in a series of PCR cycles the strength of the fluorescent signal increases in proportion to the amount of the beacon hybridized to the amplicon, when the signal is read at the annealing temperature. Molecular beacons with different loop sequences can be conjugated to different fluorophores in order to monitor increases in amplicons that differ by as little as one base (Tyagi, S. and Kramer, F. R. (1996) "Molecular Beacons: Probes That Fluoresce Upon Hybridization," Nat. Biotech. 14:303-308; Tyagi, S. et al., (1998) "Multicolor Molecular Beacons for Allele Discrimination." Nat. Biotech. 16: 49-53; Kostrikis, L. G. et al., (1998) "Spectral Genotyping of Human Alleles," Science 279: 1228-1229).

As used herein, the term "detectable label" includes moieties that provide a signal that may be readily detected and, in some embodiments, quantified. Such labels are well known to those in the art and include chemiluminescent, radioactive, metal ion, chemical ligand, fluorescent, or colored moieties, or enzymatic groups which, upon incubation with an appropriate substrate, provide a chemiluminescent, fluorescent, radioactive, electrical, or colorimetric signal. Methods of detection of such signals are also well known in the art.

As used herein, the term "buffer" includes compounds that act to maintain the pH of a solution by maintaining the relative levels of hydrogen and hydroxyl ions in the solution. Buffers have specific pH ranges at which they are functional, and their function is frequently temperature-dependent. Buffers and the temperature-dependence of the buffering capacity thereof are well known to those skilled in the art.

As used herein, the term "real time", with respect to an amplification reaction, refers to the method by which the amplification reaction is detected. In a "real-time" amplification reaction, accumulation of amplicon or product is measured during the progression of the reaction, as opposed to solely after the reaction is complete, the latter being "endpoint" analysis.

As used herein, the term "Optimal Annealing Temperature" is the highest temperature at which the exponential phase of the reaction proceeds with maximal efficiency and without generating substantial non-specific products at specific reagent concentrations and cycling times. By "maximum efficiency" we mean the condition that generates the lowest $C_T$ value during the exponential phase of reaction, wherein the specific product accumulates at the highest rate.

This invention includes an amplification method that we refer to as "Linear-After-The Exponential PCR" or, for short, "LATE-PCR." LATE-PCR is a non-symmetric PCR method; that is, it utilizes unequal concentrations of primers and yields single-stranded primer-extension products, or amplicons. LATE-PCR includes innovations in primer design, in temperature cycling profiles, and in hybridization probe design. Being a type of PCR process, LATE-PCR utilizes the basic steps of strand melting, primer annealing, and primer extension by a DNA polymerase caused or enabled to occur repeatedly by a series of temperature cycles. In the early cycles of a LATE-PCR amplification, when both primers are present, LATE-PCR amplification amplifies both strands of a target sequence exponentially, as occurs in conventional symmetric PCR. LATE-PCR then switches to synthesis of only one strand of the target sequence for additional cycles of amplification. In preferred real-time LATE-PCR assays according to this invention, the Limiting Primer is exhausted within a few cycles after the reaction reaches its $C_T$ value, and in the most preferred assays one cycle after the reaction reaches its $C_T$ value. As defined above, the $C_T$ value is the thermal cycle at which signal becomes detectable above the empirically determined background level of the reaction. Whereas a symmetric PCR amplification typically reaches a plateau phase and stops generating new amplicons by the $50^{th}$ thermal cycle, LATE-PCR amplifications do not plateau and continue to generate single-stranded amplicons well beyond the $50^{th}$ cycle, even through the $100^{th}$ cycle. LATE-PCR amplifications and assays typically include at least 60 cycles, preferably at least 70 cycles when small (10,000 or less) numbers of target molecules are present at the start of amplification.

With exceptions and limitations to be described, the ingredients of a reaction mixture for LATE-PCR amplification are the same as the ingredients of a reaction mixture for a corresponding symmetric PCR amplification. The mixture typically includes each of the four deoxyribonucleotide 5' triphosphates (dNTPs) at equimolar concentrations, a thermostable polymerase, a divalent cation, and a buffering agent. As with symmetric PCR amplifications, it may include additional ingredients, for example reverse transcriptase for RNA targets. Non-natural dNTPs may be utilized. For instance, dUTP can be substituted for dTTP and used at 3 times the concentration of the other dNTPs due to the less efficient incorporation by Taq DNA polymerase.

As used herein, the term "Low-$T_m$ Probe" means a labeled hybridization probe that signals upon hybridization to its target, which in a LATE-PCR is the Excess Primer-Strand generated by extension of the Excess Primer, and that has a $T_{m[0]}^P$ at least 5° C. below and more preferably at least 10° C. below the $T_{m[0]}$ of the primer that hybridizes to and extends along the Excess Primer-Strand, which in a LATE-PCR is the Limiting Primer.

As used herein, the term "Super-Low-$T_m$ Probe" means a labeled hybridization probe that signals upon hybridization to its target, which in a LATE-PCR is the Excess Primer-Strand generated by extension of the Excess Primer (that is, a Low-$T_m$ Probe), and that has a $T_{m[0]}^P$ that is at least 5° C. below, and more preferably 10° C. below the mean annealing temperature of the exponential phase of the reaction.

$T_{m[1]}$ for a PCR primer is calculated at standard conditions of primers concentration and salt concentration. We have chosen 1 µM as the standard concentration of the primers, because that concentration is a typical concentration for the Excess Primer in a LATE-PCR amplification. In LATE-PCR amplifications the Limiting Primer concentration is typically many fold times less than that standard concentration. Lowering the concentration of the Limiting Primer lowers its melting temperature, $T_{m[0]}^L$, in a reaction mixture. Thus, a matched primer pair for symmetric PCR, having equal $T_{m[1]}$'s will not have matched $T_{m[0]}$'s when used at unequal concentrations. As a rule of thumb, a primer pair that is perfectly matched, that is, for which $(T_{m[1]}^L - T_{m[1]}^X)$ is zero, $(T_{m[0]}^L - T_{m[0]}^X)$ will be less than zero at primer concentrations used for LATE-PCR. Our observation is that primer pairs having equivalent initial concentration-adjusted melting temperature at the start of the reaction, i.e. $(T_{m[0]}^L - T_{m[0]}^X) = 0$, will according to this invention have a difference in their standard calculated melting temperatures, for example $(T_{m[1]}^L - T_{m[1]}^X)$ in the range of +5-to-+20° C. (e.g., about 5° C., 6° C., 7° C., 8° C., 9° C., 10° C., 11° C., 12° C., 13° C., 14° C., 15° C., 16° C., 17° C., 18° C., 19° C. or 20° C.).

For amplifications according to this invention the starting molar concentration of one primer, the "Limiting Primer", is less than the starting molar concentration of the other primer, the "Excess Primer." The ratio of the starting concentrations of the Excess Primer and the Limiting Primer is at least 5:1, preferably at least 10:1, and more preferably at least 20:1. The ratio of Excess Primer to Limiting Primer can be 5:1, 10:1, 15:1, 20:1, 25:1, 30:1, 35:1, 40:1, 45:1, 50:1, 55:1, 60:1, 65:1, 70:1, 75:1, 80:1, 85:1, 90:1, 95:1, or 100:1, most preferably in the range of 20:1 to 100:1. Primer length and sequence are adjusted or modified, preferably at the 5' end of the molecule, such that the concentration-adjusted melting temperature of the Limiting Primer at the start of the reaction, $T_{m[0]}^L$, is greater than or equal (±0.5° C.) to the concentration-adjusted melting point of the Excess Primer at the start of the reaction, $T_{m[0]}^X$. Preferably the difference $(T_{m[0]}^L - T_{m[0]}^X)$ is at least +3, and more preferably the difference is at least +5° C.

Amplifications according to this invention can be used to generate single-stranded products for further use, for example as starting material for DNA sequencing or as probes in other reactions, or can be used in assays, including quantitative real-time assays, of specific nucleic acid sequences. In all cases there is a relationship between $T_{m[0]}^X$ and $T_m^A$, which LATE-PCR takes into account. $T_m^A$ is higher than $T_{m[0]}^X$, but if the difference between these two values is too great, lower amounts of single-stranded product will be generated. In the case of reactions designed to generate products for subsequent use or analysis $(T_m^A - T_{m[0]}^X)$ should be less than or equal to 18° C., preferably not more that 15° C. For real-time assays that employ non-hydrolyzing probes, $(T_m^A - T_{m[0]}^X)$ should in all cases be less that 25° C., preferably less than 20° C., and more preferably less than 18° C.

Amplifications and assays according to this invention can be performed with initial reaction mixtures having ranges of concentrations of target molecules and primers. LATE-PCR assays according to this invention are particularly suited for amplifications that utilize small reaction-mixture volumes and relatively few molecules containing the target sequence, sometimes referred to as "low copy number." While LATE-PCR can be used to assay samples containing large amounts of target, for example up to $10^6$ copies of target molecules, our preferred range is a much smaller amount, from to 1-50,000 copies, more preferably 1-10,000 copies and even more preferably 1-1,000 copies. The concentration of Limiting Primer should be from a few nanomolar (nM) up to 200 nM. The Limiting Primer concentration is preferably as far toward the low end of the range as detection sensitivity permits. Our preferred range with probes and detections available to us, as described below, is 20-100 nM.

As with PCR, either symmetric or asymmetric, LATE-PCR amplifications according to this invention include repeated thermal cycling through the steps of strand melting, primer annealing and primer extension. Temperatures and times for the three steps are typically, as with symmetric PCR, 93-95° C. for at least 5 sec for strand melting, 55-65° C. for 10-60 sec for annealing primers, and 72° C. for 15-120 sec for primer extension. For 3-step PCR amplifications according to this invention, primer annealing times longer than 30 sec are not preferred. Our more preferred range is 10-20 sec. Variations of temperature and time for PCR amplifications are known to persons skilled in the art and are generally applicable to LATE-PCR as well. For example, so-called "2-step" PCR, in which one temperature is used for both primer annealing and primer extension, can be used for LATE-PCR. In the case of "2-step" reactions the combined annealing-extension step can be longer than 30 sec, but preferably as short as possible and not longer that 120 sec.

An aspect of this invention is a non-symmetric polymerase chain reaction (PCR) method comprising repeatedly thermally cycling a PCR reaction mixture containing a deoxyribonucleic acid (DNA) target sequence, a pair of PCR primers, dNTP's and a thermostable polymerase through PCR steps of strand melting, primer annealing and primer extension, wherein, at the outset (a) the reaction mixture contains up to 1,000,000 copies of the nucleic acid target, (b) the PCR primer pair comprises a Limiting Primer and an Excess Primer, the Limiting Primer being present at a concentration of up to 200 nM and the Excess Primer being present at a concentration at least five times higher than the Limiting Primer, (c) the initial, concentration-adjusted melting temperature of the Limiting Primer is equal to or greater than the initial, concentration-adjusted melting temperature of the Excess Primer, (d) the concentration-adjusted melting temperature of that portion of the Limiting Primer which hybridizes to said target sequence is not more than 5° C. below the concentration-adjusted melting temperature of the Excess Primer, (e) the melting temperature of the amplicon produced by extension of the Excess Primer exceeds the initial concentration-adjusted melting temperature of the Excess Primer by not more than 18° C., and (f) thermal cycling is repeated a number of times sufficient to include multiple cycles of linear amplification using the Excess Primer following exhaustion of the Limiting Primer. The foregoing method may also be for two or more target sequences wherein the reaction mixture includes a pair of PCR primers for each target. The method may also include reverse transcribing a ribonucleic acid (RNA) molecule to generate the DNA target sequence.

Another aspect of this invention is the amplification method described above applied to low copy numbers of target, wherein the reaction mixture contains only 50,000 copies of the nucleic acid target or even 10,000 copies, 1000 copies or one copy, or DNA or cDNA from a single cell.

Another aspect of this invention is the amplification method described above wherein the initial, concentration-adjusted melting temperature of the Limiting Primer is 3-10° C. higher than the initial, concentration-adjusted melting temperature of the Excess Primer and, optionally but preferably, wherein the Excess Primer is present at a concentration of 500-2000 nM and at least ten times higher than the Limiting Primer, and, also optionally but preferably, wherein the melting temperature of the amplicon is 7-15° C. higher than the initial, concentration-adjusted melting temperature of the Excess Primer.

Another aspect of this invention is the method described above wherein the duration of the primer annealing step is not longer than 30 seconds.

Another aspect of this invention is a variant of the method described above further including at least one terminal thermal cycle in which the single-stranded extension product of the Excess Primer is converted to double-stranded product, by including in the PCR reaction mixture a low-temperature primer capable of priming the extension product of the Excess Primer and having an initial, concentration-adjusted melting point at least 5° C. below, more preferably at least 10° C. below, the initial, concentration-adjusted melting point of the Excess Primer, and wherein the annealing temperature is maintained above the initial, concentration-adjusted melting temperature of the low-temperature primer except for at least one terminal cycle in which the annealing temperature is lowered to hybridize the low-temperature primer.

Another aspect of this invention is a non-symmetric polymerase chain reaction (PCR) method comprising thermally cycling a PCR reaction mixture containing a deoxyribonucleic acid (DNA) target sequence, a pair of matched Limiting PCR Primers, an additional Excess Primer, dNTP's and a thermostable polymerase repeatedly through PCR steps of strand melting, primer annealing and primer extension, wherein the matched PCR primers are present in approximately equimolar concentration of up to 200 nM, the Excess Primer is present at a concentration at least five times higher than the Limiting Primers, the initial, concentration-adjusted melting temperatures of the Excess Primers is at least 5° C. below, more preferably at least 10° C. below, the concentration-adjusted melting temperatures of the Limiting Primers, and wherein the reaction comprises a first phase wherein the annealing temperature is higher than the initial, concentration-adjusted melting temperature of the Excess Primer, and the matched Limiting Primers generate a first amplicon, and a second phase wherein the annealing temperature is lowered and the Excess Primer generates a second amplicon, shorter than the first amplicon, utilizing the first amplicon as a template strand, and wherein the melting temperature of the second amplicon exceeds the initial, concentration-adjusted melting temperature of the Excess Primer by not more than 25° C., more preferably by not more than 18° C.

Another aspect of this invention is a non-symmetric polymerase chain reaction (PCR) method with removal of single-stranded amplicon comprising a) thermally cycling a PCR reaction mixture containing a DNA target, a pair of PCR primers for said target, dNTP's and a thermostable DNA polymerase through repeated cycles of strand melting, primer annealing and primer extension, wherein (i) the PCR primer pair comprises a Limiting Primer and an Excess Primer, (ii) the Limiting Primer is present at a concentration of up to 200 nM, and the Excess Primer is present at a concentration at least five times higher than the Limiting Primer, (iii) the initial, concentration-adjusted melting temperature of the Limiting Primer is at least equal to, more preferably 3-10° C. higher than, the initial, concentration-adjusted melting temperature of the Excess Primer, and (iv) thermal cycling is repeated a number of times sufficient to include multiple cycles of linear amplification using the Excess Primer following exhaustion of the Limiting Primer; and b) during at least the cycles of linear amplification, following the step of primer extension permanently removing the single-stranded extension product of the Excess Primer from the reaction mixture by hybridizing said product to immobilized capture probes. In preferred versions of the method the immobilized capture probes are in a thermally isolated product removal zone and said step of removing comprises passing the reaction mixture through said zone. In certain preferred versions of this method the capture probes are isolatable (for example, beads that can be physically removed from the reaction mixture) or are in a product removal zone that itself is physically isolatable from said at least one reaction zone, further including periodically isolating said capture probes and harvesting product hybridized to said capture probes not in contact with the reaction mixture, such as while the reaction mixture is in said at least one reaction zone. In other preferred versions the melting temperature of the amplicon exceeds the concentration-adjusted melting temperature of the Excess Primer by not more than 18° C. In yet other preferred versions the Excess Primer is present at a concentration of 500-2000 mM and at least ten times higher than the Limiting Primer.

Another aspect of this invention is a homogeneous real-time detection assay for a DNA target sequence employing non-symmetric polymerase chain reaction (PCR) amplification, comprising thermally cycling a PCR reaction mixture containing said target sequence, a pair of PCR primers for amplifying said target sequence, dNTP's, at least one labeled hybridization probe that binds to the amplicon product by said amplification, and a thermostable DNA polymerase through repeated PCR steps of strand melting, primer annealing, and primer extension, wherein (i) the PCR primer pair comprises a Limiting Primer and an Excess Primer, (ii) the Limiting Primer is present at a concentration of up to 200 nM, and the Excess Primer is present at a concentration of at least five times higher than the Limiting Primer, (iii) the initial, concentration-adjusted melting temperature of the Limiting Primer is at least equal to the initial, concentration-adjusted melting temperature of the Excess Primer, (iv) said probe hybridizes to said amplicon during the primer annealing step of PCR, (v) the melting temperature of the amplicon exceeds the initial, concentration-adjusted melting temperature of the Excess Primer by not more than 25° C., and (vi) thermal cycling is repeated a number of times sufficient to include multiple cycles of linear amplification using the Excess Primer following exhaustion of the Limiting Primer, and (vii)

said probe emits a detectable signal indicative of product generation during said linear amplification. In certain versions of this assay the hybridization probe is a dual-labeled fluorescent probe that binds to the extension product of the Limiting Primer and that is hydrolyzed by the polymerase during extension of the Excess Primer, thereby generating a detectable signal. In more preferred versions the hybridization probe (or probes) is a dual-labeled fluorescent probe that binds to the extension product of the Excess Primer and that signals upon hybridization, such as molecular beacon probes, FRET probe pairs, hybridized probe pairs, and Excess Primers containing attached hairpin probes. Certain preferred versions include a first probe for one allelic variant and a second probe for another allelic variant. The assay may include reverse transcribing of ribonucleic acid (RNA) molecules to generate cDNA containing target sequences.

The foregoing assay may be for small copy numbers of targets, such as wherein the reaction mixture contains up to 50,000 copies of the nucleic acid target, or even 1000 copies, or one copy or cDNA from a single cell. In certain preferred embodiments the initial, concentration-adjusted melting temperature of the Limiting Primer is 3-10° C. higher than the in initial, concentration-adjusted melting temperature of the Excess Primer. In certain preferred embodiments the Excess Primer is present at a concentration of 500-2000 nM and at least ten times higher than the Limiting Primer. In certain preferred embodiments the melting temperature of the amplicon is 7-15° C. higher than the initial, concentration-adjusted melting temperature of the Excess Primer. In our most preferred embodiments the duration of the primer annealing step is not longer than 30 seconds.

LATE-PCR can be combined with the use of very bright probes, such as probes labeled with Quantum Dots®, which permit detection of small numbers or very small numbers of DNA molecules, in the range of 1000 to one million single strands. As the signal strength of the probe is increased, the number of single-stranded molecules that have to be generated by the LATE-PCR decreases. This can be accomplished by reducing the absolute concentration of the Limiting Primer or by decreasing the volume of the reaction at a constant limiting Primer concentration. As the absolute concentration of the Limiting Primer is decreased and the number of single-stranded molecules produced is decreased, detection of smaller numbers of molecules takes place under conditions in which the Excess Primer does not have to compete with reannealing of the product single-strand to the target strand. LATE-PCR reactions carried out in the presence of bright probes is well suited to miniaturization, for instance for production of chips and chambers that carry out reactions using microfluidics. Therefore, the requirement that $(T_m^A - T_{m[0]}^X) \leq 25$ becomes relaxed.

Another aspect of this invention is a homogeneous detection assay for a DNA target sequence employing non-symmetric polymerase chain reaction (PCR) amplification, comprising thermally cycling a PCR reaction mixture containing said target sequence, a pair of PCR primers for said target sequence, dNTP's, a labeled low-temperature hybridization probe, and a thermostable DNA polymerase repeatedly through PCR steps of strand melting, primer annealing and primer extension, wherein (i) the PCR primer pair comprises a Limiting Primer and an Excess Primer, (ii) the Limiting Primer is present at a concentration of up to 200 nM, and the Excess Primer is present at a concentration of at least five times the concentration of the Limiting Primer, (iii) the initial, concentration-adjusted melting temperature of the limiting primer is equal to or greater than the initial, concentration-adjusted melting temperature of the Excess Primer, (iv) the melting temperature of the amplicon exceeds the initial, concentration-adjusted melting temperature of the Excess Primer by not more than 25° C., (v) the low-temperature hybridization probe binds to the extension product of the Excess Primer and emits a detectable signal upon hybridization, (vi) the initial, concentration-adjusted melting temperature of the low-temperature hybridization probe is at least 5° below the initial, concentration-adjusted melting temperature of the Limiting Primer, (vii) thermal cycling is repeated a number of times sufficient to include multiple cycles of linear amplification using the Excess Primer following exhaustion of the Limiting Primer, and (viii) detection is performed at a temperature below said optimal annealing temperature.

In certain embodiments of this assay the initial, concentration-adjusted melting temperature of the low-temperature hybridization probe is at least 10° C. below the initial, concentration-adjusted melting temperature of the Limiting Primer. In some embodiments of is this assay primer annealing is of sufficiently low temperature and of sufficient duration that the low-temperature probe hybridizes during primer annealing, the signal detection is performed during that step. In more preferred embodiments the PCR amplification includes, for at least the last few cycles of exponential amplification and the subsequent cycles of linear amplification, an added detection step following primer extension, said detection step being of sufficiently low temperature and sufficient duration for the low-temperature hybridization probe to hybridize and signal, and wherein the PCR step of primer annealing is not of sufficiently low temperature and/or of sufficient duration for said probe to hybridize and signal. In certain preferred embodiments the initial concentration-adjusted melting temperature of the low-temperature hybridization probe is at least 5° C. below, more preferably at least 10° C. below, the temperature of the annealing step of the amplification reaction, and wherein at least the linear amplification cycles include a low-temperature detection step, preferably of 10-30 seconds duration, following primer extension in which the temperature is lowered below the annealing temperature to hybridize said probe, and detection is performed. In a version of these embodiments the PCR reaction mixture additionally includes a low-temperature masking oligonucleotide that is complementary to the Excess Primer and that has an initial, concentration-adjusted melting point at least 5° C. below the initial, concentration-adjusted melting point of the Excess Primer. In other versions the low-temperature hybridization probe is a molecular beacon probe.

Another aspect of this invention is oligonucleotide sets containing the primers or the primers and the probes for performing the foregoing amplifications and assays. Primers are preferably used together in a single buffer so that the ratio of Limiting Primer to Excess Primer is fixed. Also preferably an oligonucleotide set specifies an intended concentration of at least one primer or a mixture of the two, to ensure that $(T_{m[0]}^L - T_{m[0]}^X)$ meets the criterion of the invention.

Another aspect of this invention is reagent kits for performing the foregoing assays. The kits include, in addition to the primers and probes, at least a DNA polymerase and dNTP's. Preferably all reagents necessary to perform the assay are included. However, individual reagents, such as, for example the polymerase, may be separately packaged. Kits should include instructions for performing particular assays.

Another aspect of this invention is a method for amplification of a nucleic acid target sequence present in a sample containing from one to about 10,000 copies of said target sequence, the method comprising:

a) contacting the nucleic acid target sequence with a first oligonucleotide primer and a second oligonucleotide primer, wherein the $T_m$ of the first primer is at least 5° C. greater, preferably 10° C. or even 20° C. greater, than the $T_m$ of the second primer and wherein the concentration of the second primer is up to 1000 mM and at least about 10 times greater, or even 20-100 times greater, than the concentration of the first primer; and b) amplifying the target sequence by a polymerase chain reaction utilizing said first and second oligonucleotide primers, said reaction having an exponential phase of amplicon generation followed by a linear phase of amplicon generation that utilizes only the second primer.

Another aspect of this invention is a method for detecting at least one nucleic acid sequence in a sample containing up to about 10,000 copies of said at least one nucleic acid sequence, the method comprising:

a) contacting the at least one nucleic acid target sequence with a first oligonucleotide primer hybridizable thereto and a second oligonucleotide primer hybridizable thereto, wherein the $T_m$ of the first primer is at least 5° C. greater, preferably 10° C. to 20° C. greater, than the $T_m$ of the second primer and wherein the concentration of the second primer is up to 1000 nM and at least about 10 times greater than the concentration of the second primer;

b) amplifying the at least one target sequence by a polymerase chain reaction utilizing said first and second oligonucleotide primers, said reaction having an exponential phase of amplicon generation followed by a linear phase of amplicon generation that utilizes only the second primer; and c) detecting amplicon generated from said second primer in real time during the polymerase chain reaction by means of a first hybridization probe targeted thereto. The nucleic acid sequence may be a genetic sequence subject to allelic mutation wherein said first hybridization probe is targeted to a first allelic variant. Amplicon generated from said second primer may be detected in real time during the polymerase chain reaction by means of a second hybridization probe targeted to a second allelic variant. In certain embodiments the concentration of the second primer is 20-100 times the concentration of the first primer. This method may be utilized to detect at least two different nucleic acid sequences, in which case the method comprises contacting each nucleic acid sequence with a first primer hybridizable thereto and a second primer hybridizable thereto. In certain preferred embodiments detection is performed between the PCR steps of primer extension step and strand melting step, preferably at a temperature below the primer extension temperature. The probe may be a molecular beacon probe or a double strand probe, among others.

Another aspect of this invention is a composition comprising at least one pair of polymerase chain reaction primers for at least one pre-selected nucleic acid target sequence, said at least one pair comprising a first primer and a second primer, wherein the $T_m$ of the first primer is at least 5° C. greater, preferably 10-20° C. greater, than the $T_m$ of the second primer and wherein the concentration of the second primer is at least 10 times greater, preferably 20-100 times greater, than the concentration of the first primer. Embodiments of this aspect of the invention include at least one hybridization probe, preferably one is targeted against the extension product of the second primer. The probe may be a molecular beacon probe.

Another aspect of this invention is a kit of reagents for performing a real-time polymerase chain reaction assay for at least one pre-selected nucleic acid target sequence, comprising at least one pair of polymerase chain reaction primers including a first primer and a second primer, four deoxyribonucleotide triphosphates, a thermostable DNA polymerase, and a labeled hybridization probe that emits a detectable signal upon hybridization, wherein a) the $T_m$ of the first primer is at least 5° C. greater, preferably 10-20° C. greater, than the $T_m$ of the second primer and the concentration of the second primer is at least 10 times greater, preferably 20-100 times greater, than the concentration of the second primer, and b) said labeled hybridization probe, which may be a molecular beacon, is targeted against the extension product of said second primer.

This invention also includes assays utilizing LATE-PCR amplification, including both end-point assays, which may or may not be homogeneous assays, and homogeneous real-time assays utilizing labeled hybridization probes (including labeled primers) that produce a signal change due to extension of the Excess Primer to make single-stranded amplicons during the later cycles of amplification. Detection methods known for PCR can be applied to LATE-PCR assays.

Preferred LATE-PCR assays utilize labeled hybridization probes that are complementary to a sequence in the single-stranded amplicon produced by extension of the Excess Primer and emit a detectable signal upon hybridization. During the latter phase of LATE-PCR, when single-stranded amplicon is being produced, that single strand does not serve as a template strand. Hence, while TaqMan™ dual-labeled probes that are cut by DNA polymerase during primer extension can be used in LATE-PCR assays, they are not suitable to measure single-stranded product directly. Probes such as molecular beacon probes, double-stranded probes, and FRET hybridization probes are suitable for that purpose. In homogeneous, real-time LATE-PCR assays, probes that target the single-stranded amplicon are present in the initial reaction mixture. During the exponential phase of the amplification such probes target the same amplicon strand as does the Limiting Primer.

A further embodiment of the invention is to use Low-$T_m$ hybridization probes. The $T_{m[0]}^P$ of Low-$T_m$ probes is equal to or below, preferably at least 5° C. below, most preferably at least 10° C. below, the $T_{m[0]}^L$ of the Limiting Primer. Low-$T_m$ Probes used in a LATE-PCR can either be detected during the annealing step of a 2 or 3 step reaction, or can be detected during a step added after the extension step and prior to the next melting step. These probes have the added benefit of being more allele discriminating than conventional hybridization probes.

A preferred embodiment of the invention uses Super-Low-$T_m$ hybridization probes. The $T_{m[0]}^P$ of a Super-Low-$T_m$ probe is at least 5° C. below, and more preferably 10° C. below the mean annealing temperature of the reaction. Super-Low-$T_m$ probes are preferably employed in LATE-PCR assays in conjunction with the novel detection step, described above, which is carried out under preferred conditions of lowered temperature to accommodate the properties of such probes. If a constant temperature is used for annealing step throughout the exponential phase of the reaction, $T_{m[0]}^P$ is at least 5° C., most preferably at least 10° C., below that temperature. If the annealing temperature is not constant during the cycles of the exponential phase of the reaction the preferred temperature in this case is at least 5° C., most preferred at least 10° C. below the mean annealing step temperature of the exponential phase of the reaction. Like Low-$T_m$ probes, Super-Low-$T_m$ probes are more allele discriminating than conventional hybridization probes.

Certain preferred embodiments utilize an added detection step in all or, preferably only some, amplification cycles. The detection step is of minimal duration, generally 10-30 seconds, sufficient for probes to hybridize and signal. We prefer to utilize this step beginning 5-10 cycles prior to the anticipated threshold cycle, $C_T$. We also prefer to utilize this added detection step following the primer-extension step. This step effectively separates primer-annealing-and-extension from probe-annealing-and-detection.

Certain preferred embodiments utilize a low temperature version of the added detection step in all or some amplification cycles, namely, a low-temperature detection step, which comprises dropping the temperature below the temperature of the previous annealing step for a time sufficient for Low-$T_m$ probes to hybridize and signal, generally 10-30 sec. We prefer to utilize this step beginning 5-10 cycles prior to the anticipated threshold cycle, $C_T$. We also prefer to utilize this added detection step to follow the extension step. In other embodiments low-temperature detection is performed after strand melting but before primer extension. After low-temperature detection the temperature is raised either to the strand-melting temperature or to the primer-extension temperature.

In preferred embodiments the probes are not hybridized to target and amplicon strands during primer annealing and primer extension, and detection is uncoupled from primer annealing. In contrast, conventional real-time PCR assays of the prior art that utilize probes that signal upon hybridization, such as molecular beacon probes, hybridize both primers and probes during the annealing step, and assays rely on a temperature rise for primer extension to remove probes but not primers from template strands.

This invention also includes sets of primers and probes for performing LATE-PCR amplifications and assays. We sometimes refer to these as "oligonucleotide sets." The set for an amplification or assay includes one or more pairs of an Excess Primer and a Limiting Primer having melting temperatures and concentration ratios as described herein. Embodiments for real-time assays further include at least one labeled hybridization probe as described herein, including for certain preferred embodiments LOW-$T_m$ hybridization probes or Super-Low-$T_m$ hybridization probes that only hybridize during the low-temperature detection step described above. An oligonucleotide set containing one primer pair may contain more than one probe, for instance, one for the wild-type sequence being amplified and one for its mutant allele. For oligonucleotide sets one can include the primers or the primers and probes in separate buffers or, as is preferred, in a single buffer to fix their concentration ratios. Oligonucleotide sets are designed according to the principles of LATE-PCR and thus have specified, or "intended" concentrations, rations and initial, concentration-adjusted melting temperatures. For example, the intended, concentration-adjusted melting temperature of the Limiting Primer should be at least equal to the intended concentration-adjusted melting temperature of the Excess Primer, and so on.

This invention also includes reagent kits for amplifications and assays. Kits for amplification include, in addition to primer sets, at least a DNA polymerase, four dNTP's and amplification buffer. Real-time homogeneous assay kits contain oligonucleotide sets that include primers and labeled hybridization probes as well as DNA polymerase, four dNTP's and amplification buffer. Kits may contain additional ingredients for sample preparation, as well as controls. Complete kits contain all reagents necessary for performing a LATE-PCR amplification or assay and, optionally, disposable materials to be used. Kits may be in one package or in multiple packages, that is, modular.

Multiplexing involves the simultaneous amplification in a single reaction vessel of two or more target sequences utilizing multiple primer pairs, one for each target. An aspect of this invention is multiplex LATE-PCR assays, kits and oligonucleotide sets. In multiplex assays it is preferred that the $T_{m[0]}^L$ of all Limiting Primers in the reaction be made equal to or greater than the $T_{m[0]}^X$ of all Excess Primers in the reaction.

It is recommended that primer candidates be subjected to computer analysis to screen out obvious cases of primer-dimer formation, as well as inappropriate product strand interactions.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 presents real-time fluorescence curves from PCR amplifications with a primer pair according to this invention and with a symmetric PCR primer pair.

FIG. 2A presents real-time fluorescence curves from PCR amplifications with primer pairs having varying values of the difference $(T_{m[0]}^L - T_{m[0]}^X)$, using a constant annealing temperature.

FIGS. 3A, 3B, 3C present real time fluorescence curves from replicate PCR amplifications with primer pairs having various $T_m$ relationships at both equal and unequal concentrations.

FIG. 6 presents real-time fluorescence curves from PCR amplifications having varying values of $(T_m^A - T_{m[0]}^X)$ with $(T_{m[0]}^L - T_{m[0]}^X)$ in the range of 0.0° C.

Like reference symbols in the various drawings indicate like elements.

DETAILED DESCRIPTION

Designing Limiting and Excess Primer Pairs

Figure 2B:
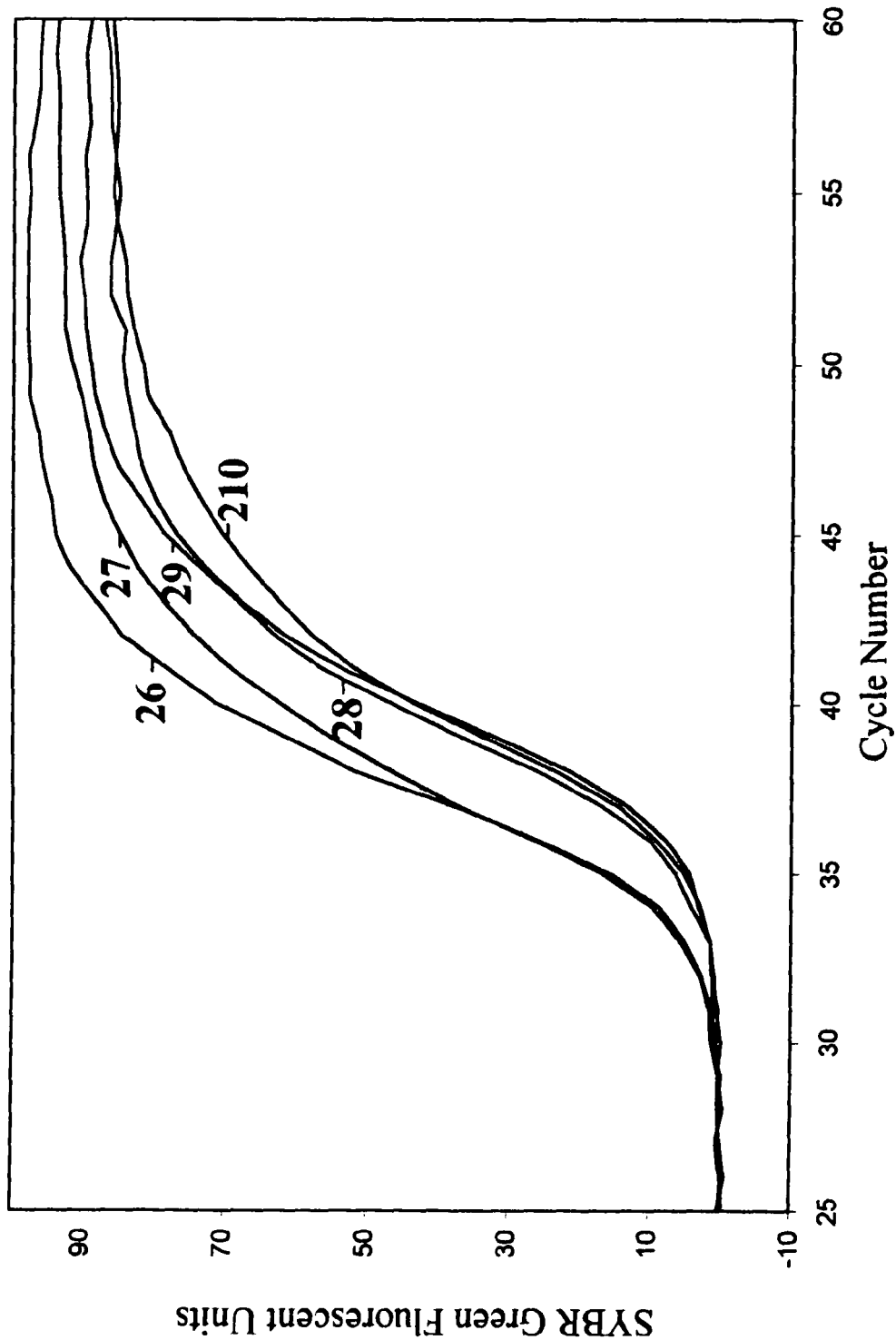
FIG. 2B presents real-time fluorescence curves from PCR amplifications with primer pairs having varying values of the difference $(T_{m[0]}^L - T_{m[0]}^X)$, and an annealing temperature relative to $T_{m[0]}^L$.

Design of primer pairs for use in this invention can be performed directly, as will be explained. Alternatively, it can begin with selecting or designing a primer pair for symmetric PCR by known methods, followed by modifications for LATE-PCR. Symmetric PCR primers are designed to have equal melting points at some set of standard conditions of primers concentration and salt concentration. Symmetric PCR primers are conveniently designed and analyzed utilizing an available computer program. For symmetric and asymmetric PCR the standard techniques for calculating melting temperatures ($T_m$) have been the "Nearest Neighbor" method and the "2(A+T)+4(G+C)" method. For clarity we introduce the concept of $T_{m[1]}$ which is the $T_m$ of the primer at a standard primer concentration of 1 µM and 0.07M salt (monovalent cations). Conversion from the $T_m$ given by a typical computer program to $T_{m[1]}$ generally has minimal effect on the relationship of the $T_m$'s of a primer pair. For the concentration-adjusted melting temperatures of primer pairs according to this invention, either actual measurement or an appropriate calculation is required. For the purpose of describing and comparing primer melting points according to this specification and claims, "concentration-adjusted melting point," or "$T_{m[0]}$", we calculate the melting point according to the Nearest Neighbor formula set forth above in the definitions used in this specification where possible; otherwise we determine $T_{m[0]}$ empirically.

In practice, once a particular target sequence (for instance a sequence flanking a mutation within a gene) has been chosen for amplification, several candidate pairs of equal $T_m$ primers are designed via a computer program such as Oligo 6.0® using the program's default values. The candidate primer pairs are then scrutinized on the basis of additional criteria, such as possible primer-dimer formation, that are known in the art to cause non-desirable primer qualities. Satisfactory pairs of candidate primers are further scrutinized using software such as "Blast" for possible non-specific matches to DNA sequences elsewhere in the known genome from the species of the target sequence (Madden, T. L. et al. (1996) "Applications of Network BLAST Server," Meth. Enzymol. 266: 131-141). Primers pairs are then compared as to their $T_{m[0]}$ values at several different possible concentrations and ratios such that the primer chosen to be the Limiting Primer will have an equal or greater $T_{m[0]}$ relative to the primer chosen to be the Excess Primer. In addition, pairs of candidate primers are examined in relation to the sequence of the amplicon they are expected to generate. For instance, certain target sequences may contain a GC-rich sequence at one end and a less GC-rich sequence at the other end. Where that occurs, choosing the Limiting Primer sequence within sequences at the GC-rich end will assist in achieving a higher melting point for the Limiting Primer relative to the Excess Primer, which will consists of sequences in the less GC-rich end. Examination of the candidate primer pairs relative to the amplicon sequence may suggest additional or novel ways of modifying the sequences of one or both members of the pair, such as deliberately increasing or decreasing the length of the primer, most preferably at its 5' end, or introducing changes in base sequences within the primer which deliberately cause it to mismatch with its target in small regions. All such changes will increase or decrease the $T_{m[0]}$ of either the Limiting or Excess primer.

Table I illustrates two possible primer pairs for one allele in the HEX-A gene which is responsible for Tay-Sachs disease, as well as the LATE-PCR criterion used to judge whether or not they were likely to be suitable for LATE-PCR. In accord with the theoretic principles of LATE-PCR, the experimental assay discussed below in connection with FIG. 1 established that only the primer pair for which $(T_{m[0]}^L - T_{m[0]}^X) \geq 0$ (i.e., primer set 2, Table I) was suitable for LATE-PCR. In comparing the two primer sets, it will be noted that the Limiting Primer in Set 2 has two additional 5' nucleotides as compared to its corresponding primer in Set 1. The Excess Primer is the same in both sets.

TABLE I

Possible primers pairs and the LATE-PCR criterion for their selection

| | Sequence | SEQ ID NO: | Conc. | $T_{m[1]}$ | Conc. | $T_{m[0]}$ | (Tphd m[0]$^L$ − m[0]$^X$) |
|---|---|---|---|---|---|---|---|
| Primer Set 1 | | | | | | | |
| TSD1242S20 | 5'-CCTTCTCTCTGCCCCCTGGT-3' | 1 | 1 µM | 64.8° C. | 25 nM | 58.9° C. | −5 |
| TSD1301A22 | 5'-GCCAGGGGTTCCACTACGTAGA-3' | 2 | 1 µM | 64.3° C. | 1 µM | 64.3° C. | |
| Primer Set 2 | | | | | | | |
| TSD1240S22 | 5'-GCCCTTCTCTCTGCCCCCTGGT-3' | 3 | 1 µM | 69.4° C. | 25 nM | 64.0° C. | 0 |
| TSD1301A22 | 5'-GCCAGGGGTTCCACTACGTAGA-3' | 2 | 1 µM | 64.3° C. | 1 µM | 64.3° C. | |

As explained above, in the case of LATE-PCR $T_{m[1]}^L$ must be greater than $T_{m[1]}^X$ in order to guarantee that actual melting temperature of the Limiting Primer is greater than or equal to the actual melting temperature of the Excess Primer at the actual primer concentrations in the reaction, i.e. $(T_{m[0]}^L - T_{m[0]}^X) \geq 0$. If this condition is not met, i.e. $(T_{m[0]}^L - T_{m[0]}^X) < 0$, amplification reactions run inefficiently. These features of LATE-PCR are illustrated in FIG. 1, which shows real-time LATE-PCR reactions with the primer pairs of Table I in which the double-stranded products synthesized during the exponential phase of the reaction have been visualized using SYBR® Green. Curve 12 shows the efficient reaction (product detected in fewer thermal cycles), $(T_{m[0]}^L - T_{m[0]}^X) = 0$ and $(T_{m[1]}^L - T_{m[1]}^X) = 5$, while curve 11 shows the inefficient reaction (product detected in more thermal cycles), $(T_{m[0]}^L - T_{m[0]}^X) = -5$ and $(T_{m[1]}^L - T_{m[1]}^X) = 1$. Both reactions amplified the same region of the HEX-A gene and both were initiated with 1000 genomes. In the case of curve 12, $T_{m[1]}^L = 69°$ C. and $T_{m[1]}^X = 64°$ C., while in the case of Curve 11, $T_{m[1]}^L = 64$ while $T_{m[1]}^X = 64°$ C. (see Table I). The design and execution of this experiment are described in detail in Example 1.

FIG. 2A, based on the pairs of primers described in Example 3, illustrates the fact that as $T_{m[1]}^L$ is increased several degrees above $T_{m[1]}^X$, $(T_{m[0]}^L - T_{m[0]}^X)$ becomes >0 and the efficiency of the LATE-PCR increases still further. Each of the curves in FIG. 2A shows the mean real time fluorescence increase in samples with $(T_{m[0]}^L - T_{m[0]}^X) = +7$ (curve 21), +5 (curve 22), +3 (curve 23), 0 (curve 24), and −3 (curve 25). Each curve depicts the average fluorescence of 3 replicate samples. The earliest detection (lowest mean $C_T$ value) was obtained using the primer pair with the highest value $(T_{m[0]}^L - T_{m[0]}^X)$, curve 21. Mean $C_T$ values increased with each decrease in the value of $(T_{m[0]}^L - T_{m[0]}^X)$. Lower $C_T$ values demonstrate a higher rate of amplification (i.e., increased efficiency) during the exponential phase of the reaction. Experimental details about this experiment are provided below in Example 3. Example 3 (and FIG. 2B therein)

also describe an additional experiment illustrating that the efficiency and specificity of the LATE-PCR improves when $(T_{m[0]}^L - T_{m[0]}^X)$ becomes >0.

Figure 3B:
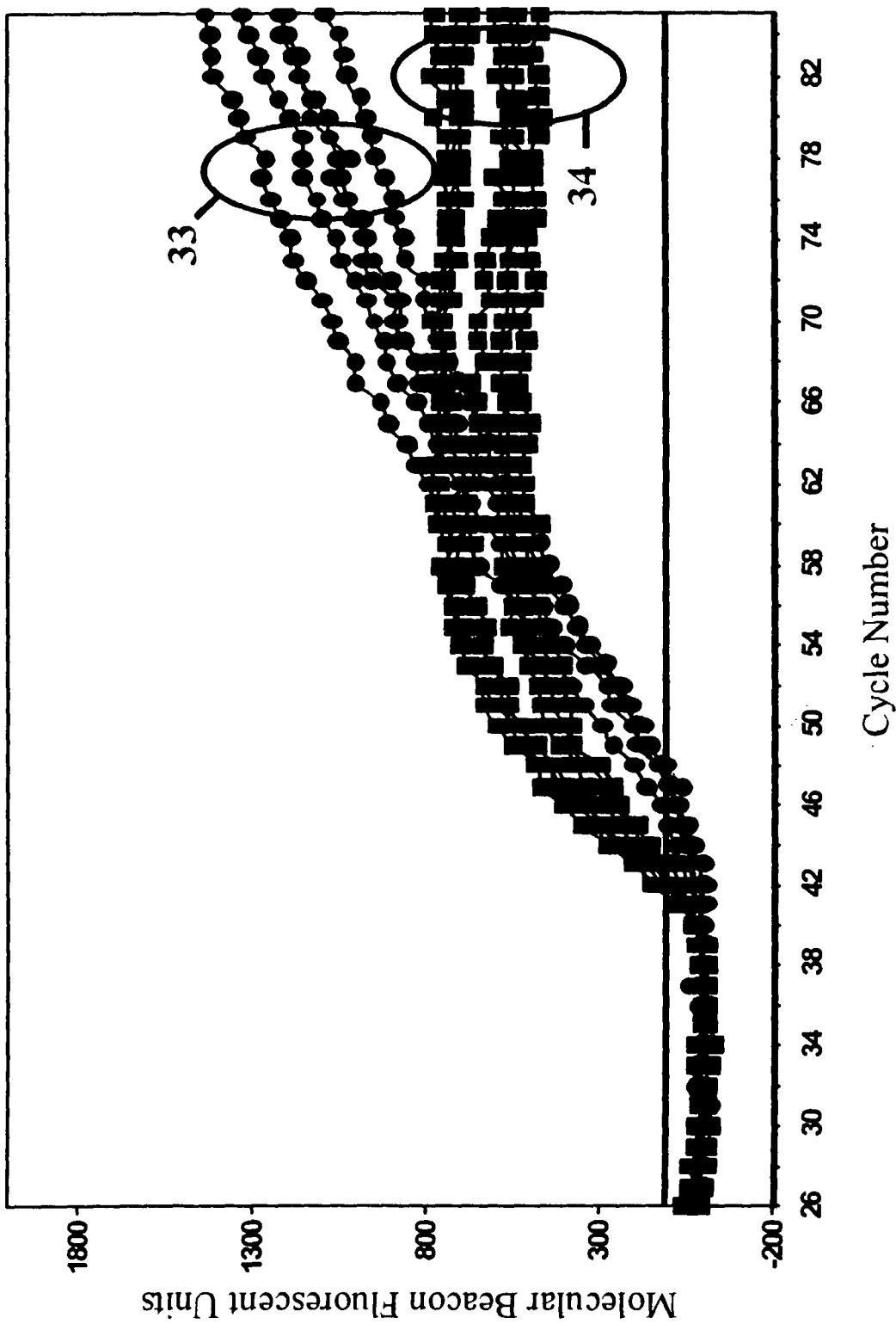
Figure 3C:
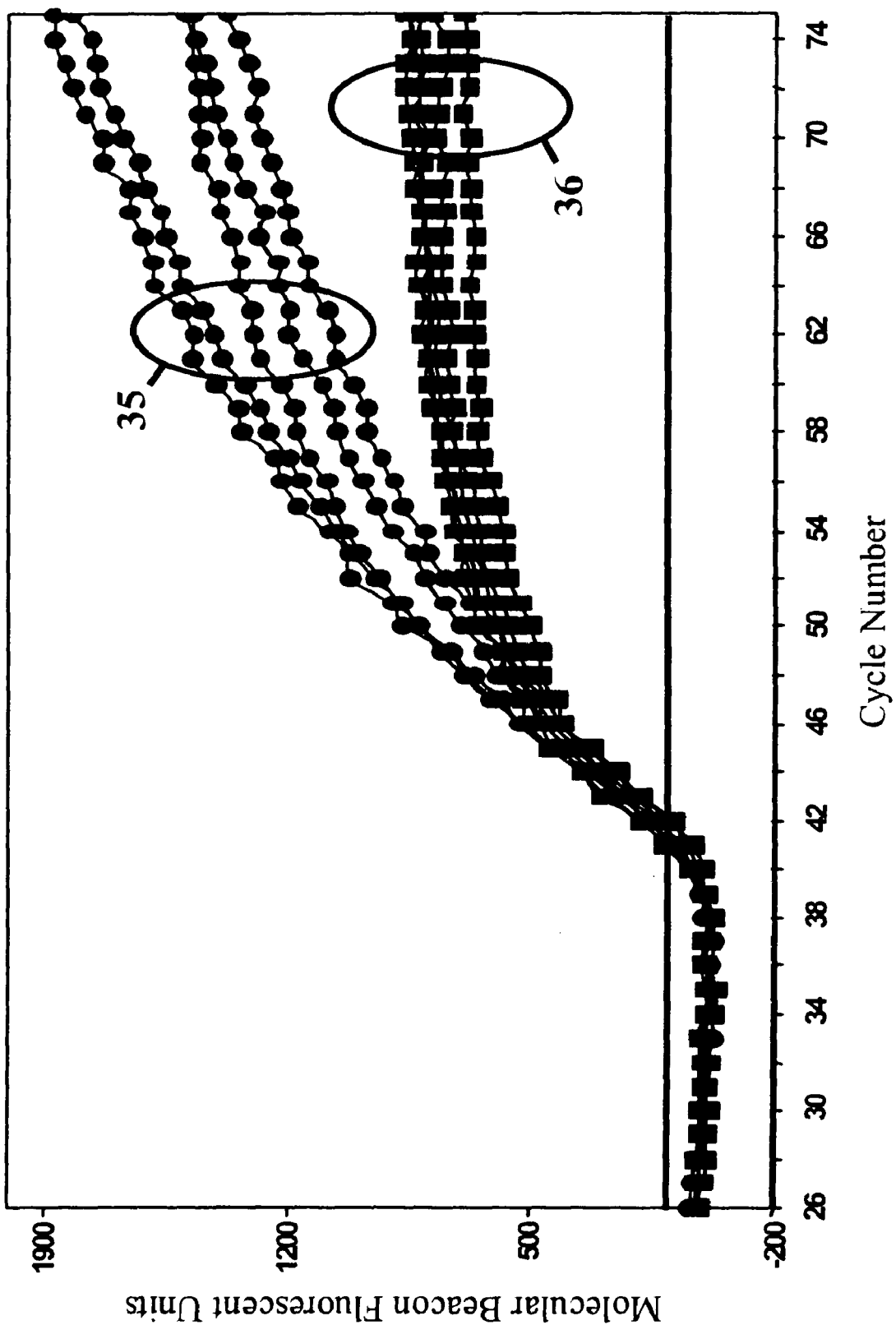

FIGS. 3A-3C show examples of amplification using three different CFTR primer sets. The experimental details of FIG. 3 are described in Example 4. The primers were either equimolar (both at 500 nM; curves 32, 34, and 36) or present at a 1:10 ratio (50 mM Limiting Primer:500 nM Excess Primer; curves 31, 33, and 35). All experiments used a molecular beacon probe that monitored synthesis of the Excess Primer strand of the amplicon for the cystic fibrosis ΔF508 allele. $T_m$ values for the primers were initially obtained using the default parameters of the Oligo® 6.0 program. Based on this program the equimolar $T_m$ values of the primers used in FIG. 3 were as follows: FIG. 3A both primers 65° C.; FIG. 3B Limiting Primer 70° C. and Excess Primer 65° C.; FIG. 3C Limiting primer 75° C. and Excess primer 65° C.

As shown in FIG. 3A, the asymmetric reaction (1:10 primer ratio, curve 31) using the two primers with the same $T_m$'s results in a fluorescence signal that is delayed (higher $C_T$), as compared to the symmetric reaction (equimolar primers, curve 32). However, when a 5° C. difference in $T_m$'s is introduced (FIG. 3B), the $C_T$ for the primers with a 1:10 ratio (curve 33) occurs much earlier, almost as early as for the equimolar primers (curve 34). Additionally, the final fluorescence signal for the primers with a 1:10 ratio (curve 33) is much higher than the signal for the equimolar primers (curve 34), and it has not plateaued, even beyond 60 cycles. When a 10° C. difference in $T_m$'s (FIG. 3C) is introduced, the $C_T$ for the primers with a 1:10 ratio (curve 35) is the same as for the equimolar primers (curve 36), and the final fluorescence is much higher and does not plateau.

Figure 4A:
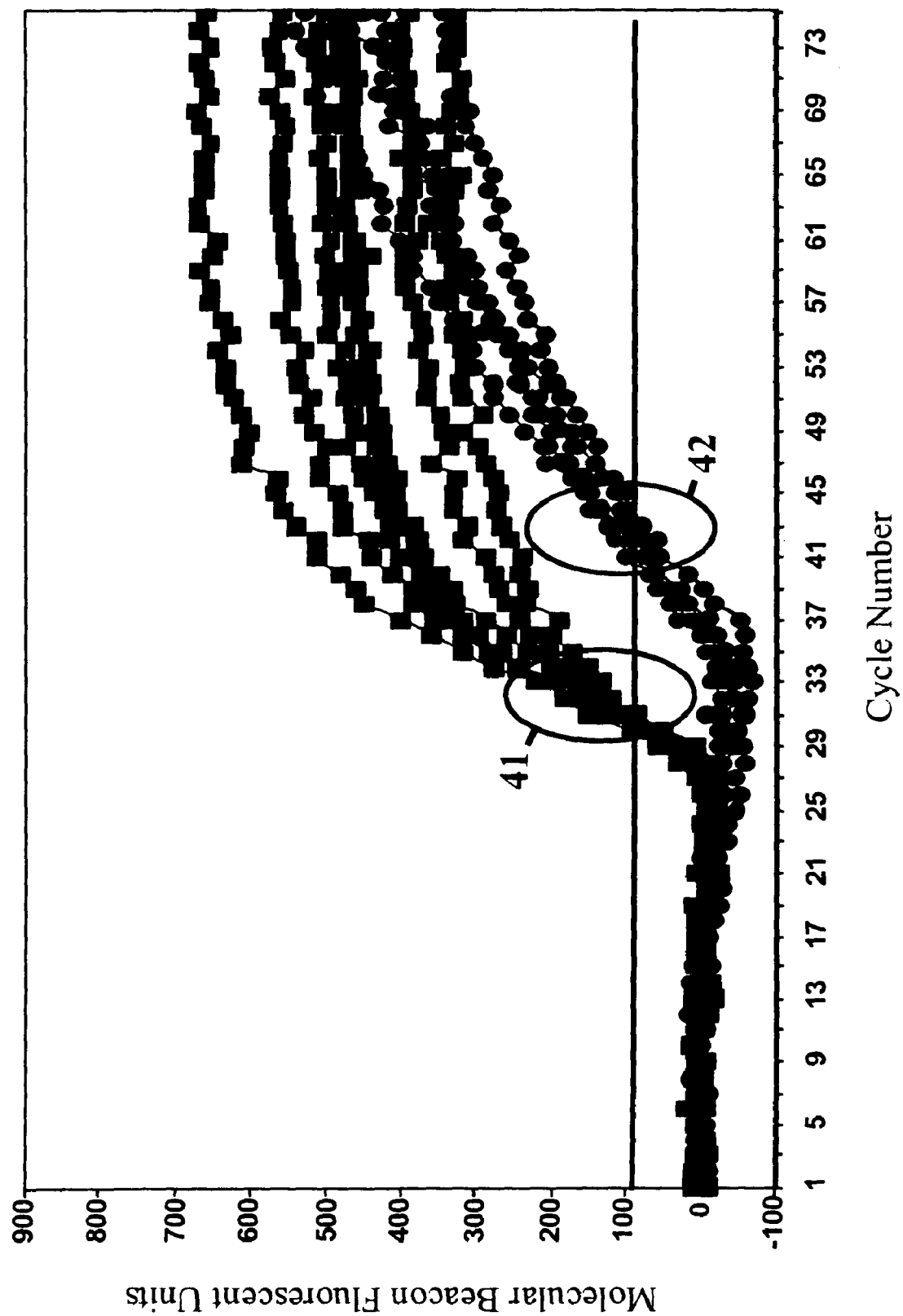
FIGS. 4A, 4B present real-time fluorescence curves from replicate PCR amplifications with primer pairs having different $T_m$ relationships at both equal and unequal concentrations.
Figure 4B:
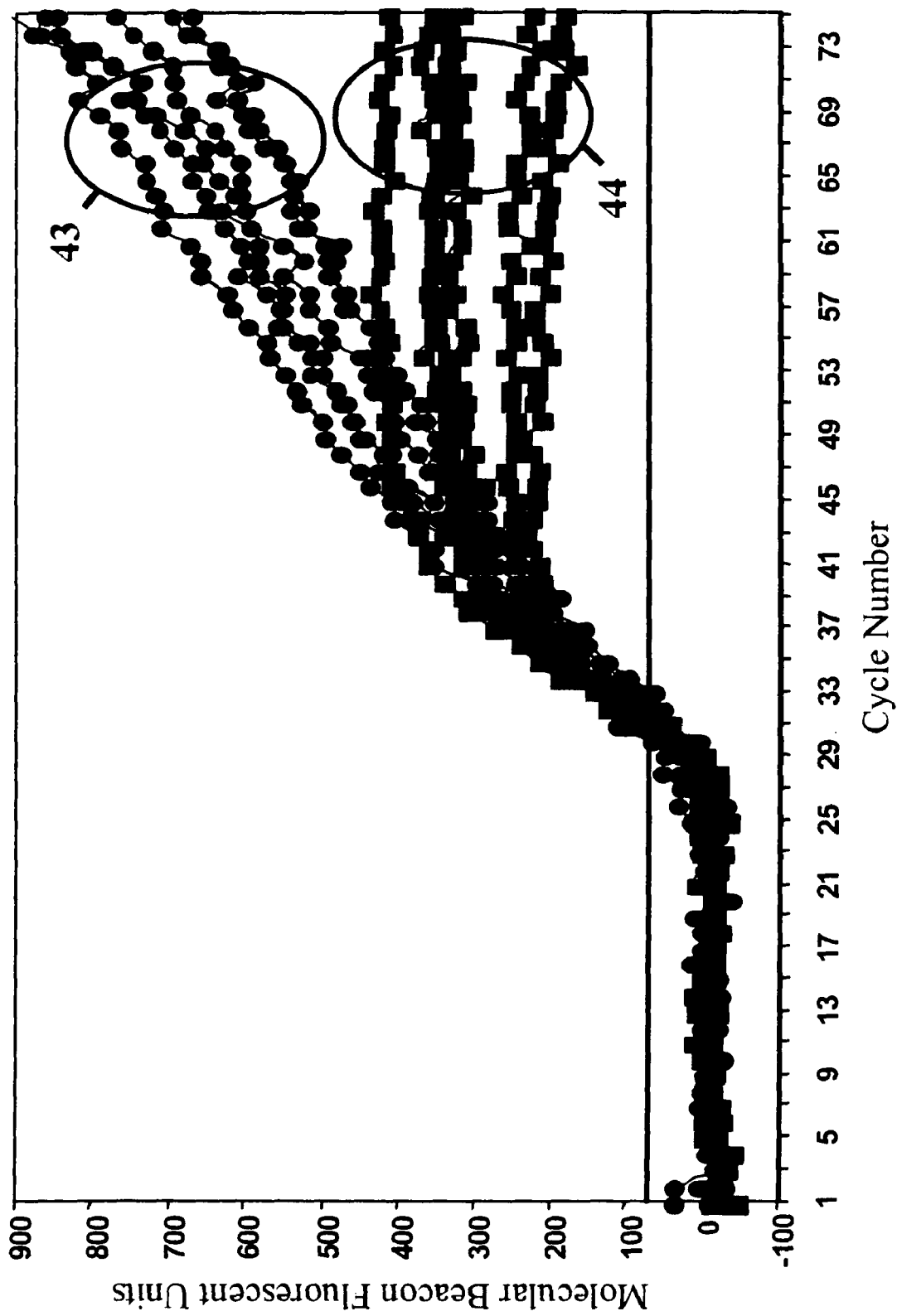

FIGS. 4A-4B show a similar example using two sets of primers for the Tay-Sachs Disease, HEX-A gene. In this case the primers were either equimolar (both 300 nM; curves 41 and 44) or present at a 1:100 ratio (10 nM Limiting Primer; 1000 nM Excess Primer; curves 42 and 43). All experiments used a molecular beacon probe that monitored synthesis of the single-stranded product of the Excess Primer for the normal allele of the HEX-A gene, in the region of the gene that includes 1278-disease causing allele. Once again, the $T_m$ values from the primers were initially obtained using the default parameters of the Oligo® 6.0 program. Based on this program the equimolar $T_m$ values of the primers used in FIG. 4 were as follows: FIG. 4A both primers 72° C.; FIG. 4B Limiting Primer 84° C. and Excess Primer 72° C.

Once again, the asymmetric reaction (1:100 primer ratio, curve 42) using equal $T_m$ primers (as calculated by the default values of the Oligo® 6.0 program) results in a fluorescence signal that is delayed (higher $C_T$), as compared to the symmetric reaction (equimolar primers, curve 42, FIG. 4A). However, when a 12° C. difference in $T_m$'s is introduced (FIG. 4B), the $C_T$ for the primers with a 1:100 ratio (curve 43) is the same as for the equimolar primers (curve 44), and the final fluorescence is much higher and does not plateau.

Application of the "Nearest Neighbor" formula allows the default $T_m$ values obtained from the Oligo® 6.0 software to be converted into $T_{m[0]}$ values that take the actual starting concentration of each primer into account, as shown in Table II. The $T_m$ values calculated by Oligo 6.0 are useful only as a rough approximation, since they are based on the thermodynamic values and salt correction factors of Breslauer et al. (Breslauer K J et al., (1986) "Predicting DNA Duplex Stability From The Base Sequence, "Proc. Natl. Acad. Sci. USA 83: 3746-50), and are relatively inaccurate (Owczarzy R, et al., (1998) "Predicting Sequence-Dependent Melting Stability of Short Duplex DNA Oligomers," Biopolymers 44: 217-39; SantaLucia J. (1998) "A Unified View of Polymer, Dumbbell, and Oligonucleotide DNA Nearest-Neighbor Thermodynamics," Proc. Natl. Acad. Sci. USA 95: 1460-5). The resulting data fully account for the results shown in FIGS. 3 and 4 in terms of the principles of LATE-PCR. Only the reactions illustrated in FIGS. 3C and 4B meet the requirement that $(T_{m[0]}^L - T_{m[0]}^X) \geq 0$, and therefore are LATE-PCR reactions. Only these reactions have the lowest $C_T$ values and highest final fluorescence signals and do not plateau like reactions utilizing equimolar primers. In contrast, the conventional asymmetric reactions in FIGS. 3A, 3B, and 4A have $(T_{m[0]}^L - T_{m[0]}^X) < 0$. These reactions are inefficient (higher $C_T$ values and lower fluorescence).

TABLE II $T_{M[0]}$ values for the CFTR and HEX-A primers in FIGS. 3 and 4

| Primers | Sequence | SEQ ID NO: | Primer ratio (equal) | | Primer ratio (unequal) | | Criteria $(T_{m[0]}^L - T_{m[0]}^X)$ |
| --- | --- | --- | --- | --- | --- | --- | --- |
| | | | (nM) | (° C.) | (nM) | (° C.) | |
| FIG. 3A | | | | | | | |
| CF403S18 | 5'GATTATGCCTGGCACCAT3' | 4 | 500 | 55.0 | 50 | 52.5 | -3.0 |
| CF482A23 | 5'CTTTGATGACGCTTCTGTATCTA3' | 5 | 500 | 55.5 | 500 | 55.5 | |
| FIG. 3B | | | | | | | |
| CF402S19 | 5'GGATTATGCCTGGCACCAT3' | 6 | 500 | 57.9 | 50 | 54.1 | -1.4 |
| CF482A23 | 5'CTTTGATGACGCTTCTGTATCTA3' | 5 | 500 | 55.5 | 500 | 55.5 | |
| FIG. 3C | | | | | | | |
| CF399S22 | 5'CCTGGATTATGCCTGGCACCAT3' | 7 | 500 | 62.8 | 50 | 59.5 | +4.0 |
| CF482A23 | 5'CTTTGATGACGCTTCTGTATCTA3' | 5 | 500 | 55.5 | 500 | 55.5 | |
| FIG. 4A | | | | | | | |
| TSD1242S20 | 5'-CCTTCTCTCTGCCCCCTGGT3' | 1 | 300 | 62.8 | 10 | 58.9 | -5.4 |
| TSD1301A22 | 5'-GCCAGGGGTTCCACTACGTAGA-3' | 2 | 300 | 62.6 | 1000 | 64.3 | |

TABLE II-continued

T$_{M[0]}$ values for the CFTR and HEX-A primers in FIGS. 3 and 4

| Primers | Sequence | SEQ ID NO: | Primer ratio (equal) (nM) | (° C.) | Primer ratio (unequal) (nM) | (° C.) | Criteria ($T_{m[0]}^{L}$-$T_{m[0]}^{X}$) |
|---|---|---|---|---|---|---|---|
| FIG. 4B | | | | | | | |
| TSD1238S20 | 5'CCGCCCTTCTCTCTGCCCCCTGGT3' | 8 | 300 | 71.2 | 10 | 66.7 | +2.4 |
| TSD1301A22 | 5'-GCCAGGGGTTCCACTACGTAGA-3' | 2 | 300 | 62.6 | 1000 | 64.3 | |

Figure 5A:
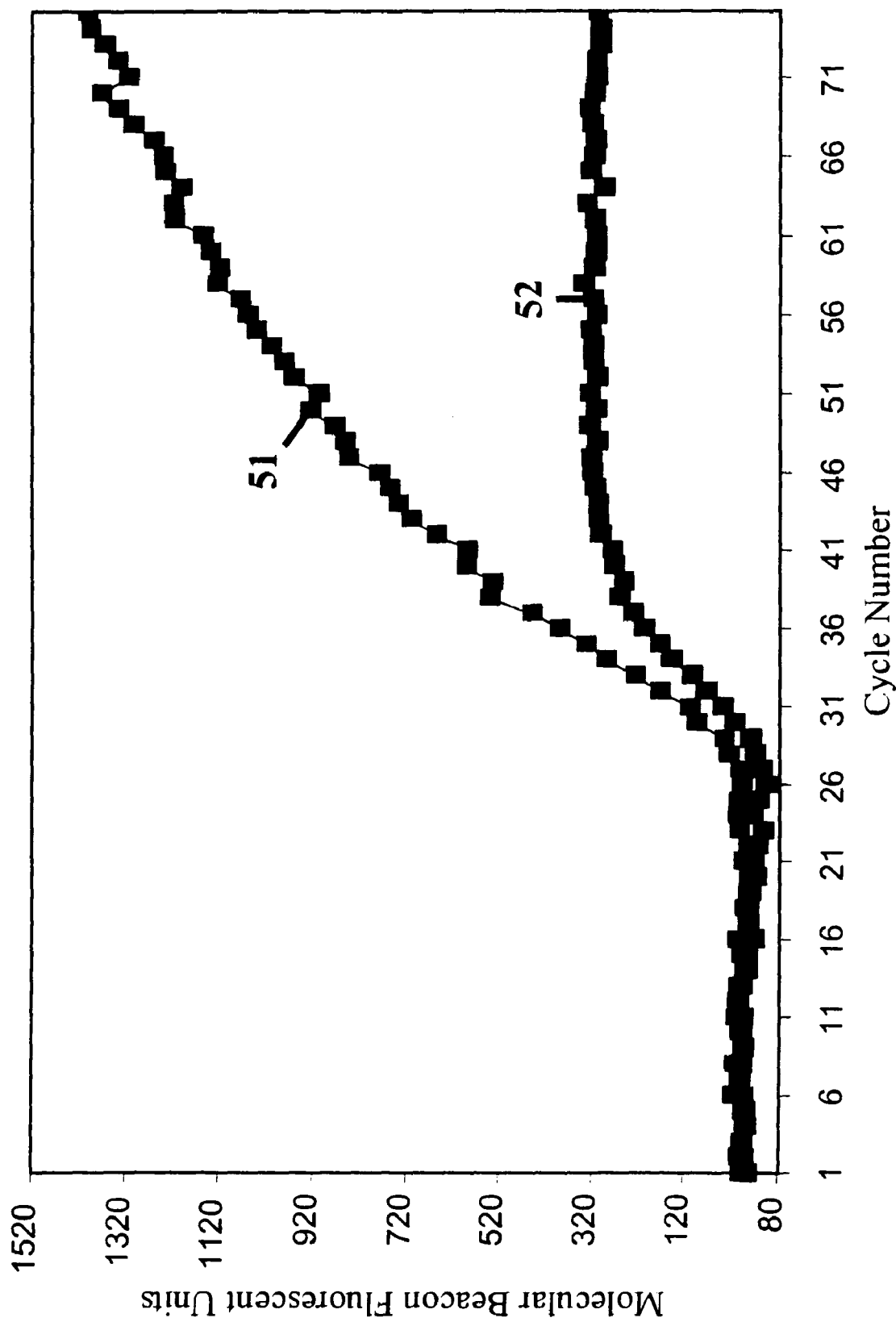
FIGS. 5A, 5B, 5C present real-time fluorescence curves from PCR amplifications having primer pairs having different $T_m$ relationships at several concentration ratios.
Figure 5B:
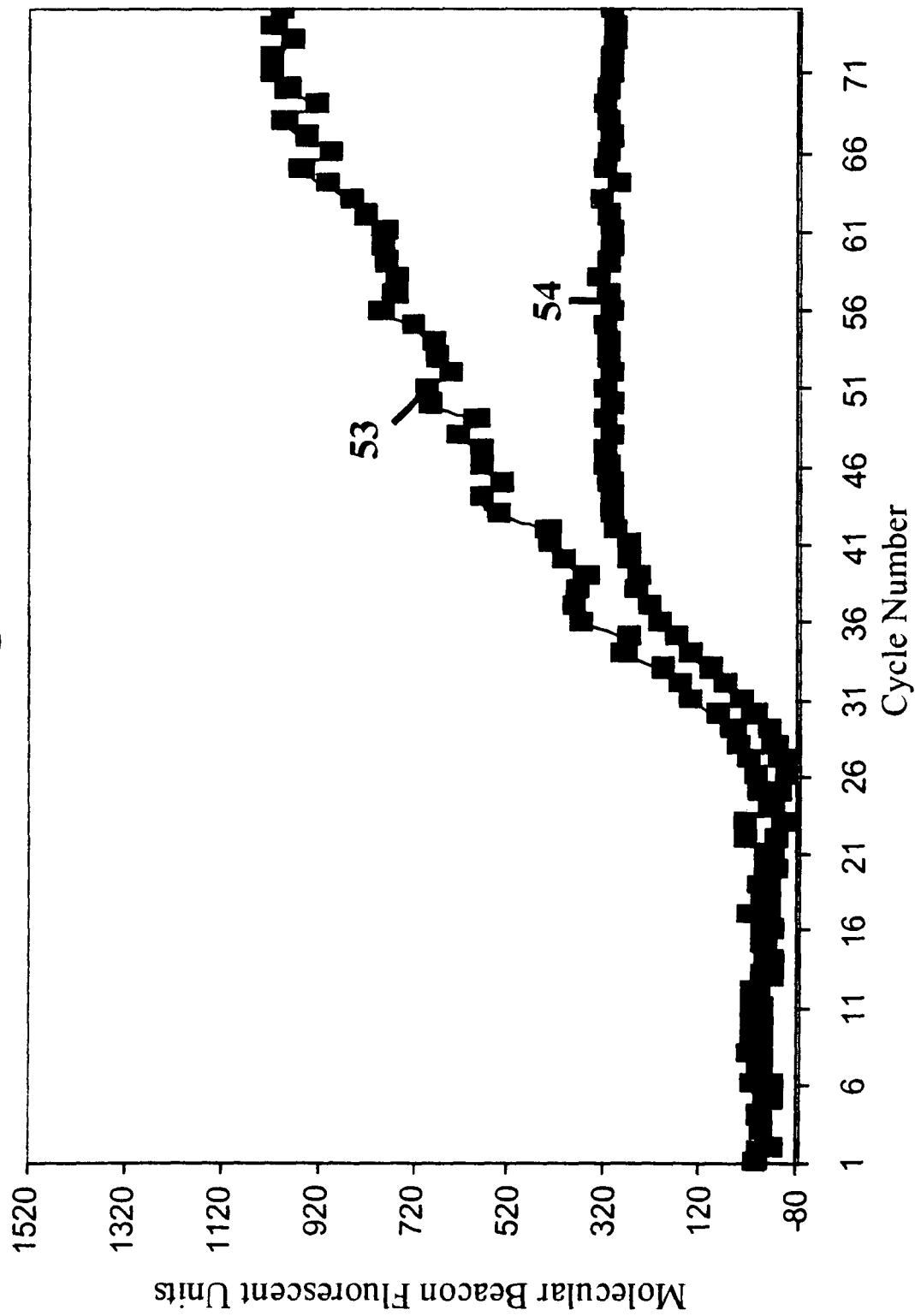
Figure 5C:
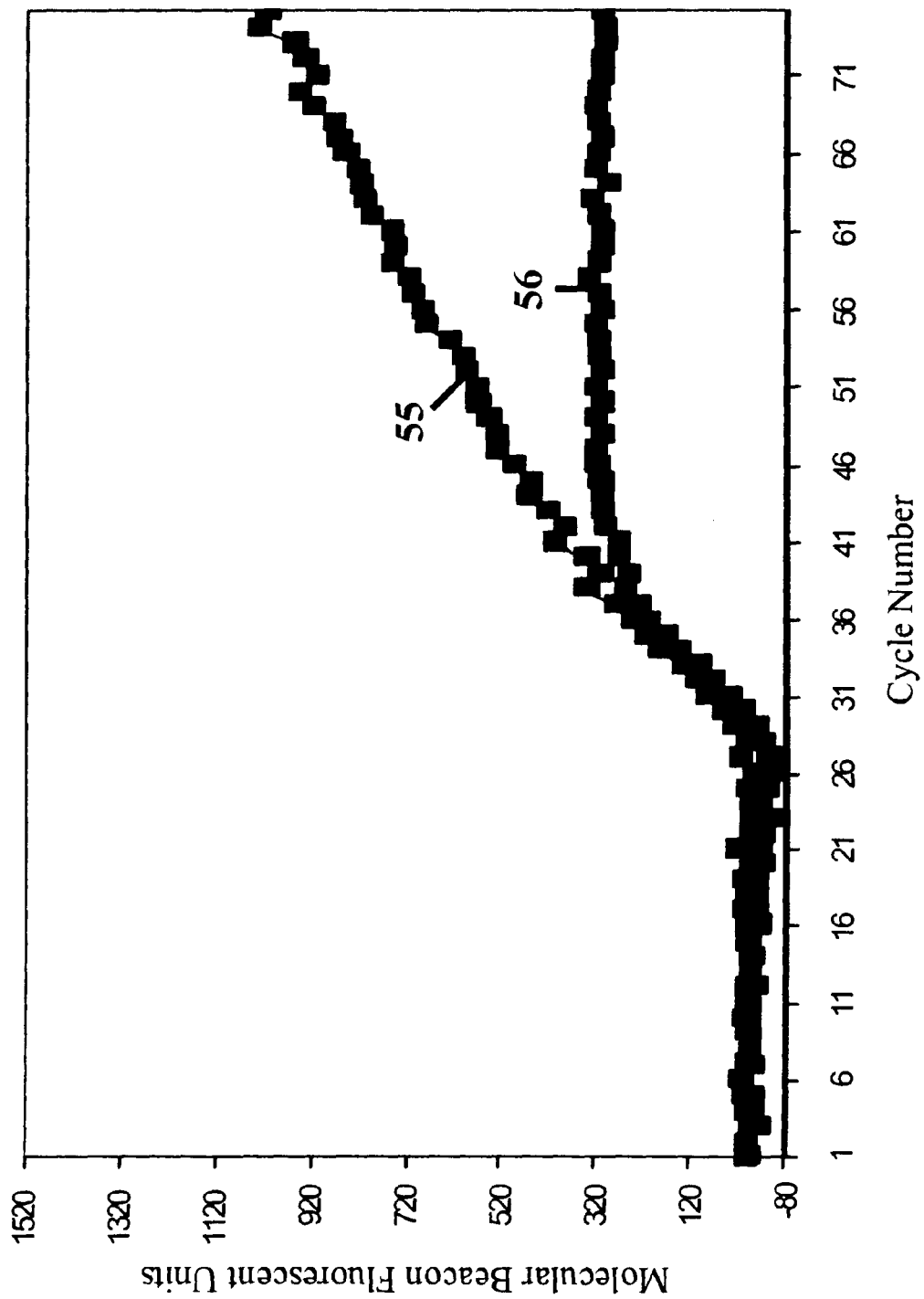

FIGS. 5A-5C illustrate that well-designed LATE-PRC primers generate efficient reactions over a wide range of Limiting Primer to Excess Primer ratios. In this case, the HEX-A primers used in FIG. 4B were prepared at three different ratios: 1:10, 1:40, 1:100. The starting concentration of the Excess Primer was held constant (at 1000 nM) in each case, while the starting concentration of the Limiting Primer decreased (from 100 mM to 25 nM to 10 nM). The efficiencies and kinetics of these assays (curves 51, 53, and 55, respectively) were compared to an assay containing equimolar concentrations of the same two primers (500 nM:500 nM, curves 52, 54, and 56). Each assay was performed in replicate (5 reactions each) and the averages of these replicates are shown in FIGS. 5A-5C. The results show that all three LATE-PCR reactions (curves 51, 53, and 55) were efficient, i.e. had $C_T$ values equivalent or slightly lower than the symmetric PCR assay (curves 52, 54, 56), and they did not plateau while the symmetric reaction did. Analysis of the primer sets used in FIG. 5 is provided in Table III and explains these results in terms of the principles of LATE-PCR. All three asymmetric reactions in FIG. 5 (curves 51, 53, and 55) have $(T_{m[0]}^{L}-T_{m[0]}^{X})\geq 0$:

TABLE III

Comparison of ($T_{m[0]}^{L}$ - $T_{m[0]}^{X}$) for different ratios of primers

| Primer Set | Primer Ration | Primer Conc. (nM) | $T_{m[0]}$ (° C.) | ($T_{m[0]}^{L}$ - $T_{m[0]}^{X}$) |
|---|---|---|---|---|
| TSD1238S20 | 1:10 | 100 | 69.8 | +5.5 |
| TSD1301A22 | | 1000 | 64.3 | |
| | 1:40 | 25 | 67.9 | +3.6 |
| | | 1000 | 64.3 | |
| | 1:100 | 10 | 66.7 | +2.4 |
| | | 1000 | 64.3 | |

Designing the Excess Primer in Relation to the Amplicon

LATE-PCR, in contrast to most conventional symmetric and asymmetric PCR, also takes the melting point of the amplicon, $T_m^A$, into account, particularly as it relates to the concentration-adjusted melting point of the Excess Primer. Because amplicons are almost always greater than 50 nucleotides long, we calculate the $T_m^A$ of the amplicon by the "% GC" method, see above. While other mathematical formulas or even other means, such as trial and error, can be used for design of primers according to this invention, melting-point relationships described herein are analyzed using the formulas given above. These formulas are useful both for design and evaluation despite the fact that they do not consider the concentration of magnesium ion (Mg$^{++}$), which is almost universally included in PCR reaction mixtures in concentrations from 1 to 5 mM, and affects the melting points of primers and amplicons. Example 5 describes our design of different primer pairs taking $T_m^A$ into account, as well as certain primer properties that we prefer.

For any chosen DNA target (for instance the sequence flanking a mutation in a particular gene) $T_m^A$ is usually similar for candidate pairs of Limiting and Excess Primer. For this reason the approximate size of the amplicon (and approximate location of the primers) is chosen first, establishing the approximate $T_m^A$. Several possible Excess Primers are selected next, such that $(T_m^A-T_{m[0]}^X)$ is within the preferred range of 7-18° C., more preferably 7-15° C., for amplifications, or 7-25° C., more preferably 7-18° C. and most preferably 7-18° C., for real-time assays. Once a set of possible Excess Primers has been selected, the sequence of the target is examined for the presence of possible GC-rich sequences at which to design candidate Limiting Primers. Several possible Limiting Primers are next designed for a range of possible Excess/Limiting primer ratios, with the goal of making sure that $(T_{m[0]}^{L}-T_{m[0]}^{X})\geq 0$.

FIG. 6 shows a set of such reactions in which $(T_{m[0]}^{A}-T_{m[0]}^{X})$ is varied from +7 to +19° C., and $(T_{m[0]}^{L}-T_{m[0]}^{X})$ is specifically set to zero. The experimental details for these data are described in Example 5. Each curve represents the average increase in molecular beacon fluorescence of 3 replicate samples. Assays with $(T_m^A-T_{m[0]}^X)=12$ (curve 61) yielded the strongest beacon signal (i.e., the largest quantity of single-stranded CFTR product) in this series. Samples with $(T_m^A-T_{m[0]}^X)=19$ (curve 65) yielded the lowest signal. Samples with intermediate values of $(T_m^A-T_{m[0]}^X)=14$ (curve 62), or 16 (curve 64) yielded intermediate average signal intensity corresponding with that value. Samples with $(T_m^A-T_{m[0]}^X)=7$ (curve 63) also yielded intermediate final signal intensity.

Figure 7:
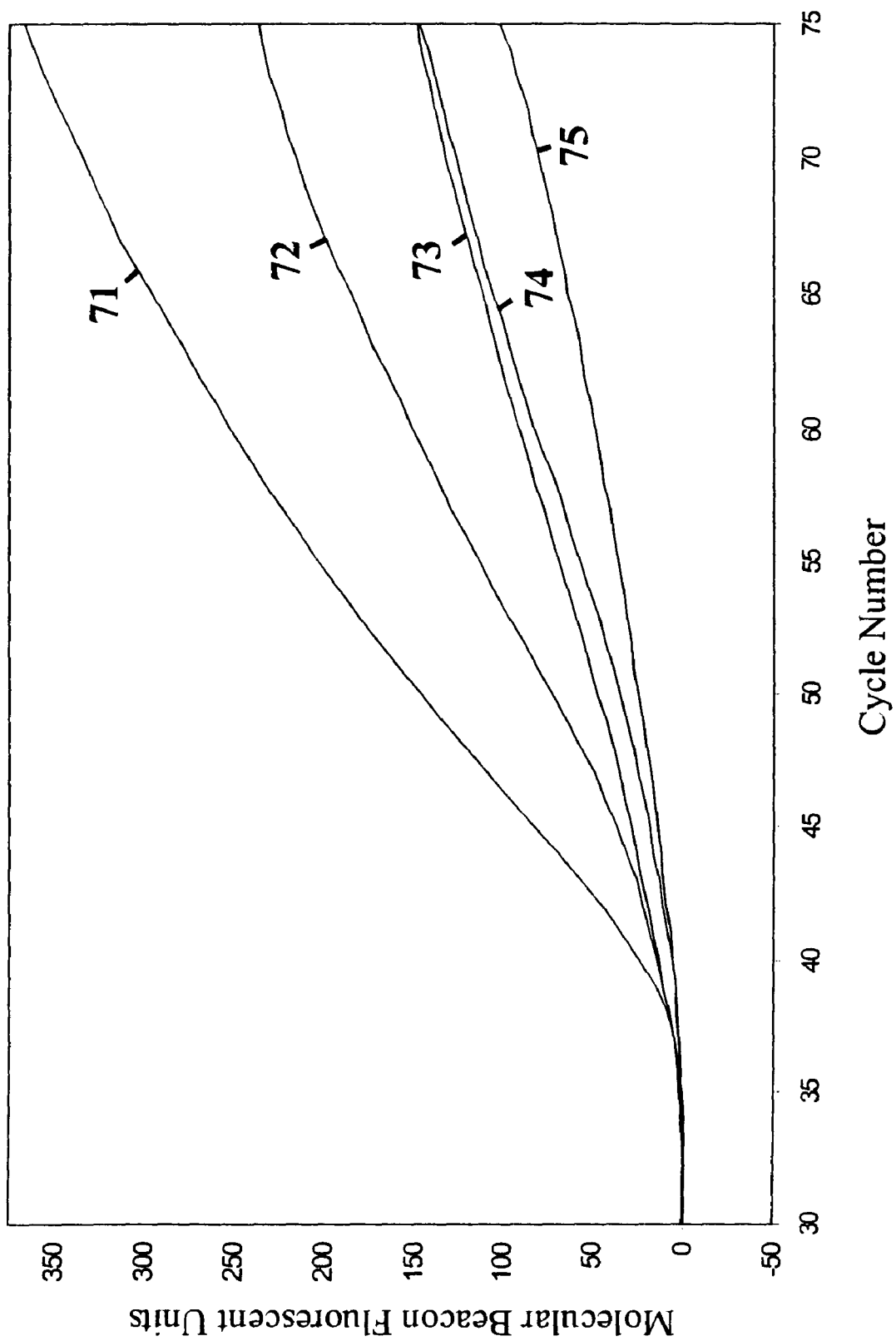
FIG. 7 presents real-time fluorescence curves from PCR amplifications having varying values of $(T_m^A - T_{m[0]}^X)$ with $(T_{m[0]}^L - T_{m[0]}^X)$ in the range of 5-6° C.

FIG. 7 illustrates several real-time reactions in which $(T_m^A-T_{m[0]}^X)$ varies from +13 to +23° C. and $(T_{m[0]}^{L}-T_{m[0]}^{X})=$5-to-6° C. in all cases, (Example 5 Table IX). The highest mean molecular beacon signal (cycles 35-60) were in samples with $(T_m^A-T_{m[0]}^X)=13$ (curve 71), indicating efficient single strand synthesis. The mean intensity of the molecular beacon signal decreased with each increase in $(T_m^A-T_{m[0]}^X)$ to values of 17 (curve 72), 19 (curve 73), 20 (curve 74), and 23 (curve 75). None of these samples showed an amplification plateau, illustrating another advantage of having $(T_{m[0]}^{L}-T_{m[0]}^{X})\geq 5°$ C. Electrophoresis of these samples revealed only the specific single- and double-stranded amplicon. Experimental details of the data in FIG. 7 are provided in Example 5.

Primers for amplifications and assays according to this invention may utilize universal primer sequences added to the 5' end of one or both primers of a pair. Universal priming sequences have particular utilities, such as introduction of specific restriction enzyme sequences, or to enhance multiplexing. A universal priming sequence included in a Limiting Primer will not raise its melting temperature with the intended target during the initial cycles of amplification, when specificity is particularly crucial, but it will raise its melting temperature thereafter due to the generation of amplicons containing sequences complementary to the universal priming sequence. While the annealing temperature during the first few, generally 5-10, cycles may be lowered to improve efficiency when the Limiting Primer contains a universal sequence addition, care must be taken not to incur non-specific amplification due to non-specific hybridization of the Excess Primer that may result. In some instances it may be preferable to sacrifice efficiency during the first few cycles by using a higher annealing temperature according to the $T_m$ of the portion of the primer that is complementary to the starting targets. If a universal priming sequence is added to the Excess Primer, there will be a similar melting point increase after the first few cycles, which will reduce the melting-point difference between the two primers. If a universal priming sequence is added to the Limiting Primer, or any other mismatch is introduced into the Limiting Primer, such that the Limiting Primer does not perfectly hybridize along its entire length to its initial target, the concentration-adjusted melting point of the entire primer, $T_{m[0]}^L$, is designed to be greater than or equal to the concentration-adjusted melting point of the Excess Primer $T_{m[0]}^X$, with the added proviso that the functional concentration-adjusted melting point of the portion of the Limiting Primer to its initial target sequence is not more than 5° C. lower than, and preferably at least equal to, the concentration-adjusted melting point of the Excess Primer. Primers useful in this invention may contain modified nucleotides, by which we mean generally nucleotides different from the four natural dNTPs. Such nucleotides may affect primer melting point. If a mathematical formula cannot be located for the effect of a particular modified nucleotide, the concentration-adjusted melting point, $T_{m[0]}$, can be determined empirically.

Protocol for Optimizing the Absolute Concentration of the Limiting Primer and Excess Primer.

In real-time LATE-PCR assays it is desirable for the Limiting Primer to be depleted at about the same thermal cycle that the double-stranded product of the reaction first becomes detectable above background, the $C_T$ value of the reaction. As is known in the art, the cycle at which the $C_T$ value is reached depends, among other things, on the amount of the target DNA present at the start of the reaction, the efficiency of amplification, the nature of the detection equipment, and the intensity of the signal (usually a fluorescent or electrical signal) generated by the hybridization probe. In LATE-PCR one of the primers is depleted after about 15-35 PCR cycles, after which linear amplification of one strand takes place during subsequent cycles utilizing the Excess Primer. In order to maximize the amount of single stranded product it is useful to optimize the absolute amount of the Limiting Primer for any chosen ratio of primers. In practice, it is also desirable to avoid Limiting Primer concentrations that exceed 200 nM. Above this concentration, the prolonged exponential phase of the reaction may produce a ratio of double-stranded to single-stranded product that is unacceptable for some applications, and may actually reduce the total amount of single-stranded product generated. Also, at a ratio of 10:1 or higher the Excess Primer concentration would be pushed above 2000 nM. Under these conditions it is difficult to avoid non-specific initiation of amplification.

The preferred concentration of Limiting Primer depends mainly on the general nature of the probe (e.g., the intensity of fluorescence from the hybridized vs. the unhybridized state), the sensitivity of the detection equipment, and the ability of the specific probe to hybridize to its target at the detection temperature. The Limiting Primer concentration needed is less dependent on the initial target concentration, since the increased target numbers will simply exhaust the Limiting Primer at an earlier thermal cycle, at which the probe signal becomes detectable.

One method for choosing the concentration of Limiting Primer that yields the desired transition from exponential to linear amplification is through empirical determination. First, several Limiting Primer/Excess Primer pairs are designed for testing one or more primer ratios (e.g., 1 to 20). Next, each of the primer pairs is empirically tested at several annealing temperatures, annealing times, and/or magnesium concentrations to determine which pair of primers and which conditions generate the intended specific amplicon with highest efficiency and specificity. In real-time reactions overall amplification efficiency can be followed by use of SYBR® Green to determine the $C_T$ value of the reaction. Optimal annealing conditions must be determined for each concentration of primer pairs that are to be assayed using a sequence-specific probe, see below.

Next, amplification is carried out in the presence of the specific probe under optimal conditions for several concentrations of the Limiting Primer in the range expected for the probe that will be used. When the probe is a molecular beacon, the preferred Limiting Primer concentration is found in the range of 10 nM to 100 nM. The preferred Limiting Primer concentration corresponds to the lowest Limiting Primer concentration that yields a mean $C_T$ value similar to those from samples with higher concentrations of that primer. Concentration below the preferred concentrations show increases of more than about 1 cycle as the concentration is decreased, which indicates that, under this circumstance, Limiting Primer depletion occurs too far in advance of reaching the detection threshold. In addition, samples with the preferred Limiting Primer concentrations will show linear rate of signal increase for several cycles after reaching threshold without plateauing, usually even 30 cycles after initial detection.

Protocol for Optimizing the Annealing Temperature for LATE-PCR

Once a suitable Limiting/Excess Primer pair has been chosen for use at a fixed ratio and absolute concentration, the $T_{m[0]}$ of each primer will have been, or can be, calculated using the Nearest Neighbor formula as described above. This done, it is important to empirically establish the Optimal Annealing Temperature at which to use these primers. The Optimal Annealing Temperature is the highest temperature at which the exponential phase of the reaction proceeds with maximal efficiency and maximal specificity at specific reagent concentrations and cycling times. By "maximum efficiency" we mean the condition that generates the lowest $C_T$ value during the exponential phase of reaction, wherein the specific product accumulates at the highest rate. As the annealing temperature is adjusted further downward toward the Optimal Annealing Temperature, the efficiency of the exponential phase of the LATE-PCR tends to increase. As the annealing temperature is adjusted downward below the Optimal Annealing Temperature, reactions tend to amplify non-specific amplicons. If, as is sometimes the case, the pair of primers being used does not hybridize non-specifically to alternate sequences within the target sample, decreasing the annealing temperature below the Optimal Annealing Temperature does not increase the efficiency of the reaction significantly and does not substantially decrease reaction specificity. Thus, the term Optimal Annealing Temperature as used in this application has a specific empirically-defined value, even for amplifications where lowering the annealing temperature below that temperature is not detrimental.

Protocol for Product Detection in Conventional Real-Time PCR

In the case of conventional real-time PCR the double-stranded product is detected by inclusion of a fluorescent dye or some type of a labeled probe, typically a fluorescent probe. Detection of double strands using a fluorescent dye may be done during the step of primer extension. The hybridization probes typically bind to one or both strands of the amplicon as the reaction is being cooled between the steps of strand melting and primer annealing. In practice this means that the melting temperature of the probe is higher than the melting temperature of the primer which hybridizes to the same strand as the probe (Mackay, I. M. (2002) "Survey and Summary: Real-time PCR in Virology", Nucleic Acids Res. 30(6):1292-1305). As the reaction is warmed again the probe is designed to disengage from the target strand while the primer extends along the target strand. Hybridization and extension of the other primer on the complementary strand also takes place during these steps. Probes that generate the detected signal through hybridization are detected during the annealing step. Probes that generate the detected signal through being hydrolyzed are detected following their degradation during the subsequent extension step. In either case, the amount of hybridized probe is limited by reannealing of the strands of the amplicon as their concentration increases. This means that only a fraction of the total number of target sequences present at the end of a conventional real-time reaction are actually detected.

In addition, under conventional real-time reaction conditions the hybridization probe must either fall off the target sequence prior to the extension step or be hydrolyzed during the extension step. If the hybridization probe fails to melt off its template strand quickly as the temperature is raised from primer annealing to primer extension in a symmetric PCR reaction, we have found that the probe may interfere with primer extension and reduce the amplification efficiency of the reaction.

Protocol for Product Detection in Real-Time LATE-PCR

Real-time LATE-PCR assays, like real-time symmetric PCR assays, include one or more labeled probes or fluorescent dyes for detection of the double-stranded and/or single stranded products. Again as in the case of symmetric PCR, detection of double-stranded product synthesized during the exponential phase of LATE-PCR can be carried out during either the primer-annealing or the primer-extension step, most preferably during the primer-extension step. The double-stranded product generated during the exponential phase of the LATE-PCR can be detected using a dye that binds double-stranded DNA, such as SYBR® Green. However, double-stranded DNA cannot be detected during a low-temperature detection step by use of a hybridization probe, such as a single-stranded probe or a molecular beacon, because the vast majority of the two amplicon strands are re-annealed to each other at the low temperature.

In one embodiment of the invention, detection of the accumulating single-stranded molecules can be carried out during the annealing step, i.e. prior to the extension step. It is preferred that the probe be a Low-$T_m$ Probe with a $T_{m[0]}^P$ at least 5° C., preferably at least 10° C. below $T_{m[0]}^L$. (Dual-labeled linear probes for the 5' nuclease assay (for example TaqMan® probes) are never Low-$T_m$ Probes, because they must remain bound to the template strand until they are degraded during primer extension.) Under these conditions Low-$T_m$ Probes detect the accumulating single-strands plus a fraction of the target strands that would otherwise reanneal to their complementary strands if the probe were not present. The exact magnitude of the fraction depends on the $T_{m[0]}^P$ as well as the reaction conditions and tends to vary slightly among replicate reactions, thereby introducing a variable in these measurements. In order to minimize this error it is preferred, for detection during the annealing step, to use a Super-Low-$T_m$ probe and to reduce the temperature of the annealing step below the mean annealing temperature for primer hybridization during the exponential phase of the reaction, with the proviso that this change in the thermal profile should not lead to mis-priming. Our preferred method to avoid mis-priming under these circumstances is to only lower the annealing temperature at, or preferably a few cycles before, the cycle at which the Limiting Primer becomes depleted and the reaction switches to synthesis of the Excess-Primer-Strand only.

In a more preferred embodiment of the invention, a detection step is introduced into the thermal profile of the reaction between primer extension of one thermal cycle and strand-melting of the next thermal cycle. In this case, the detection step is introduced for the purpose of detecting accumulating single-strand molecules after the extension step is finished, using hybridization probes that are complementary to sequences within the strand formed by extension of the Excess Primer. Detection can be carried out at any temperature at which the probe hybridizes to its target, in most cases below the extension temperature, and preferably at or below the annealing temperature, in combination with a Low-$T_m$ Probe. In the most preferred embodiment of the invention the added detection is carried out at a low temperature, preferably 5° C. below and most preferably 10° C. below, the mean temperature of the annealing step of the exponential phase of the reaction and utilizes a Super-Low-$T_m$ probe. Detection of the single-stranded product is most accurate when detection is carried out after the extension step of one cycle and the melting step of the next cycle, as compared to detection during the annealing step.

Introduction of a separate detection step into LATE-PCR, preferably a low-temperature detection step, has several advantages over the conventional strategy of probe detection prior to/or during the extension step. It makes it possible to separate primer annealing and extension from probe hybridization and detection. This, in turn, makes it possible to use elevated annealing temperatures and/or extremely short annealing times (such as "touch-down" annealing), designed to increase the stringency of the reaction and decrease the chances of amplifying an incorrect amplicon. It also makes it possible to routinely utilize non-hydrolysable Low-$T_m$ and/or Super-Low-$T_m$ probes instead of conventional hybridization probes. Also introduction of a low-temperature detection step also makes it possible to monitor the presence of the extension product of the Limiting Primer (the Limiting-Primer Strand) that remains constant during the linear phase of LATE-PCR, while simultaneously measuring the accumulation of the Excess-Primer-Strand that increases linearly during the linear phase of LATE-PCR. This can be done by use of a labeled Limiting Primer that is incorporated into the Limiting-Primer-Strand, and also using a Low-$T_m$ Probe or a Super-Low-$T_m$ Probe that gives off its own distinct signal to measure the accumulating Excess Primer-Strands. In addition, because the temperature of the reaction is immediately increased to the melting temperature when the detection step is used, there is a decreased opportunity for a mis-match primer to extend. In contrast, when a conventional probe is used, a mis-matched primer has an excellent chance of extending, because the conventional detection step during primer annealing is followed by the conventional extension step.

Advantages of Low-$T_m$ Probes and Super-Low-$T_m$ Probes

Low-$T_m$ and Super-Low-$T_m$ probes have the following advantages as compared to conventional hybridization probes: a) these probes increase signal strength because, when used at high concentrations, they bind to all accumulated single-strands; b) these probes are more allele specific than conventional probes; and c) these probes have a better signal-to-noise ratio than conventional probes, because they are detected at lower temperatures at which non-specific fluorescence background is typically lower.

Protocol for Designing and Characterizing Low-$T_m$ Probes

Low-$T_m$ probes and Super-Low-$T_m$ probes compatible with LATE-PCR include, but are not limited to, one or more probes of the following types: 1) single-stranded linear probes labeled as is known in the art, including FRET probes; 2) double-stranded probes, as is known in the art; 3) stem-loop single-stranded probes, including molecular beacons, labeled as is known in the art. These general classes include probes containing unconventional nucleotides such as PNA or 2-O-methyl modifications, probes with attached moieties that affect hybrid stability such as Minor-Grove-Binding probes (e.g., Eclipse™ probes), and probes that are physically attached to primers (e.g., Scorpion probes). Low-$T_m$ probes and Super-Low-$T_m$ probes are constructed based on the following logical steps:

1) The experimenter chooses which type of probe is to be used;
2) The experimenter decides on the probe's target sequence, approximate length, and chemical composition. The experimenter designs the probe using an appropriate software package, while applying certain well known general principles of nucleic acid biochemistry. Many software packages for this purpose are known in the art, but are not available for types of probes comprised of non-conventional subunits. The software package may offer an approximate estimate of $T_{m[0]}^P$ of the probe. The following general principles are useful for designing these probes: a) under constant experimental conditions shorter probe/target hybrids tend to have lower $T_m$ values than longer probes; b) under constant experimental conditions probes/target hybrids with fewer hydrogen bonds tend to have lower $T_m$ values than probes with more hydrogen bonds; c) under constant experimental conditions probe/target hybrids that are mismatched tend to have lower $T_m$ values than probe/target hybrids that are perfectly matched.
3) The experimenter empirically establishes the approximate $T_{m[0]}^P$ of one or more possible probes using a melting temperature assay. Many types of melting temperature assays for probe/target hybrids are well known in the art. One version of a melting temperature assay is outlined here. An experimental mixture of the probe and its target is prepared under conditions that simulate the composition of the LATE-PCR reaction mixture. Tests are prepared at probe:target ratios of 1:1 and one or more probe concentrations within the sensitivity range of the instrument that will employed for the melting temperature assay. These mixtures are then subjected to a melt temperature assay. In the case of fluorescently labeled probes the melting temperature assay is carried out in a fluorimeter having thermal regulation. The melting temperature of each probe-target pair is the temperature at which 50% of the probe molecules are hybridized to the target molecules. The experimentally determined melting temperature is the $T_{m[0]}^P$ of that probe under those conditions. However, as will be understood by those skill in the art, this empirically determined value is different from the actual melting point of probe-target hybrids in an actual LATE-PCR. This is because the concentration of the target added to melting point assay is equal to the concentration of the probe, whereas in a LATE-PCR the probe is in excess of the concentration of the target, which begins the reaction at zero and almost never reaches the probe concentration over the course of the reaction.
4) In the case of Low-$T_m$ Probes, the empirically established $T_{m[0]}^P$ melting temperature should be at least 5° C. below, most preferably at least 10° C. below, $T_{m[0]}^L$ of the Limiting Primer. In the case of Super-Low-$T_m$ Probes, the empirically established $T_{m[0]}^P$ should be below, preferably at least 5° C. below, more preferably at least 10° C. below, the mean annealing temperature used for the primer pair during the exponential phase of the reaction.
5) The low-temperature detection step, when used, does not need to be included in every thermal cycle of LATE-PCR. In fact, under certain circumstances it is desirable to use a Low-$T_m$ probe or Super-Low-$T_m$ probe without including the detection step until the end of the reaction. For instance, it may be desirable to keep the stringency of the single-strand amplification phase very high for many cycles to prevent Product Evolution (discussed below) or mis-priming. Under these circumstances dropping the temperature below that required for stringency, during any step in the thermal cycle, could encourage the Product Evolution of single strands, or could lead to generation of non-specific products. However, once the desired number of single-stranded product molecules has accumulated in LATE-PCR, introduction of a low temperature detection step can be used to measure the amount of the accumulated single strands. If SYBR® Green is also present in the reaction, or a second probe to the opposite strand is also present in the reaction, a measure of the number of double stranded molecules can also be obtained. The resulting data, together with knowledge of the thermal cycle at which the LATE-PCR switched from exponential amplification to linear amplification, can be used to estimate the efficiency of single-strand synthesis in the reaction.

Figure 8:
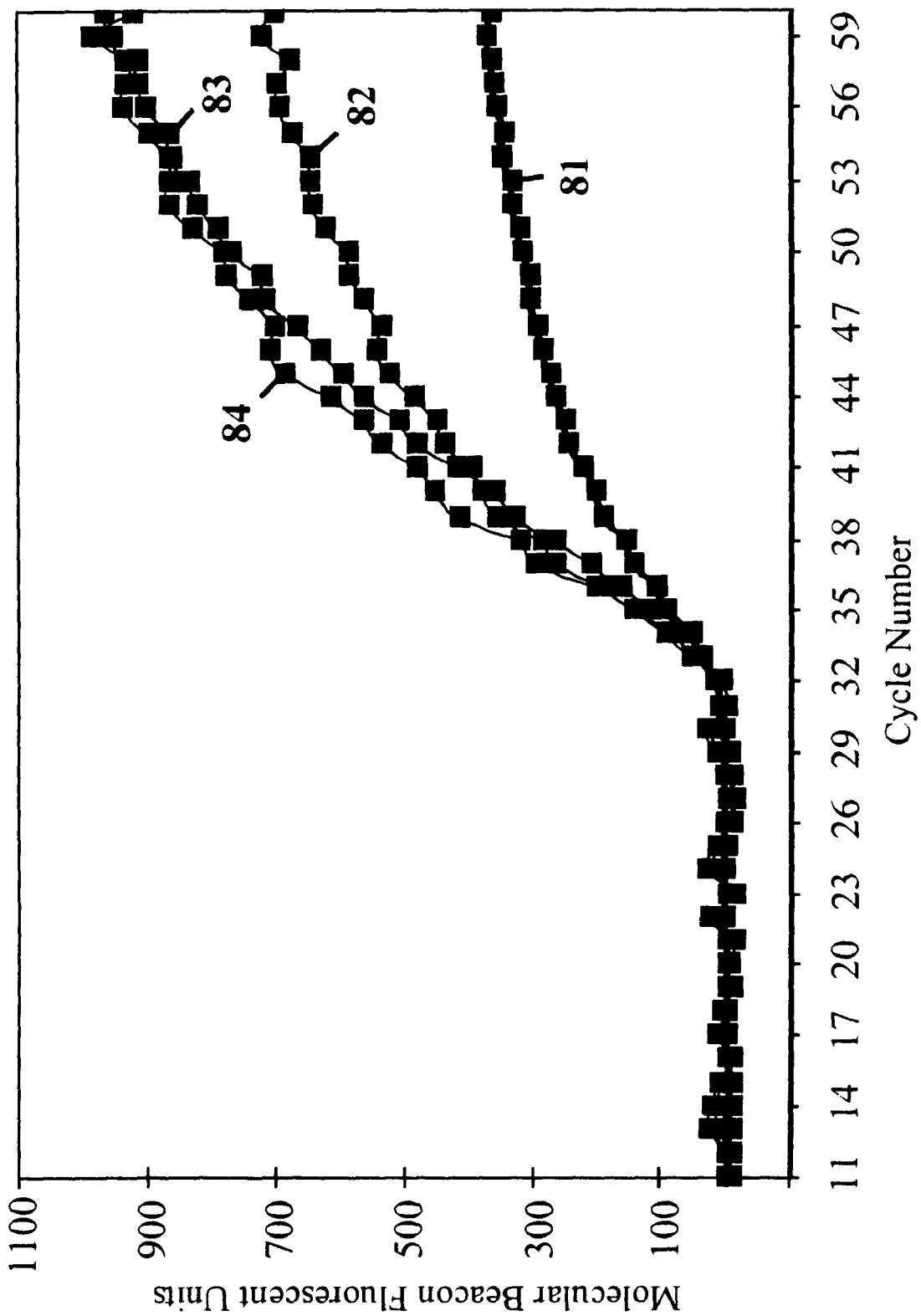
FIG. 8 presents real-time fluorescence curves from PCR amplifications having different concentrations of Low-$T_m$ Probe.

Protocol for Optimizing Low-$T_m$ Probe and Super-Low-$T_m$ Probe Concentrations for LATE-PCR Replicate LATE-PCR assays are performed each with an initial probe concentration ranging above or below that used to establish the empirical $T_{m[0]}^P$ for that probe (see above). The intensities of the signals generated in reactions are compared and the optimal probe concentration is chosen as the lowest concentration that gives the maximum signal. For instance, FIG. 8 shows four parallel LATE-PCR assays each containing a different concentration of a Low-$T_m$ molecular beacon (0.6 μM, curve 81; 1.2 μM, curve 82; 2.4 μM, curve 83; 4.0 μM, curve 84). The results show that 2.4 μM (curve 83) is the optimal concentration for this Low-$T_m$ Probe under the conditions of this LATE-PCR.

Protocol for Optimizing the Absolute Concentration of the Magnesium in a LATE-PCR Alterations in $Mg^{++}$ concentration affect many other aspects of the LATE-PCR, as is the case in conventional PCR. The factors affected include the $T_m^A$, $T_{m[0]}^L$, $T_{m[0]}^X$, the optimal annealing temperature, $T_{m[0]}^P$, closing of the stem of a molecular beacon, and the activity of Taq DNA polymerase. Generally, the $T_m$ of each component in the reaction increases as the $Mg^{++}$ concentration increases, but the specificity of interactions between each oligonucleotide and its target sequence decreases. These effects of $Mg^{++}$ are well known to persons skilled in the art of PCR. It is therefore necessary to empirically define the optimal Mg$^{++}$ through a series of parallel reactions. We prefer optimal Mg concentrations in the range of 1-6 mM, most preferably in the range of 24 mM.

LATE-PCR Assay Kits

A LATE-PCR reagent kit has been designed for use in the detection of the normal and ΔF508 Alleles of the human cystic fibrosis gene during preimplantation genetic diagnosis (PGD). The kit described here is modular; that is, it contains DNA polymerase in one package and all other reagents and materials in another package. It will be appreciated that the primers and probes together comprise an oligonucleotide set, which can be marketed as a separate product. The kit, its use, and the assay performed with the kit, which we call the "CFΔ508 Kit," are described in Example 6 in a format that might appear on a product insert accompanying the kit.

Similar kits can be designed for use with other targets generally, including but not limited to single cells from sources other than human embryos, or pluralities of cells, or DNA or RNA recovered from plant or animal cells or other sources cells. In the case of samples comprised of RNA the LATE-PCR kit can be used in conjunction with a variety of procedures known in the art for isolation or purification of RNA and conversion of said RNA into cDNA.

LATE-PCR Assays Based on the Use of Three Primers

Certain embodiments of LATE-PCR assays use an additional Limiting Primer to generate a relatively long double-stranded amplicon from two Limiting Primers during the initial, exponential phase of the reaction, followed by generation of a shorter single-stranded amplicon utilizing one strand of the long amplicon as template and the Excess Primer as the primer. While this can be accomplished by opening the reaction vessel to add the Excess Primer after multiple cycles of exponential amplification, preferred LATE-PCR 3-primer assays utilize initial reaction mixtures that contain all three primers together with an amplification protocol that preferentially utilizes the Excess Primer only in later cycles. The Limiting Primers are a pair of matched PCR primers, designated L1 and L2, for generating the large amplicon. The primers are "matched"; that is their $T_m$'s are "balanced". The concentration of L2 is roughly equal to the concentration of L1, that is, from 0.2-5 times the concentration of L1, preferably equimolar. The initial concentration-dependent melting temperatures, $T_{m[0]}^{L1}$, and $T_{m[0]}^{L2}$, of L1 and L2 are as close as possible to one another, while $T_{m[0]}^{X}$, of the Excess Primer is at least 5° C., preferably at least 10° C., below the $T_{m[0]}$ of both Limiting Primers. Initial cycles of PCR amplification, either 3-step PCR or 2-step PCR, utilize an annealing temperature higher than the $T_{m[0]}^{X}$ of the Excess Primer, such that the Excess Primer does not participate materially in the generation of amplicons. After a selected number of these high-temperature cycles, preferably near the point exponential amplification ceases due to depletion of L1 and L2, the annealing temperature is lowered such that during subsequent cycles the Excess Primer participates in amplification (exponential amplification, if its pairing Limiting Primer has not been completely exhausted, followed by linear amplification of single-stranded LATE-PCR product). Thus, the relationship between the melting temperature of the shorter amplicon formed by extension of the Excess Primer, that is $T_m^A$ of the amplicon is not more than 25° C. above $T_{m[0]}^{X}$ of the Excess Primer, preferably not more than 20° C. above and more preferably not more than 18° C. above.

The present invention is an improvement in the digital PCR method (Vogelstein, B., & Kinzler, K. W. (1999) "Digital PCR" Proc. Natl. Acad. Sci. USA 96:9236-9241). According to this method single DNA molecules are amplified by symmetric PCR. Once the symmetric reaction is completed a single additional primer is added to the reaction to amplify just one strand of the accumulated double-stranded molecules. The resulting single strands are then detected by addition of an appropriate fluorescent probe, or by electrophoresis. LATE-PCR can be used to carry amplification of both the double-stranded product and the single stranded product in one reaction. In some applications, such as the detection of cancer DNA molecules present in feces (Shih, I., et al. (2001) "Evidence That Genetic Instability Occurs at an Early Stage of Colorectal Tumorigenesis" Cancer Res. 61:818-822), LATE-PCR amplifications can be carried out in situ, such as in agarose or polyacrylamide gel.

Quantitative LATE-PCR Assays

Assays based on LATE-PCR allow quantitative measurement to be obtained in three ways. First, real-time LATE-PCR can be used to measure the $C_T$ value of a signal. As in the case of real-time symmetric PCR, the $C_T$ value can be used to deduce the number of target molecules present in the initial sample. This is accomplished by comparing the $C_T$ value of the sample with a standard curve generated by analyzing known amounts of the same target sequence under conditions that simulate those of the unknown sample. Second, the slopes of the signal during the linear amplification phase of the real-time LATE-PCR can be measured. As illustrated below for a single copy sequence, the linear slopes of homozygous diploid cells are approximately twice those for the same sequence in heterozygous diploid cells. Third, LATE-PCR under optimized conditions can be used to determine the relative number of different allelic copies present by means of end-point assays.

End-point LATE-PCR assays can also be used to provide an estimation of the number of targets in the original sample, if the relative number of alleles is known and the slope of the line is similar among replicate samples. This is possible because LATE-PCR reactions do not plateau but continue to increase linearly for many cycles. Thus, once the expected $C_T$ values of such reactions have been established, single data points can be used to extrapolate the slopes of the lines and hence the number of target molecules present at the start of the reaction. Similarly, if the number of target molecules and expected $C_T$ values are first established, end-point assays can be used to quantify the frequencies of different allelic sequences among them.

In the case of both real-time and end-point assays, it will be appreciated that both the double-stranded products and the single-stranded products of a LATE-PCR amplification can be monitored simultaneously by use of a combination of dyes and hybridization probes, or a combination of hybridization probes and primer probes. Listed below are some possible strategies that can be used but, as will be appreciated by those skilled in the art, additional strategies are possible:

In the case of single amplicons two hybridization probes can be used to simultaneously measure the synthesis and accumulation of the extension product of the Limiting Primer that stops being synthesized at the end of the exponential phase, as well as the extension product of the Excess Primer that continues to accumulate linearly.

Alternatively, accumulation of the extension product of the Limiting Primer can be monitored using a labeled double-stranded primer and its quenched complementary strand (as described by Li et al., while the extension product of the Excess Primer can be monitored by use of an appropriate hybridization probe, such as a molecular beacon or a double-stranded probe.

Alternatively, accumulating double-stranded amplicons can be monitored by binding an intercalating dye, such as SYBR Green®, while the single-stranded extension product of the Excess Primer can be monitored by use of an appropriate hybridization probe, such as a molecular beacon.

In the case of multiplex reactions several probes can be used to simultaneously monitor several strands that continue to accumulate during the single-strand phase of the reaction.

LATE-PCR Assays Used to Establish Genomic Zygosity

Assays of this invention permit the discrimination between genomes that are homozygous for a particular allele versus those that are heterozygous for that allele. Assays that can distinguish between homozygous cells and heterozygous cells can be performed starting with single cells or single genomes, but other samples may also be used, provided that the two samples being compared have approximately the same amounts of DNA at the start of the reaction. Assays that can distinguish between homozygous and heterozygous cells are clinically or commercially important, because they can distinguish between organisms that do or do not carry one or two copies of a particular allele or a variant of that allele.

Figure 9:
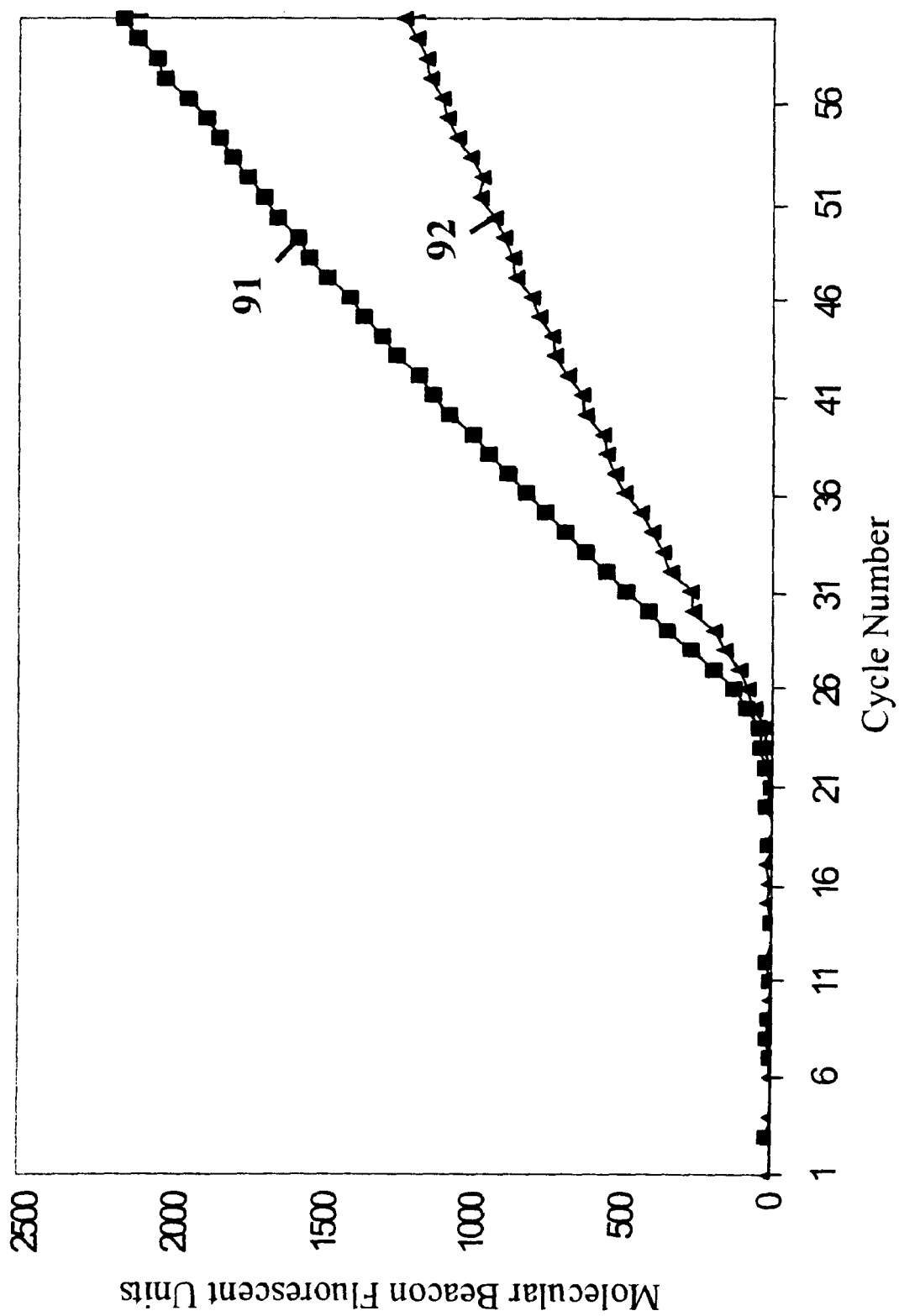
FIG. 9 presents real-time fluorescence curves from PCR amplifications of homozygous cells compared to heterozygous cells.

As shown in FIG. 9, the presence of one copy of a selected nucleic acid sequence present in a heterozygous diploid cell can be distinguished from the presence of two copies of the same nucleic acid sequence in a homozygous diploid cell by means of real-time LATE-PCR assay in which one molecular beacon is used to detect one of the alleles in the heterozygous cell, or two differently-colored molecular beacons are used, one for one allele and the other for the other allele in the heterozygous cell. The resulting fluorescent signals generated from such samples demonstrate that, for each allele, the linear slope of the signal arising from homozygous cells containing two copies of that particular allele (curve 91) increases at a rate that is approximately twice the rate of the signal for the same allele generated by the equivalent number of heterozygous cells that contains one copy each of two different alleles (curve 92)

It will be appreciated that for this use of the invention it is particularly important that the slopes of the lines generated during the single-strand phase of the reaction be optimized for reproducibility, that is, show the least possible scatter among replicates. In this regard it is most preferred that $(T_{m[0]}^L - T_{m[0]}^X) \geq +3$. FIG. 9 illustrates such an optimized case for genomes that are homozygous vs. heterozygous for the 1421 allele of the HEX-A gene, one of the common alleles responsible for Tay-Sachs Disease. Each of curves 91, 92 in FIG. 9 is the average of 15 replicate tests. It is apparent in this example that the homozygous normal DNA (assayed for the wildtype allele) has an average slope approximately twice as steep as the average slope for the wildtype allele present in cells heterozygous for the 1421 allele. Either the slopes of the curves generated by LATE-PCR assays, or end-point values generated by LATE-PCR assays can each be used to distinguish between homozygous and heterozygous cells.

LATE-PCR also can be used to distinguish between genomes that are heterozygous for a particular allele and genomes that are hemizygous for the same allele. Assays that can distinguish between hemizygous cells and heterozygous cells can be performed starting with single cells or single genomes, but other samples may also be used, provided that the two samples being compared have approximately the same amounts of DNA at the start of the reaction. Assays that can distinguish between hemizygous and heterozygous cells are clinically or commercially important because, among other phenomenon, they can be used to detect "loss of heterozygosity" a well known event that takes place in certain cancers and in normal cells of the immune system undergoing recombination and loss of a portion of the immunoglobin genes during the course of cellular differentiation. In such cases a small piece or large piece of one chromosome is lost, thereby rendering a portion of the genome hemizygous. Heterozygous cells generate signals in a LATE-PCR assay, monitored with an appropriate probe, that have slopes and/or endpoints that are approximately one-half those generated by the same probe monitoring amplification of the DNA from a hemizygous cell.

Multiplex LATE-PCR Assays

Figure 10:
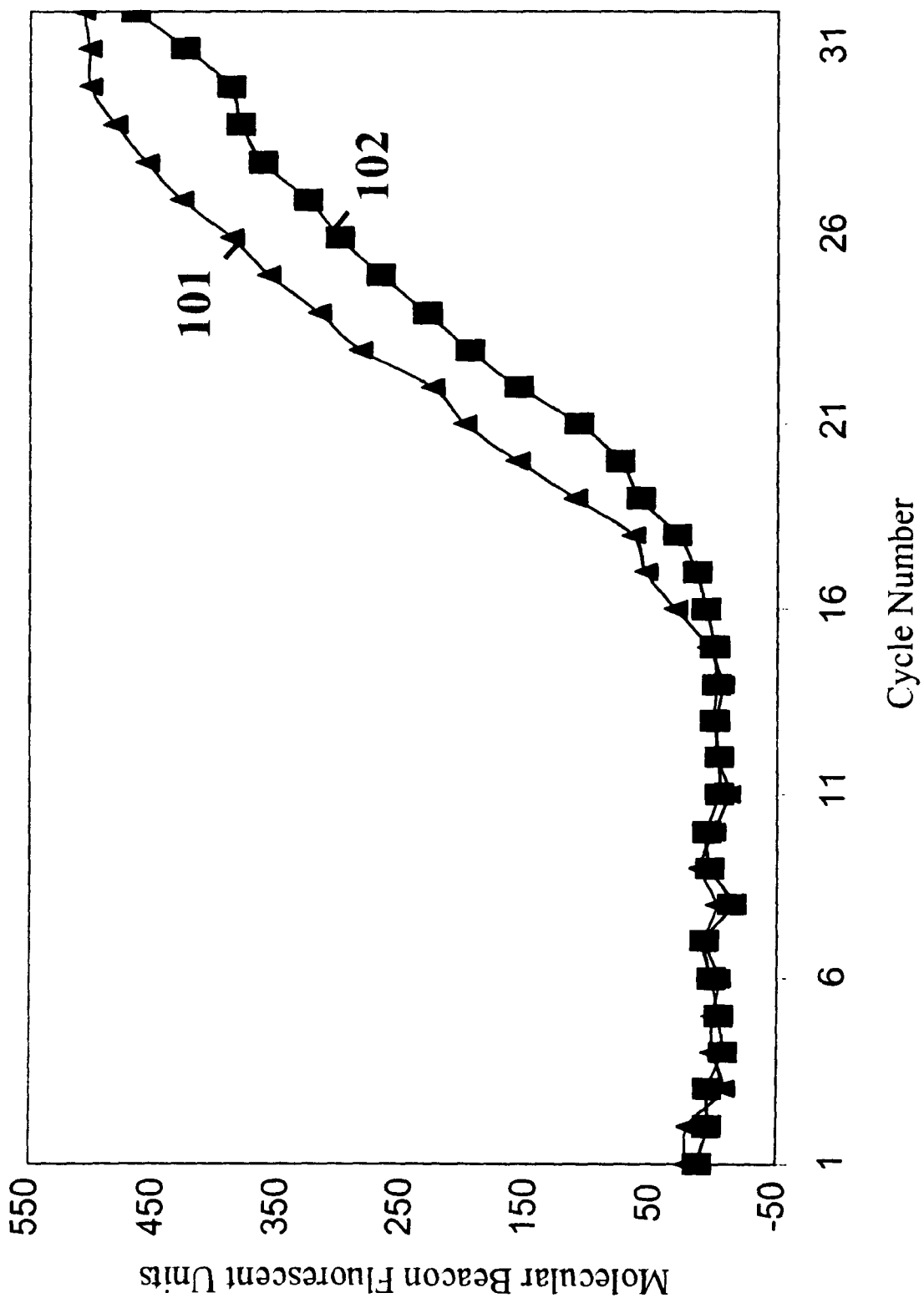
FIG. 10 presents real-time fluorescence curves from a multiplex PCR amplification of two target sequences.

Assays according to this invention include multiplex assays for simultaneous amplification of two or more target sequences with different primer pairs in the same reaction mixture. For multiplex assays, it is recommended that the various primers be analyzed to screen out obvious cases of undesirable cross-hybridization between two amplicons and between one primer pair and amplicons from other primer pairs. For multiplex assays, the concentration-adjusted melting temperatures, $T_{m[0]}^L$, of all Limiting Primers should be equal to or higher than the concentration-adjusted melting temperatures, $T_{m[0]}^X$, of all Excess Primers. Preferably, the linear phase of multiplex amplifications is carried out under stringent conditions to minimize false priming. FIG. 10 shows the results of a multiplex assay according to this invention. Two separate amplicons were synthesized from the HEX-A gene. One target sequence included the site for the 1278 mutation. The other target sequence included the site for the 1421 mutation. Differently labeled (TET in one case, FAM in the other) molecular beacon probes were used to monitor the two amplicons in real time. The two plots of fluorescence in FIG. 10 (curves 101 and curve 102) show that both targets were amplified successfully.

Assays according to this invention, particularly multiplex assays, may include the use of universal priming sequences. We have designed a multiplex assay that uses a primer pair for each amplicon in which each Limiting Primer has a universal 5' sequence and that also uses an extra primer, a universal primer, that includes only the universal sequence. The universal primer has a concentration-adjusted melting temperature, $T_{m[0]}^U$, that is lower than $T_{m[0]}^X$ of the Excess Primers. Limiting Primers and Excess Primers have concentration-adjusted melting points as described above. They are added at the described ratio, for example, 1:20 or greater, but at very low concentration, for example 1 nM for the Limiting Primers. An example of preferred concentrations is 1 nM for the Limiting Primers and 50 nM for the Excess Primer. Initial cycles of amplification are at conditions appropriate for the primer pairs, and the Limiting Primers are exhausted after a relatively few cycles. The universal primer does not participate in these initial cycles. From about that point onward the Excess Primers function as "Limiting Primers" relative to the universal primer, which has a concentration-adjusted melting temperature, $T_{m[0]}^U$, lower than those of the Excess Primers present in the reaction, but is present at a concentration at least 5 times, preferably at least 10 times, greater than the concentration used for the Excess Primers. Further temperature cycles during this second phase of the amplification utilize a lowered annealing temperature appropriate for the universal primer. After exhaustion of the Excess Primers, continued cycling leads to synthesis of single-stranded products via extension of the universal primer. In essence, this method couples a first LATE-PCR amplification to a second LATE-PCR reaction, wherein the Excess Primer(s) in the first amplification are the Limiting Primer(s) in the second.

The efficiency of the multiplex assay described above may be limited during the initial cycles of the reaction because the concentrations of the Limiting Primers and the Excess Primers are low. If necessary, the initial efficiencies of amplicon production can be increased by raising the concentrations of these primer pairs. Raising the concentration of these primer pairs can be accomplished by a volume change, that is, by carrying out the first phase of the amplification utilizing a much smaller reaction mixture volume than the reaction mixture volume of the second phase. Under these conditions the volume of the reaction can be increased at or near the thermal cycle at which the temperature of the annealing phase is lowered to allow the universal primer to begin functioning. An alternate version of the multiplex assays described above is to add the universal primer to the assay at the time it is first needed.

Additional LATE-PCR Amplifications and Assays.

It may be desirable to convert one or more of the single-strand products in a LATE-PCR amplification back into double-stranded products. This can be accomplished by including a "Low-$T_m$ Primer" in a reaction. A "Low-$T_m$ Primer" only hybridizes to its complementary sequence when the temperature is dropped below the $T_{m[0]}$ value of said primer during an additional step included in thermal cycles late in the reaction and then is slowly raised to allow for extension of said primer and, hence, allowing the accumulated single-stranded molecules to be converted back into double-stranded DNA. If initial attempts at conversion prove inefficient, the time spent at the low temperature step can be lowered and/or the rate of temperature increase from the low temperature can be slowed. Alternatively several down-and-up temperature oscillations, for instance between 45° C.-72° C.-45° C.-72° C.-... can be carried out prior to either ending the reaction or continuing on to the melting step of the next thermal cycle. A version of this embodiment of the invention is to design a "Low-$T_m$ Primer" that can hybrid to a sequence within the accumulating single-stranded product, rather than at or near its 5' end. In this case, only the portion of the single-strand that is 3' of the "Low-$T_m$ Primer" is converted to a double-strand. The product strands of this reaction can become substrates for synthesis of additional truncated single-strands using the original Excess Primer.

The process described in the preceding paragraph has several potential novel uses: 1) it can be useful for "covering up" a sequence within the single stranded molecule that might otherwise "interfere" with a subsequent step, for instance capturing of the molecule single-stranded molecule on a solid matrix; 2) it can be used to measure or unfold regions within a single-stranded molecule that exhibit secondary structures such as hairpins; 3) it can be used to block Product Evolution (the phenomenon of Product Evolution is described below); 4) it can be used to enable detection of the single stranded molecule by staining with at dye, such as SYBR® Green, which can bind to the double-stranded portion of the single-stranded molecule; 5) it can be used to increase the rate of single-strand synthesis by extension of the Excess Primer; 6) by using a labeled Low-$T_m$ primer, this method can be used to label the strand complementary to the single-stranded product.

Single-strand to double-strand conversion can be combined with end-point analysis to achieve another form of LATE-PCR end-point assay. In this case the reaction is carried out in the presence of an Excess Primer that is fluorescently tagged at its 5'end and an additional oligonucleotide that is complementary to this primer and blocked with a quenching moiety, such as Dabcyl, at its 3'end. The complementary oligonucleotide (CO) is designed to have a $T_{m[0]}^{CO}$ at least 5° C. below the $T_{m[0]}^{X}$ of the Excess Primer to its target sequence in the amplicon (see Li et al. 2002) One additional short oligonucleotide, the Low-$T_m$ Primer, is also added to the reaction. The Low-$T_m$ primer is designed to hybridize to a sequence within the single-stranded product of the reaction, when the temperature of the reaction is dropped in the low-temperature step. When the temperature is then slowly increased, the DNA polymerase extends the Low-$T_m$ Primer, converting the 5'end of the single-strand into a double-strand.

Under these circumstances the fluorescently-tagged Excess Primer is incorporated into every copy of the amplicon strand that it primes, during both the exponential and the linear phase of LATE-PCR. At the end-point of the reaction, when the temperature of the reaction is dropped-and-then-raised, the Low-$T_m$ primer is extended and the complementary oligonucleotide hybridized to the 5'end of the single-strand is displaced. When the reaction temperature is dropped for a final time, the incorporated copies of the Excess Primer fluoresce, while the unincorporated copies of the Excess Primer hybridize to their complementary strands that quench their fluorescence, in accord with the findings of Li et al. (2002). The resulting fluorescence of the incorporated primers can be used as a measure of the number of single-stranded molecules that have been synthesized in the reaction.

LATE-PCR can also be used to generate single-stranded molecules in situ, which are then subsequently detected by use of a secondary method of amplification, such as rolling circle amplification combined with various means of detection the resulting single strands. This application of LATE-PCR takes advantage of the high level of primer-target specificity afforded by PCR, but does not require that the number of single-stranded molecules so generated be directly detectable. The secondary method of amplification, which might otherwise generate an unacceptably high rate of false positives, then is used to detect the presence of the pool of specific single-stranded molecules generated by the LATE-PCR reaction. As will be recognized by persons skilled in the art, LATE-PCR with secondary amplification is also useful for multiplexing, because it avoids the generation of high concentrations of LATE-PCR products that might tend to interact.

When LATE-PCR is combined with a secondary method of amplification to further amplify, the relationship between amplicon $T_m^A$ and Excess Primer, $T_{m[0]}^X$ becomes less constraining and may exceed 25° C.

Use of LATE-PCR for Production of Single-Stranded Molecules:

In addition to assays, LATE-PCR can be used to synthesize single-stranded products for any purpose. One such purpose is the generation of starting material for subsequent methods of sequencing. Another is production of single-stranded oligonucleotides for use as hybridization probes, for example, in situ hybridization probes.

Product Evolution During LATE-PCR Amplification:

Whereas symmetric PCR amplifications tend to plateau and stop after about 50 cycles, amplifications according to this invention continue to generate single-stranded amplicons for 75 cycles or more. We have discovered, however, that in some instances the single-stranded molecules that accumulate during amplification of some targets tend to interact and "evolve", if the thermal cycles are not maintained at a high level of stringency. The resulting "derivative molecules" are then amplified as double-stranded molecules. We call this "Product Evolution." Product Evolution is not consistently observed by use of a hybridization probe, such as molecular beacons, because these probes tend to hybridize both to the initial single-stranded product of the reaction and to the "derivative molecules" generated by Product Evolution. However, the process of Product Evolution can be detected and analyzed by use of SYBR® Green, which stains double-stranded molecules regardless of their sequence, and by melting point analysis of the resulting products. Product Evolution can be further analyzed by electrophoresis of the amplified products.

Figure 11A:
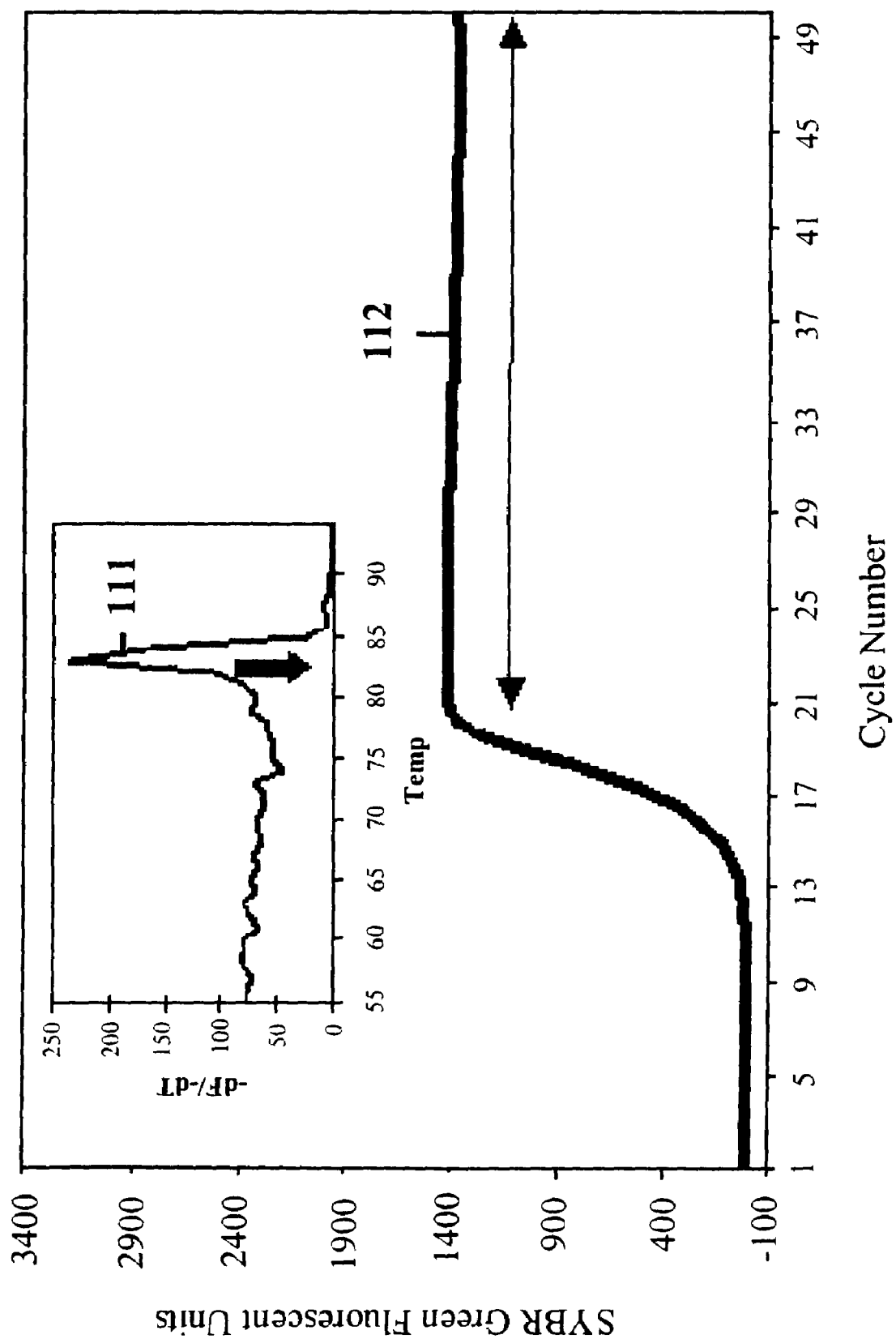
FIGS. 11A, 11B present melt analyses and fluorescence curves from LATE-PCR amplifications performed with a stringent annealing step and with a non-stringent annealing step.
Figure 11B:
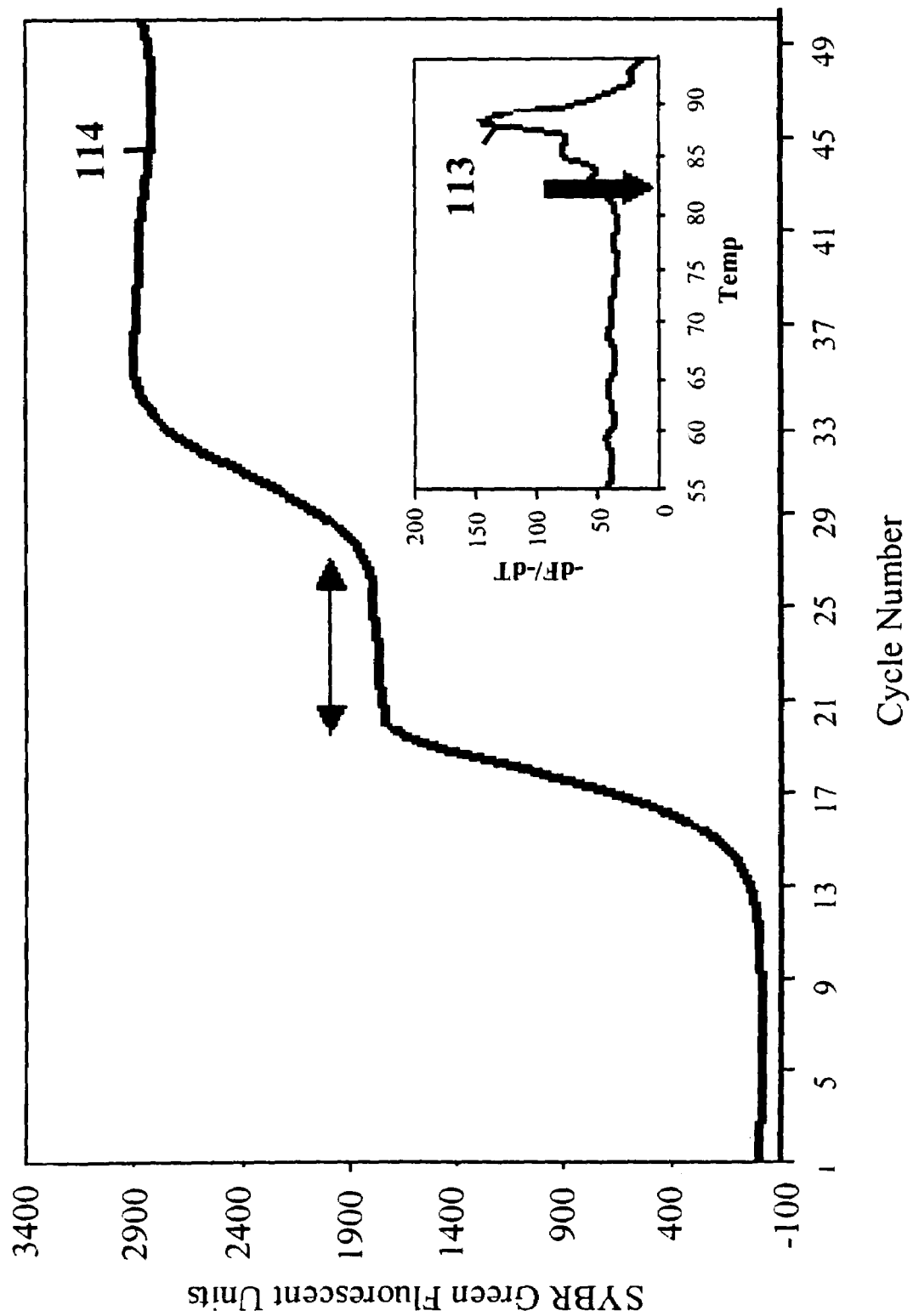

Product Evolution is stochastic and undesirable, insofar as it alters the sequence of the amplified product. This phenomenon has been reported for asymmetric PCR (Gyllensten and Erlich, (1988)), although the molecular mechanism is unknown at this time. Product Evolution may be initiated by inappropriate priming of derivative amplicons. FIG. 11 illustrates the phenomenon of Product Evolution and demonstrates that increasing the stringency of the annealing step in a LATE-PCR amplification or assay delays Product Evolution. Comparison of FIG. 11A and FIG. 11B shows how the phenomenon of Product Evolution is distinct from amplification of non-specific products. Comparisons of the insets show how the product can evolve to a higher melt peak under non-stringent conditions. Curve 111 is the melt analysis of a sample generated under stringent conditions and curve 112 shows the kinetics of amplification under stringent conditions. Curve 113 is the melt analysis of a sample generated under non-stringent conditions, and curve 114 shows the kinetic analysis of amplification under non-stringent conditions. Horizontal arrows in the graphs indicate the number of cycles of single stranded DNA accumulation in the absence of product Evolution; vertical arrows in the insets show the temperature melting peak for the correct product.

It will be recognized by individuals skilled in the art that there are a number of ways to increase the stringency of the reaction and thereby suppress inappropriate initiation. The possible ways of increasing stringency include:
  a) increasing the annealing temperature to limit the hybridization of the primers, particularly the Excess Primer,
  b) raising or lowering the extension temperature away from the optimum of the DNA polymerase,
  c) decreasing the concentration of the DNA polymerase,
  d) decreasing the concentration of the Excess Primer,
  e) in assays employing a low temperature detection step, limiting that step to minimal duration followed by rapid ramping to melting temperatures in order to minimize possible primer extension at mismatched sites.

An alternate explanation to account for Product Evolution is that it is caused by imperfect annealing of the Excess Primer to a site within either a) the initial genome, or b) the single-strands that accumulate during the linear phase of LATE-PCR. Imperfect annealing would not occur if amplification conditions remain stringent but would be favored each time the temperature is dropped during a low temperature detection step in an assay. An imperfectly hybridized primer, once bound, will be extended to the 5' end of a single-strand template. In case b), the resulting partial strand would then be amplified as a short double-stranded molecule in subsequent thermal cycles, because the same Excess Primer would prime replication in both directions.

Product Evolution and non-specific amplification can be suppressed by temporarily decreasing the effective concentration of the Excess Primer and hence, increasing specificity, each time an assay proceeds through the low temperature detection step. This goal can be achieved by inclusion of an oligonucleotide that is complementary to the Excess Primer, but only binds to the Excess Primer when the temperature of the reaction is reduced below the annealing temperature of the Excess Primer to its target sequence in the amplicon. The optimal base sequence of the complementary oligonucleotide depends on the sequence composition of the particular Excess Primer and is established experimentally. However, it can be anticipated that the complementary oligonucleotide will have the following characteristics:

The concentration-adjusted melting temperature of the complementary oligonucleotide, $T_{m[0]}^{CO}$, should be at least 3° C. below $T_{m[0]}^{X}$. This can either be achieved by decreasing the concentration of the complementary oligonucleotide relative to the Excess Primer, or by altering the length or the sequence of the complementary oligonucleotide relative to the Excess Primer. However, it is most desirable to keep the concentration of the complementary oligonucleotide in excess of the concentration of the Excess Primer, so that when the temperature of the reaction is dropped below $T_{m[0]}^{CO}$, the majority of Excess Primer molecules will be hybridized to complementary oligonucleotide molecules. It is therefore most desirable to either shorten the complementary oligonucleotide relative to the Excess Primer, or to deliberately mismatch the complementary oligonucleotide of the Excess Primer or both. Most preferably, the complementary oligonucleotide can be shortened at its 3' end. At least the three bases at the 5' end of the complementary oligonucleotide should be perfectly matched to the three bases at the 3' end of the Excess Primer to prevent the Excess Primer from initiating strand replication. Further, the 3' end of the complementary oligonucleotide should be blocked by a modification such as a phosphate group to ensure that the complementary oligonucleotide cannot act as a primer.

Assays that utilize amplification according to this invention include homogenous end-point assays and homogenous real-time assays. In homogenous assays, no separation of products is required. Generally tubes of the amplification reaction need not be opened, as detection means, for example fluorescent dyes or fluorescent probes, can be added prior to the start of amplification. Assays according to this invention may utilize either 2-step PCR or 3-step PCR. Certain preferred embodiments additionally include a low temperature detection step following primer extension. If a low temperature detection step is used, it need not be included in the early cycles of amplification and preferably is omitted until 5-10 cycles prior to the $C_T$ to promote specificity and suppress Product Evolution, discussed above, while still making it possible to establish background levels of fluorescence prior to $C_T$.

LATE-PCR Assays Combined with Harvesting of Single-Stranded Products

Whether LATE-PCR is carried out for the purpose of generating a single amplicon or many amplicons, it is desirable to minimize inappropriate interaction of single-stranded molecules in order to reduce the chance that Product Evolution will occur as the concentration of these molecules increases. Periodic capture and removal of single-stranded molecules from an ongoing reaction, during selected or all linear amplification cycles, provides a simple and versatile means of keeping the concentration of the products low. Capture and removal of single-stranded molecules can be accomplished in a variety of devices and formats. For example, a LATE-PCR amplification can be carried out in a "racetrack" like chamber around which the reactants repeatedly cycle. The speed at which the reactants rotate around the racetrack can be controlled, and adjacent sections of the racetrack can be differentially heated or cooled to achieve the required pattern of thermal cycling. One sector of the racetrack, or several adjacent sectors of the racetrack, can have surfaces that include covalently linked capture probes with one or more sequences complementary to one or more single-stranded products. As the reactants pass through these sectors the temperature of the reaction can be cooled, as in a low-temperature detection step. Under these conditions, each single-stranded molecule will hybridize to its particular capture probes, while double-stranded template molecules, as well as Taq DNA polymerase (and other proteins) and all of the small molecules of the reaction mixture move onward to the next chamber in the racetrack. Once the reactants have cleared the capture-probe sector of the racetrack, it can be isolated and its temperature raised to release and recover the single-stranded molecules for subsequent analysis or manipulation. Persons skilled in the art will appreciate that the above principles can be applied to additional systems and devices designed to harvest the single-stranded products of a LATE-PCR.

It is anticipated that capture and removal of the single-stranded products of a LATE-PCR reaction will permit repeated rounds of product synthesis well beyond the number of rounds observed in a typical symmetric PCR reaction. For instance, we have shown that some LATE-PCR assays can be sustained for at least 100 thermal cycles in a closed tube reaction of 25-100 µl. This means that neither the Taq DNA polymerase, nor the reporter dye, nor the Excess Primer, nor the nucleotide precursors necessarily becomes limiting in a LATE-PCR reaction. This observation stands in contrast to the commonly held view in the scientific literature for symmetric PCR. For instance Liu and Saint write, "Since the reaction is performed in a closed tube containing a small amount of reaction mixture (25-50 µl), the reaction kinetics can be affected by all components in the reaction mixture, including reporter dye, nucleotide concentration, primer concentration, and initial copy number (or concentration) of template. Because the reporter dye, nucleotide, primer concentration, and enzymatic activity can become limiting to the rate of synthesis of amplicon, the rate of synthesis of amplicon will slow and eventually cease." (Liu, W. & Saint, D. A. (2002) "A New Quantitative Method of Real Time Reverse Transcription Polymerase Chain Reaction Assay Based on Simulation of Polymerase Chain Reaction Kinetics", Analytical Biochemistry 302: 52-59).

In contrast, our results demonstrate that the limits on amplification according to this invention are due to the fact that the concentration of the amplicon strand(s) reaches levels that allow them to effectively compete with their own primers (particularly the extension product of the Excess Primer competes with the Excess-Primer) for hybridization to the same target molecules. As shown earlier in the application, one means of sustaining production of the single-strand product is to optimize $(T_m^A - T_{m[0]}^X)$ to the range of 7-25° C., most preferably 12° C. However, optimization of $(T_m^A - T_{m[0]}^X)$ is not always possible, for instance if the amplicons are GC-rich or very long. Under these circumstances, capture and removal of the accumulating single strands can serve as a substitute for maintaining the specified melting-point differential between amplicon and Excess Primer. This enables the LATE-PCR to go on synthesizing single-strands for many cycles.

In another embodiment of the invention the LATE-PCR can be carried out under conditions in which one of the primers, most preferably the Excess Primer, is fixed to a solid matrix or surface such that each cycle of primer extension results in construction of an extended primer strand which remains attached to the solid surface, for example, a bead or the wall of the reaction chamber. It is anticipated that under these conditions $T_{m[0]}$ of the attached primer will be additionally dependent on the fact that the primer is not freely diffusible, as well as by the packing density of the primer on the surface, by the volume, and by the geometry of the space in which the reaction takes place. Therefore, the $T_{m[0]}$ of the primer, for instance $T_{m[0]}^X$, will have to be determined empirically under the experimental conditions of the reaction.

EXAMPLES

Example 1

Design of Primer Pairs, Tay Sachs HEX-A Gene

Rather than starting with an existing matched pair of symmetric PCR primers and making modifications to achieve a primer pair according to this invention, we prefer to design primer pairs using available computer software. We have successfully utilized the computer program Oligo® 6.0 (Oligo® Primer Analysis Software Manual, version 6.0 for Windows, Molecular Biology Insights, Inc. Sixth Edition, March 2000) to identify candidate primer pairs. To determine $T_{m[0]}$ for candidate primers using the "Nearest-Neighbor" method, we have successfully utilized the formula provided in the previous sections that relies on the Allawi and SantaLucia (1997) values for enthalpy and entropy. We designed a LATE-PCR primer pair for the identification of the wild-type and 1278+TATC allelic sequences in exon 11 of the alpha subunit of the beta-N-acetylhexosaminidase (HEX-A) gene. These alleles are associated with Tay-Sachs disease. The mutant allele, 1278+TATC, accounts for 82-90% of Tay-Sachs carriers within the Ashkenazi Jewish population. (For a recent review see *Advances in Genetics*, vol. 44, edited by Desnick and Kaback (2001), which is entirely devoted to Tay-Sachs disease). The Oligo® 6.0 program was used to identify a set of compatible primers for symmetric PCR amplification of a segment in HEX-A exon 11 containing nucleotide position 1278 (GenBank accession #: NM 000520). The search parameters were set to identify pairs of primers that would generate amplicons smaller than 100 base pairs. Among the candidate primer pairs, we chose a primer set whose sequences are given below in Table IV. According to the default settings of Oligo® 6.0 these primers have matching $T_m$'s (upper primer: 73.6° C.; lower primer: 73.0° C.). We then proceeded to calculate the primer $T_{m[1]}$ values at a standard concentration of 1 µM and to calculate the $T_{m[0]}$ values for the Excess and the Limiting Primers at concentrations of 1 µM and 25 mM, respectively (1:40 primer ratio; the monovalent cation concentration for these calculations was set to 0.07 M) using the Nearest Neighbor formula, as stated earlier. For convenience, the calculations of enthalpy and entropy with Allawi and SantaLucia (1997) nearest neighbor values can be done using the computer program, MELTING (Le Novere, N. (2001) "MELTING, Computing the Melting Temperature of Nucleic Acid Duplex," Bioinformatics 17: 1226-7). The results are given in Table IV. The above primer ratio and concentrations were chosen based on trials involving monitoring each amplicon strand with molecular beacons during asymmetric amplification and revealed that at 25 nM the Limiting Primer becomes depleted shortly after the reaction reaches the threshold cycle ($C_T$). The $C_T$ is thus reached before exponential amplification stops and linear amplification begins.

The Excess Primer was used at 1 µM to promote maximal synthesis of single-stranded DNA during the linear-phase of LATE-PCR. Table V shows the calculated $T_{m[1]}$ and $T_{m[0]}$ values. The matching $T_{m[1]}$ values makes this primer set suitable for symmetric PCR. The fact that $T_{m[0]}^L < T_{m[0]}^X$ makes this primer set unsuitable for use in LATE-PCR amplifications and assays.

TABLE IV

Initial primer pair suggested by Oligo ® 6.0

| Primer | Sequence | SEQ ID NO: | Conc. | $T_{m[1]}$ | Conc. | $T_{m[0]}$ |
|---|---|---|---|---|---|---|
| TSD1242S20 | 5'-CCTTCTCTCTGCCCCCTGGT-3' | 1 | 1 µM | 64.8° C. | 25 nM | 58.9° C. |
| TSD1301A22 | 5'-GCCAGGGGTTCCACTACGTAGA-3' | 2 | 1 µM | 64.3° C. | 1 µM | 643° C. |

The selected primers were then altered to meet criteria required for LATE-PCR amplification. Primer TSD1242S20 was lengthened at its 5' end using the endogenous HEX-A sequence, and Table V shows the results. In Table V, the nucleotides in the primer sequences that are presented in bold correspond to the sequences in Table IV. The two nucleotides in regular font at the 5' end of the Limiting Primer are the added nucleotides.

The original pair of primers listed in Table IV generate an 81 bp-long amplicon whose $T_m^A$ is 78.6° C. (according to % GC method: $T_m^A$=81.5+16.6 log [M]/(1+0.7[M])+0.41 (% G+% C)−500/length, at a 70 mM salt concentration: (Wetmur, J. G. (1991). "Applications of the Principles of Nucleic Acid Hybridization, *Crit Rev Biochem Mol Biol* 26: 227-259.) The modified primers used for LATE-PCR, Table V, generate an amplicon 83 bp-long that has a $T_m^A$=79.2° C. The difference ($T_m^A$-$T_{m[0]}^X$) is 15° C. (79.2−64.3=14.9, which rounds to 15° C.). This primer pair thus satisfies the conditions ($T_{m[0]}^L$-$T_{m[0]}^X$)≧0 and ($T_m^A$-$T_{m[0]}^X$)<18° C.

the initially selected Limiting Primer and by increasing its length to 30 nucleotides we obtained a final Limiting Primer having a $T_{m[0]}^L$=72° C.

Example 3

Design of LATE-PCR Primers for Cystic Fibrosis Gene

The criteria described herein for ($T_{m[0]}^L$-$T_{m[0]}^X$) and for ($T_m^A$-$T_{m[0]}^X$), alone and in combination, have demonstrable effects on PCR amplification. We have demonstrated certain effects utilizing primers, which we designate "CFTR" primers for amplifying the genomic sequence surrounding the Δ508 mutation, the most common cause of cystic fibrosis. For the tests reported in this example we have utilized Limiting Primers and Excess Primers from among those listed below in Table VI, which sets forth for each primer its nucleotide sequence and its $T_{m[0]}$ for a Limiting Primer concentration of

TABLE V

Primers modified to meet LATE-PCR specifications

| Primer | Sequence | SEQ ID NO: | Conc. | $T_{m[1]}$ | Conc. | $T_{m[0]}$ |
|---|---|---|---|---|---|---|
| TSD1240S22 | 5'-GCCCTTCTCTCTGCCCCCTGGT-3' | 3 | 1 µM | 69.4° C. | 25 nM | 64.0° C. |
| TSD1301A22 | 5'-GCCAGGGGTTCCACTACGTAGA-3' | 2 | 1 µM | 64.3° C. | 1 µM | 64.3° C. |

Example 2

Design of Primer Pairs, Human Beta Globin Gene

Another primer design is provided by the choice of primers for the detection of specific mutations in the human beta globin. The location of the primer sequences was chosen such that sites of the IVS1-110 and the codon 39 mutations known to cause beta thalassemia were included in the amplicon. The possible location of the 3' end of each primer was limited to regions without homology to the other members of the globin gene family to insure that the beta globin gene would be preferentially amplified. Once prospective sites were identified, those sequences were examined using the Oligo® 6.0 software and the region likely to yield a primer with a higher $T_{m[1]}$, was chosen for the Limiting Primer, in this case the lower strand sequence. A concentration of 50 nM was chosen for the Limiting Primer and the $T_{m[0]}^L$ of possible primers of different lengths was determined as described in Example 1. The $T_{m[0]}^X$ of possible Excess Primers at a concentration of 1000 nM was determined in the same manner. A Limiting Primer 26 nucleotides long with a $T_{m[0]}^L$=66° C. was initially selected, and an Excess Primer 28 nucleotides long with a $T_{m[0]}^X$=66° C. was chosen, that $T_{m[0]}^X$ being 15 degrees below the $T_m^A$ of 81° C. (amplicon of 191 base pairs, 52.4% GC). By including one A-to-G modification near the 5' end of 50 nM and an Excess Primer concentration of 1000 nM. In tests utilizing a hybridization probe against the single-stranded amplicon generated by extension of the Excess Primer, we used a molecular beacon modified with a quencher on one end and a fluorophore on the other end, having the following sequence 5'FAM—CG<u>CGCTTA</u>TCATCTTTGG-TGTTTCC<u>TATAGCGCG</u>—Dabcyl 3' (SEQ ID NO: 9) where the six nucleotides at each end (underlined) form the stem and therefore were not used to calculate $T_{m[0]}^P$. This probe had a $T_{m[0]}^P$ of 56° C. empirically measured under conditions that included 3 mM magnesium, 600 nM molecular beacon and 600 nM target.

TABLE VI

CFTR Limiting and Excess Primer Sequences

| primer name | Sequence | SEQ ID NO: | $T_{m[0]}$ |
|---|---|---|---|
| Limiting Primers: | | | |
| CF403 S18 | GATTATGCCTGGCACCAT | 4 | 51.1 |
| CF402 S19t | TGATTATGCCTGGCACCAT | 10 | 53.4 |
| CF402 S19 | GGATTATGCCTGGCACCAT | 6 | 54.1 |

TABLE VI-continued

CFTR Limiting and Excess Primer Sequences

| primer name | Sequence | SEQ ID NO: | $T_{m[0]}$ |
|---|---|---|---|
| CF400 S21t | CTTGATTATGCCTGGCACCAT | 11 | 55.2 |
| CF401 S20 | TGGATTATGCCTGGCACCAT | 12 | 56.2 |
| CF400 S21 | CTGGATTATGCCTGGCACCAT | 13 | 57.1 |
| CF399 S22 | CCTGGATTATGCCTGGCACCAT | 7 | 59.5 |
| CF398 S23 | TCCTGGATTATGCCTGGCACCAT | 14 | 60.9 |
| CF392 S29 | CAGTTTTCCTGGATTATGCCTGGCACCAT | 15 | 64.1 |
| CF391 S30 | TCAGTTTTCCTGGATTATGCCTGGCACCAT | 16 | 65.0 |
| Excess Primers: | | | |
| CF475 A16 | GACGCTTCTGTATCTA | 17 | 47.2 |
| CF476 A17 | TGACGCTTCTGTATCTA | 18 | 49.9 |
| CF477 A18 | ATGACGCTTCTGTATCTA | 19 | 50.7 |
| CF479 A20 | TGATGACGCTTCTGTATCTA | 20 | 54.2 |
| CF482 A23 | CTTTGATGACGCTTCTGTATCTA | 5 | 56.4 |
| CF483 A24 | GCTTTGATGACGCTTCTGTATCTA | 21 | 59.0 |
| CF488 A29 | GGCATGCTTTGATGACGCTTCTGTATCTA | 22 | 65.0 |

A first demonstration is reported in Table VII and FIGS. 2A and 2B. Two series of five PCR amplifications each were performed utilizing Excess Primer CF 479 A20 and one of five Limiting Primers identified in Table VII. In the first series all amplifications utilized the same annealing temperature, 52° C. (2° C. below $T_{m[0]}^{X}$). In the second series all amplifications used an annealing temperature 2° C. below $T_{m[0]}^{L}$. All amplifications were monitored with SYBR® Green, a fluorescent dye that binds to double-stranded DNA and, thus, monitors the production of double-stranded amplicon during the initial phase of amplification when both primers are present.

Table VII sets forth the difference ($T_{m[0]}^{L} - T_{m[0]}^{X}$) rounded to the nearest whole number following subtraction. Table VII also sets forth the mean $C_T$ from three replicates when the annealing temperature was 52° C. (first series) and when the annealing temperature was 2° C. below $T_{m[0]}^{L}$ (second series). The fluorescence readings (average of three replicates) from the first series are set forth in FIG. 2A (first series) and FIG. 2B (second series).

TABLE VII

Effect of ($T_{m[0]}^{L} - T_{m[0]}^{X}$)

| Limiting Primer | $T_{m[0]}^{L} - T_{m[0]}^{X}$ | Annealing Temperature First Series ° C. | Mean $C_T$ | Annealing Temperature Second Series ° C. | Mean $C_T$ |
|---|---|---|---|---|---|
| CF403 S18 | −3 | 52 | 35.1 | 49 | 34.4 |
| CF402 S19 | 0 | 52 | 34.7 | 52 | 34.2 |
| CF400 S21 | +3 | 52 | 33.8 | 54 | 34.7 |
| CF399 S22 | +5 | 52 | 32.0 | 57 | 32.4 |
| CF398 S23 | +7 | 52 | 30.8 | 59 | 32.4 |

Amplification mixtures included 1000 nM Excess Primer, 50 µM Limiting Primer, 0.4 mM each dNTP, 0.2×SYBR® Green (Molecular Probes), 3.5 mM MgCl$_2$, 0.06 Units/µl Platinum Taq DNA Polymerase (Invitrogen), 1×PCR buffer (20 mM Tris-HCl (pH 8.4), 50 mM KCl) and 1× Additive Reagent (1 mg/ml BSA, 750 mM trehalose, 1% Tween-20) and 600 picograms of human genomic DNA in a total volume of 25 µl. Amplification and fluorescence detection were done using a Cepheid Smart Cycler thermal cycling instrument with real-time fluorescence detection. An initial denaturation step of 3 minutes at 95° C. was followed by 60 cycles of: 95° C. for 5 seconds, 52° C. (or other specified annealing temperature) for 15 seconds, and 72° C. for 15 seconds with fluorescence acquisition.

FIG. 2A shows the mean real time fluorescence increase in samples from the first series. Each curve corresponds to reactions using primers with different ($T_{m[0]}^{L} - T_{m[0]}^{X}$) values as listed in Table VII. The earliest detection (lowest mean $C_T$ value) was obtained using the primer pair with the highest value ($T_{m[0]}^{L} - T_{m[0]}^{X}$) (+7, see curve 21). Mean $C_T$ values increased with each decrease in the value of ($T_{m[0]}^{L} - T_{m[0]}^{X}$) (+5, curve 22; +3, curve 23; +0, curve 24; −5, curve 25). Lower $C_T$ values demonstrate a higher rate of amplification (i.e., increased efficiency) during the exponential phase of the reaction. All samples eventually reached similar final fluorescence, that point corresponding to the completion of double-stranded DNA synthesis. (The continued synthesis of single-stranded DNA is not detected using this method.)

Gel electrophoresis revealed that each sample for which the value of ($T_{m[0]}^{L} - T_{m[0]}^{X}$) was between 0 and +7 yielded a similar quantity of specific amplicon. However, one of the three samples with ($T_{m[0]}^{L} - T_{m[0]}^{X}$) equal to −3 had considerably less specific amplicon and contained large amounts of non-specific products. The average level of non-specific product was lower in samples with ($T_{m[0]}^{L} - T_{m[0]}^{X}$) equal to 0 or +3, and extremely low in samples with ($T_{m[0]}^{L} - T_{m[0]}^{X}$) equal to +5 or +7. The results demonstrate that the increase in $T_{m[0]}^{L}$ several degrees above the annealing temperature determined as optimal for the Excess Primer does not increase the amount of detectable mis-priming by the Limiting Primer, and in fact, increases the specificity of the reaction.

FIG. 2B shows the results of samples with the same primer pairs as above, but with annealing done at 2° C. below $T_{m[0]}^{L}$. Again, each curve corresponds to reactions using primers with different ($T_{m[0]}^{L} - T_{m[0]}^{X}$) values as listed in Table VII. Curves 26 and 27, corresponding to samples where ($T_{m[0]}^{L} - T_{m[0]}^{X}$) equal to +5 or +7, respectively have a mean $C_T$ value that was lower than samples with delta-$T_m$ equal to +3 or lower (+3, curve 28; +0, curve 29; −3, curve 210) indicating the higher amplification efficiency in the former. Comparison of the mean $C_T$ values obtained at the different annealing temperatures for each primer pair shows that increasing the annealing temperature above the Excess Primer $T_{m[0]}$ results in only slight increase in mean $C_T$ values. However, the increased annealing temperature improves the specificity of the reaction even further, reducing the average level of non-specific product that is observed using gel electrophoresis. Conversely, lowering the annealing temperature of the primer pair with $T_{m[0]}^{L} - T_{m[0]}^{X}$ equal to −3 results in a slight reduction in mean $C_T$ value, but the average amount of specific amplicon was reduced and the average amount of non-specific product was increased. The reduced specificity of the reaction is presumably due to mis-priming by the Excess Primer at the lower annealing temperature. Thus, one advantage of having $T_{m[0]}^{L} > T_{m[0]}^{X}$ is that the true optimal annealing temperature for both primers can be set, sufficiently low to allow high amplification efficiency from the Limiting Primer, but sufficiently high to limit mis-priming from the Excess Primer that can generate non-specific products.

PCR reaction mixtures containing one of three of the Limiting Primers in Table VII, namely CF 403 S18, CF 402 S19 and CF 399 S22, but including a molecular beacon probe rather than SYBR® Green, were subjected to both series of amplifications. The first series (annealing temperature 52° C.) yielded mean $C_T$ values of 38.9, 37.6 and 36.8, respectively. The second series (annealing temperature 2° C. below $T_{m[0]}^L$) yielded mean $C_T$ values of 38.5, 38.6 and 38.9, respectively. When annealing was done at 2 degrees below $T_{m[0]}^L$, the lowest mean $C_T$ value was obtained for samples with $(T_{m[0]}^L - T_{m[0]}^X) = +5$ and the highest mean $C_T$ value was obtained for samples with $(T_{m[0]}^L - T_{m[0]}^X) = -3$, verifying the fact that amplification efficiency increases when Limiting Primer $T_{m[0]}^L$ is raised. Subsequent fluorescence increase was at similar rates in all groups.

Example 4

Design of Efficient LATE-PCR Primers

A set of PCR primers and a molecular beacon probe were designed for the ΔF508 allele of the cystic fibrosis gene based on published gene sequences. (Riordan et al. (1989) "Identification of the Cystic Fibrosis Gene: Cloning and Characterization of the Complementary DNA," Science 245: 1006-73). The primer and molecular beacon sequences were:

```
upper primer:
                                        (SEQ ID NO: 7)
5'-CCTGGATTATGCCTGGCACCAT-3' lower primer:
                                        (SEQ ID NO: 8)
5'-CCTGATGACGCTTCTGTATCTA-3' molecular beacon probe:
                                        (SEQ ID NO: 23)
5'-TET-CGCGCTAAAATATCATTGGTGTTTCCTAAGCGCG-
DABCYL-3',
``` where the underlined terminal sequences in the probe form a hairpin stem.

Primers were analyzed and varied to have difference $T_m$'s utilizing Oligo® 6.0 software. In this way we obtained primer pairs that the program (as is usual, in default mode) had calculated $T_m$'s as follows: either no difference in $T_m$ (both 65° C.; FIG. 3A), a 5° C. difference in $T_m$ (upper primer 70° C., lower primer 65° C.; FIG. 3B), or a 10° C. difference in $T_m$ (upper primer 75° C., lower primer 65° C.; FIG. 3C). Additionally, the primers were either equimolar (both 500 nM, curves 32, 34, and 36) or present at a 1:10 ratio (50 nM upper primer:500 nM lower primer, curves 31, 33, and 35). Fifteen microliters of concentrated PCR reagent mixture were added to each tube containing a lysed cell to yield a final sample volume of 25 microliters with final concentrations of 1×PCR buffer (Invitrogen, Carlsbad, Calif., USA), 3.75 mM MgCl$_2$, 0.25 mM dATP, 0.25 mM dCTP, 0.25 mM dGTP, 0.75 mM dUTP, primers as indicated, 1.2 µM molecular beacon, and 1.5 units Platinum Taq DNA polymerase (Invitrogen). Amplification and fluorescence detection were carried out in an ABI 7700 thermal cycling instrument with real-time fluorescence detection (Applied Biosystems, Foster City, Calif., USA). Thermal cycling consisted of an initial 5-minute denaturation at 95° C. followed by 4 cycles of 95° C. for 10 seconds, 55° C. for 2 minutes, and 72° C. for 30 seconds, followed by 21 cycles of 95° C. for 10 seconds, 55° C. for 30 seconds, and 72° C. for 30 seconds, followed by 35 cycles of 95° C. for 10 seconds, 52° C. for 30 seconds, and 72° C. for 30 seconds with fluorescence acquisition during the 52° C. step. Molecular beacons specific for the ΔF508 allele and for the normal allele were included in each reaction and were targeted to the lower primer-strand. Amplification and fluorescence detection were carried out in an ABI Prism 7700 Sequence Detector.

Results are shown in FIGS. 3A-3C. Results are plotted as the cycle number (X-axis) vs. the molecular beacon delta fluorescence units (Y-axis). FIG. 3A shows the results of replicates amplifications with the equal $T_m$ primers (65° C., 65° C.) in a symmetric PCR amplification having 1:1 ratio of primers (curve 32) and in an asymmetric amplification having a 1:10 ratio (curve 31). FIG. 3B shows the results of replicate amplifications with primers having $T_m$'s differing by 5° C. (70° C., 65° C.) with a 1:1 ratio of primers (curve 44) and with a 1:10 ratio (curve 33). FIG. 3C shows the results of replicate amplifications with primers having $T_m$'s differing by 10° C. (75° C., 65° C.) with a 1:1 ratio of primers (curve 36) and with a 1:10 ratio (curve 35).

The asymmetric reaction (1:10 primer ratio, curve 31) using equal $T_m$ primers results in a fluorescence signal that is delayed (later $C_T$), as compared to the symmetric reaction (equimolar primers, curve 32) (FIG. 3A). However, when a 5° C. difference in $T_m$ is introduced (FIG. 3B), the $C_T$ for the primers with a 1:10 ratio (curve 33) occurs much earlier, almost as early as for the equimolar primers (curve 34). Additionally, the final fluorescence signal for the primers with a 1:10 ratio (curve 33) is much higher than the signal for the equimolar primers (curve 34), and it has not plateaued, even at 60 cycles. When a 10° C. difference in $T_m$ (FIG. 3C) is introduced, the $C_T$ for the primers with a 1:10 ratio (curve 35) is the same as for the equimolar primers (curve 36), and the final fluorescence is much higher and does not plateau.

Example 5

Designing Primers Based on the Relationship Between $T_{m[0]}^X$ and $T_m^A$

LATE-PCR also takes into account the difference between $T_{m[0]}^X$ and $T_m^A$. $T_m^A$ is higher than $T_{m[0]}^X$, but if the difference between these two values is too great, then lower amounts of single-stranded product will be generated. A demonstration of this is reported in Table VIII and FIG. 6. We have demonstrated this using "CFTR" primer pairs for which $(T_{m[0]}^L - T_{m[0]}^X) = 0$° C., but those values are different in each set of replicate samples, and vary with respect to $T_m^A$. PCR amplification mixtures were prepared as described in Example 3, with molecular beacon probe added at a concentration of 600 nM rather than SYBR® Green. The thermal cycling profile was also the same, except that annealing was at 2° C. below $T_{m[0]}^L$ for the first 25 cycles, then shifted to 52° C. for an additional 50 cycles in order to monitor molecular beacon fluorescence under equivalent conditions for all samples.

TABLE VIII

Effect of varying $(T_m^A - T_{m[0]}^X)$ for $(T_{m[0]}^L - T_{m[0]}^X) = 0$

| Limiting Primer | Excess Primer | $T_m^A$ ° C. | $(T_m^A - T_{m[0]}^X)$ ° C. | Mean $C_T$ | early slope (cycles 45-60) | late slope (cycles 60-75) |
|---|---|---|---|---|---|---|
| CF403 S18 | CF477 A18 | 70 | 19 | 38.0 | 5.8 | 4.3 |
| CF402 S19 | CF479 A20 | 70 | 16 | 38.9 | 8.0 | 5.6 |
| CF401 S20 | CF482 A23 | 70 | 14 | 37.4 | 9.1 | 6.6 |

TABLE VIII-continued

Effect of varying ($T_m^A - T_{m[0]}^X$) for ($T_{m[0]}^L - T_{m[0]}^X$) = 0

| Limiting Primer | Excess Primer | $T_m^A$ °C. | ($T_m^A - T_{m[0]}^X$) °C. | Mean $C_T$ | early slope (cycles 45-60) | late slope (cycles 60-75) |
|---|---|---|---|---|---|---|
| CF399 S22 | CF483 A24 | 71 | 12 | 37.4 | 10.2 | 5.9 |
| CF391 S30 | CF488 A29 | 72 | 7 | 36.8 | 8.0 | 6.6 |

The average molecular beacon fluorescence for each group of 3 replicate samples is shown in FIG. 6. Each curve in FIG. 6 corresponds to a value ($T_m^A - T_{m[0]}^X$) from Table VIII. Mean $C_T$ values and rates of signal increase (slopes) are presented in Table VIII. Samples with ($T_m^A - T_{m[0]}^X$)=12° C. (curve 61) yielded the strongest beacon signal and presumably the largest quantity of single-stranded CFTR product in this series. Samples with ($T_m^A - T_{m[0]}^X$)=19° C. (curve 65) yielded the lowest signal. Samples with intermediate values of ($T_m^A - T_{m[0]}^X$)=14° C. (curve 62), or 16 (curve 64) yielded intermediate average signal intensity corresponding with that value. Samples with ($T_m^A - T_{m[0]}^X$)=7° C. (curve 63) also yielded intermediate final signal intensity, but displayed different kinetics than the other groups; the fluorescence remained relatively low for several cycles following initial detection, but the average rate of increase (slope) was among the highest during the final 15 cycles, suggesting that the Excess Primer in those samples continued to amplify efficiently as the concentration of the competing product strand increased. Such results may be advantageous for applications that require continued synthesis of the single stranded amplicon without generating non-specific product. Note that although the majority of samples (all groups) showed continued fluorescence increase to cycle 75 with only slightly reduced slopes, a few individual samples displayed greatly reduced slope or reached a plateau during the last 5 to 10 cycles. This may be due to Product Evolution, or to the generation of non-specific product in samples with matched primer $T_{m[0]}$.

The benefits of simultaneously optimizing ($T_{m[0]}^L - T_{m[0]}^X$) and ($T_m^A - T_{m[0]}^X$) are illustrated in Table IX and FIG. 7. Each pair of primers in this experiment was designed such that ($T_{m[0]}^L - T_{m[0]}^X$)=+5° C. to +6° C. The values for ($T_m^A - T_{m[0]}^X$) ranged from +13 to +23. Curves in FIG. 7 correspond to amplification curves using primers with the values of ($T_m^A - T_{m[0]}^X$) listed in Table X. Sample preparation, amplification, and detection were done as described above.

TABLE IX

Effects of Varying ($T_m^A - T_{m[0]}^X$) for ($T_{m[0]}^L - T_{m[0]}^X$) = +5-6

| Limiting Primer | Excess Primer | $T_m^A$ | $T_m^A - T_{m[0]}^X$ | Mean $C_T$ | early slope (cycles 45-60) | late slope (cycles 60-75) |
|---|---|---|---|---|---|---|
| CF402 S19t | CF475 A16 | 70 | 23 | 43.0 | 2.3 | 3.6 |
| CF400 S21t | CF476 A17 | 70 | 20 | 41.3 | 4.3 | 4.3 |
| CF401 S20 | CF477 A18 | 70 | 19 | 38.7 | 4.2 | 3.8 |
| CF399 S22 | CF479 A20 | 71 | 17 | 38.5 | 7.6 | 5.7 |
| CF392 S29 | CF483 A24 | 72 | 13 | 38.1 | 11.3 | 7.6 |

It is evident from the kinetic plots in FIG. 7 and Table IX that the highest molecular beacon signals (cycles 35-60) were in samples with ($T_m^A - T_{m[0]}^X$)=13 (curve 71), indicating efficient single strand synthesis. The mean intensity of the molecular beacon signal decreased with each increase in ($T_m^A - T_{m[0]}^X$) to values of 17 (curve 72), 19 (curve 73), 20 (curve 74), and 23 (curve 75). In contrast to the series in the FIG. 6, none of these samples showed an amplification plateau, illustrating another advantage of having ($T_{m[0]}^L - T_{m[0]}^X$)≥+5° C. Electrophoresis of these samples revealed only the specific single- and double-stranded amplicon. Non-specific product was not detected, even in the sample group for which annealing temperature was lowered from 59° C. to 52° C. for cycles 26 to 75.

Example 6

Kit for Real-Time LATE-PCR Assay

A LATE-PCR reagent has been designed for use in the detection of the normal and ΔF508 alleles of the human cystic fibrosis gene during preimplantation genetic diagnosis (PGD). The kit is modular; that is, it contains DNA polymerase in one package and all other reagents and materials in another package. It will be appreciated that the primers and probes together comprise an oligonucleotide set, which can be marketed as a separate product. The kit, its use, and the assay performed with the kit, which we call the "CFΔ508 Kit," are described in this example in a format that might appear on a product insert accompanying the kit.

A Diagnostic Test to Genotype a Diploid Human Cell at the F508 Region of the CFTR Gene
10 Assay Kit
For In Vitro Diagnostic Use Only
Important: Read All Instructions Before Starting this Test.
Intended Use The CFΔF508 Kit is designed to demonstrate whether one or a plurality of nucleated diploid human cells are genetically homozygous normal (Normal/Normal), heterozygous (Normal/ΔF508), or homozygous affected (ΔF508/ΔF508). These determinations are carried out in vitro by collecting and testing one or more cells, or the DNA derived from such cells. The knowledge derived from such tests can be used to make decision about the life of an individual or the healthcare management of such an individual. For instance those carried out on a single cell from a human embryo, or the cells of a fetus may help the prospective parents decide whether or not a particular embryo should be implanted, or whether or not termination of a pregnancy should be considered. In another instance, postnatal knowledge about an individual's genotype can be used to help optimize the healthcare and life style of said individual.
Explanation Cystic fibrosis (CF) is the most common inherited disease among Caucasian populations with an incidence of about 1 in 2500 births (Welsh et al., 1995). The conditions caused by mutations in the CF gene, which functions as a chloride channel in the lungs and other tissue. Mutations in the CF gene have phenotypes that range from mild to life threatening. A 3-basepair deletion within the CF gene, designated ΔF508, accounts for nearly 70% of CF cases and causes severe manifestations of the disease. It results in the absence of phenylalanine at position 508 of the cystic fibrosis transmembrane conductance regulator protein (CFTR) and this error prevents normal processing and translocation of the polypeptide chain to apical membranes of epithelial cells (Cheng et al., 1990). The first tests for ΔF508 in single cells used nested PCR to amplify the requisite sequence followed by verification of the final product by either restriction enzyme digestion (Coutelle et al., 1989), hybridization to allele-specific oligonucleotides (Wu et al., 1993), or heteroduplex formation (Liu et al., 1993; Avner et al., 1994). The first clinical reports of PGD for CF also utilized heteroduplex analysis of the PCR products (Handyside et al., 1992; Verlinsky et al., 1992; Ao et al., 1996). More recent PCR assays have used fluorescently labeled primers to increase sensitivity and reduce the rate of allele drop out (ADO), a failure to amplify one allele from a heterozygous cell (Findlay et al., 1995; Verlinsky and Kuliev, 2000; Goossens et al., 2000). When this approach is employed, the fluorescently labeled products are separated and identified by capillary electrophoresis after PCR amplification is finished.

Couples in which both individuals carry a mutant copy of the ΔF508 allele have a one in four chance of having an afflicted child. One diagnostic alternative available to such couples, known as preimplantation genetic diagnosis (PGD), offers such couples an opportunity to determine the genetic composition of their embryos before starting a pregnancy. If one or more embryos tests negative for the ΔF508 allele or heterozygous for the ΔF508 allele the couple than has an opportunity to start a pregnancy based on knowledge that they have a very low probability of having an afflicted fetus or baby. However, PGD is technically difficult because each assay has to be carried out on a single cell recovered from a cleavage-stage embryo. Prenatal diagnosis provides an alternative to PGD. Prenatal diagnosis for CF is carried out on amniotic cells recovered by amniocentesis, a technique for collecting amniotic fluid and cells surrounding a fetus in an ongoing pregnancy. A fetus afflicted with CF can be aborted, if the women so chooses within the second trimester of her pregnancy. Alternatively, CF can be tested for and diagnosed postnatally using blood cells and/or other types of cells. Diagnosis of an afflicted individual is very important for providing rapid and optimal healthcare.

In this kit, we describe the use of a LATE-PCR, real-time assay with molecular beacons to identify the normal and ΔF508 alleles of cystic fibrosis in single human cells.

Principle of the Method

The kit assay makes use of a fluorescently-labeled DNA probe known as a Molecular Beacon to detect specific DNA sequences amplified via a modified form of the polymerase chain reaction (PCR)[1,2], hereafter known as LATE-PCR. The kit contains two specific Molecular Beacon Probes, one that fluoresces yellow and is configured to hybridize to the normal allele of the CFTR gene and one that fluoresces red and is configured to hybridize to the ΔF508 allele of the CFTR gene. Each Molecular Beacon Probe has a 6 base-pairs long stem and only fluoresces in the presence of its specific target sequence. A single nucleotide mismatch is sufficient to prevent fluorescence of the Molecular Beacon Probe. LATE-PCR reactions begin with symmetric amplification of both strands and then abruptly switch to linear amplification of a single strand. Because all copies of the accumulating target strand are single-stranded, they are readily detected with a Molecular Beacon Probe. These characteristics provide a high signal to noise ratio and enhance the sensitivity and accuracy of the assay.

The kit contains two primers that together amplify two amplicons approximately 85 base pairs long in region of the CFTR gene that includes the F508 region. The sequence of the Limiting primer is 5'CCTGGATTATGCCTGGCACCAT 3' (SEQ ID NO: 7); it is used at a concentration of 50 nM. The sequence of the Excess primer is 5' CCTTGATGACGCT-TCTGTATCTA 3'(SEQ ID NO: 24); it is used at a concentration of 1,000 nM. These primers have melting temperatures ($T_m$) that are approximately matched at the initial concentrations, as calculated using a nearest neighbor formula (Allawi and SantaLucia, 1997), providing optimal efficiency and specificity for DNA amplification.

Materials Provided

The contents of the CFΔF508 Kit test kit are sufficient to perform an analysis of ten individual samples, each containing 1-10,000 cells. All samples, including control samples should be prepared on the same day. Do not refreeze or reuse any tubes or reagents. Discard unused materials.

10 Sample Reaction Tubes containing Cell Lysis Buffer
    2 No Cell Control Reaction Tubes
    2 Positive Control Reaction Tubes with DNA heterozygous for ΔF508
    16 Replacement Caps for Reaction Tubes
    Support Base for Reaction Tubes
    1 PCR Buffer Tube (235 μl) 60 ml Cell Wash Buffer
    30 ml Final Wash Buffer
    12 Sterile transfer pipets
    Form for cell sample identification
    Disposal Bag for used Reaction Tubes Additional Materials Required inverted microscope or dissecting microscope equipped with micromanipulator or other device for picking up single cells or other small samples.
    thermal cycler with fluorescence detection: (ABI PRISM 7700 or equivalent) Laminar flow hood or non-circulating containment hood
    table-top microcentrifuge for 0.2 ml tubes
    micropipets or other device for cell isolation and transfer to tubes
    sterile petri dishes
    powder-free gloves
    lab coat, surgical mask and cap
    pipettors and sterile pipet tips with filter
    Platinum Taq DNA Polymerase (Invitrogen) [separate kit module]

Storage and Handling

Store the CFΔF508 Kit reagents in a non-frost-free freezer (−20° C.). Avoid repeated thawing and refreezing. Protect the PCR Buffer Tube from exposure to light during storage. Handle the tubes and bottles with clean, powder-free gloves.

General Precautions

For Laboratory In Vitro Diagnostic Use Only
    Components of the test must not be used for any purpose other than described in these instructions
    Improper handling of the components can lead to contamination and misdiagnosis of samples
    Improper storage of reagents could affect reactions and prevent diagnosis of samples
    Do not use the enclosed reagents after the expiration date shown on the box Contamination Control Precautions The CFΔF508 Kit has been designed to minimize the risk of contamination. The following steps must be taken to insure that risk remains at an acceptable low level.* Open Reaction Tubes and the PCR Buffer Tube only in a laminar flow hood or non-circulating containment hood.
    Treat surfaces with 10% bleach or sterilize with UV light prior to use.
    Wear a clean lab coat, surgical mask, cap, and powder-free gloves.
    Handle all kit components ONLY with gloved hands.
    Gloves should be changed after touching any object that might be contaminated with human cells or DNA (e.g., any surface outside the treated area).
    EXTREME CARE must be taken to avoid transferring unintended cells to the assay tube. These cells this could provide template for LATE-PCR amplification and Molecular Beacon fluorescence.

Use mechanical pipetters that are dedicated for PCR setup and are not used for other purposes.

Use sterile pipet tips with filters.

Discard used pipet tips immediately after single use.

NEVER reintroduce a used pipet tip into a Reaction Tube or the PCR Reagent Tube.

PCR should be done in a location separate from cell biopsy and sample preparation.

DO NOT open the Reaction Tubes at anytime after removing them from the thermal cycler following PCR amplification. Opening tubes releases DNA-containing aerosols that can contaminate the laboratory and could jeopardize all subsequent assays.

Place used Reaction Tubes in the disposal bag, seal completely, and dispose of properly in accordance with any local, state or federal regulations. Only autoclave waste if required by law. If autoclaving is required, it should NOT be done in or near the labs used for sample preparation or PCR.

CFΔ508 Kit Assay Procedure

Pre-Biopsy Setup

STEP A. Place the support base containing 2 No Cell Control Reaction Tubes and 10 Sample Reaction Tubes on ice. After thawing is complete, briefly centrifuge all tubes to insure that liquid contents are at the bottom. Return the tubes to ice, placing them in the proper positions of the support base. Keep all Reaction Tubes closed at this time.

STEP B. On the enclosed Cell Identification Form, record the designation for each sample to be tested next to the number/color code of the Sample Reaction Tube that will be used for that embryo. DO NOT place any marks directly on tubes or caps as this interferes with fluorescence detection.

STEP C. Working in a containment hood, prepare two petri dishes with Cell Wash Buffer and one petri dish with Final Wash Buffer (0.5 ml to 3.0 ml of buffer per dish) for each embryo to be biopsied. Make sure that each dish is properly labeled.

Biopsy and Cell Wash: Complete Steps D-F Before Repeating with Another Embryo.

STEP D. Care must be taken to avoid transferring non-embryonic cells. In particular in the case of embryo biopsy for PGD, all sperm or cumulus cells surrounding or adhering to the embryo must be removed as completely as possible prior to starting the biopsy. Perform embryo biopsy using any established technique, including direct aspiration[3], zona drilling and aspiration[4], zona drilling and displacement[5], or zona cutting with laser and aspiration[6]. One or two intact blastomeres should be isolated from each embryo. Blastomeres damaged during biopsy or subsequent wash steps should not be used for diagnosis.

STEP E1—in cases of embryo biopsy. The following wash steps are important to remove components of culture media that can interfere with cell lysis, PCR, and fluorescence detection. Transfer the microdrop containing the blastomere(s) to the hood containing the dissecting microscope. While observing under the microscope, use a sterile Transfer Pipet (provided in the Kit) to move one biopsied blastomere into the first dish containing unused Cell Wash Buffer, as follows: A) aspirate a small amount of Cell Wash Buffer into the transfer pipet; B) aspirate the blastomere into the tip of the pipet; C) Carefully expel the blastomere into the first dish containing Cell Wash Buffer. As soon as the blastomere exits the pipet, move the pipet to another region of the dish to expel remaining Cell Wash and rinse the pipet. Repeat this procedure to transfer the blastomere into the second dish containing unused Cell Wash Buffer, followed by the third dish containing Final Wash Buffer. All washes should be brief.

STEP E2—in cases other than human embryos. Cells are placed in a 200 μl tube and washed three times in 10 volumes of Cell Wash Buffer by means of gentle centrifugation, aspiration of the supernatant, and resuspension in Final Wash Buffer. All washes should be brief and can be performed at 4° C. if desired.

Cell Lysis

STEP F. Use the transfer pipet to pick up the blastomere, or other type of cell, in a small volume of Final Wash Buffer. The aspirated fluid should not extend more than 1 cm above the tip of the pipet. Open the Sample Reaction Tube that has been designated for that blastomere and place the cap on a sterile surface. Avoid touching the inner portion of the cap. Place the tip of the transfer pipet containing the cell directly into the buffer in the Sample Reaction Tube and expel the contents of the pipet. Close the tube. If bubbles are present, or buffer droplets are present on the sides of the tube, the sample should be centrifuged briefly (a few seconds). Place the Sample Reaction Tube on ice as soon as possible after adding the blastomere. Samples MUST remain on ice until Step I. DO NOT leave the sample at room temperature as it will result in suboptimal reactions that could prevent accurate diagnosis.

STEP G. Insure that the correct cell identification has been recorded with the Sample Reaction Tube number. If a second cell has been obtained from the same source, it should be washed and transferred to a separate Sample Reaction Tube using a new transfer pipet. Discard all used pipets and wash dishes.

STEP H. Repeat steps D through G using new pipets and wash dishes for each embryo tested. Transfer an equivalent volume of Final Wash Buffer into both of the No Cell Control Reaction Tubes.

STEP I. Preheat the thermal cycler block to 50° C. The block must be equipped with a heated cover designed to prevent condensation on the lid of the tubes. Place all Sample Reaction Tubes, as well as both No Cell Control Reaction Tubes into the preheated block. Incubate at 50° C. for 30 min, then 95° C. for 15 minutes. Once the block has cooled to room temperature, remove and examine each Reaction Tube. If condensation is present on the cap or sides of tubes, the samples may not provide adequate amplification for diagnosis. Place tubes on ice as described in Step A. During the incubation period of Step I, continue with Steps J and K.

PCR Setup (Steps K and L Should Either be Carried Out in a Different Laminar Flow Hood or Noncirculadng Containment Hood than that Used for Steps D-H, or the Hood Used for Steps D-H Should be Cleared of all Unnecessary Materials and Wiped Down with a 10% Bleach Solution Prior to Using it for Steps K and L)

STEP J. [LATE-PCR with Hotstart]

Add 4.8 μl of Platinum Taq DNA Polymerase (5 Units/μl) to the PCR Buffer Tube and mix thoroughly to insure even distribution of the enzyme.

STEP K. Thaw the two Normal/ΔF508 heterozygous DNA Control Tubes by placing them in the support rack on ice. Add each Sample Reaction Tube and each No Cell Control Reaction Tube to the support rack once the lysis incubation (step J) is complete.

STEP L. Open the first Sample Reaction Tube and add 15 μl of PCR Buffer containing added Taq DNA polymerase. Recap the tube immediately using a Replacement Cap. Discard the old cap and used pipet tip. Repeat this step for each Reaction Tube, including the two Positive Control Tubes and the two No Cell Control Tubes. All Control Tubes must be analyzed in parallel with unknown cell samples for accurate interpretation of test results. As an added precaution against cross contamination, it is recommended that gloves be changed after each sample.

PCR and Fluorescence Detection

STEP M. [Recommended Cycling Parameters]

Load the tubes into a thermal cycler with fluorescence detection. The following program is based on the ABI PRISM 7700 Sequence Detector (Applied Biosystems):

Stage 1. 95° C., 3 minutes (1 repeat)
Stage 2. 95° C., 10 seconds, 55° C. 30 seconds, 72° C. 30 seconds (25 repeats)
Stage 3. 95° C., 10 seconds, 52° C. 30 seconds, 72° C. 30 seconds (35 repeats)
Set fluorescence acquisition for FAM and TET during the 52° C. step.
Set sample volume at 25 µl.
Select the block positions that are used and type in the correct sample identifications.

STEP N. Never open the Reaction Tubes following amplification as this may result in contamination of the laboratory that could jeopardize all subsequent assays. Following the completion of PCR, remove all Reaction Tubes without opening and immediately place them in the disposal bag. Completely seal the bag and dispose of properly in accordance with any local, state or federal regulations. If autoclaving is required, seal the bag with as little air as is reasonably possible, then proceed to autoclave at a site distant from the laboratory, in an autoclave that is not used to prepare any other materials used in the laboratory.

Analysis and Interpretation of Assay Results

The following description is appropriate for an ABI PRISM 7700 Sequence Detector (Applied Biosystems); parameters appropriate for other machines are currently unknown. Set a threshold value of 200 units and a baseline start at cycle 3 and stop at cycle 12 of stage 3 (cycles 28 and 37 of the overall reaction) for each reporter dye (FAM and TET) in the analysis window of the ABI 7700. These values are used to compute the threshold cycle ($C_T$) for fluorescence detection in each sample.

The range of $C_T$ values and Final Fluorescence values required for scoring positive for the normal allele (FAM signal) and for the ΔF508 mutant allele (TET signal) are provided on the separate Product Analysis Certificate and are based on testing for each lot. Values above threshold, but below these required values indicate the possibility of contamination or inadequate cell lysis. Samples generating such values should not be scored and embryos should not be transferred based on the test results.

Limitations of the Test

The CFΔF508 Kit has been designed to use Platinum Taq DNA Polymerase (Invitrogen) and the ABI PRISM 7700 Sequence Detector (Applied Biosystems). Use of other DNA polymerase with hot start or other thermal cyclers with fluorescence detection may be possible, but must be optimized by the user prior to testing cells from embryos. This kit is designed to identify the ΔF508 mutation and the normal allele sequence in that region of the CFTR gene. Other mutations in the CFTR gene cannot be detected using this kit.

Chromosomal mosaicism is present in some embryos obtained from IVF and is common in embryos with poor morphology. A single biopsied blastomere therefore may not be representative of the genetic makeup of the embryo.

Some human embryos contain anucleate cells that will give negative results if used in this assay. The most accurate results will be obtained if nuclei are observed in biopsied blastomeres. A blastomere should not be used if signs of cell lysis are observed following biopsy, since cell damage may include DNA degradation.

REFERENCES

[1]Tyagi, S. and Kramer, F. R. (1996) Nature Biotechnology 14, 303-308
[2]Piatek et al. (1998) Nature Biotechnology 16, 359-363
[3]Wilton, L. J. and Trounson, A. O. (1989) Biology of Reproduction 40, 145-152
[4]Hardy, K. et al. (1990) Human Reproduction 5, 708-714
[5]Pierce, K. E. et al. (1997) Human Reproduction 12, 351-356
[6]Boada et al. (1998) J. Assist Reprod Genet 15, 302-307

CFΔ508 Kit Components and Compositions
Reaction Tubes
0.2 ml Optical Tubes from Perkin Elmer (Pt # N801-0933) with optical caps (Pt # N801-0935)
Composition of Cell Lysis Buffer (Sample and No Cell Reaction Tubes):
100 µg/ml proteinase K (Roche Molecular Biochemicals)
5 µM Sodium Dodecylsulfate
10 mM Tris, pH 8.3 (Trizma pre-set crystals, Sigma)
molecular-grade water
Composition of Sample Contained in Normal/Δ508 Control Reaction Tube:
60 picograms human DNA heterozygous for the Δ508 allele of the CF gene.
5 µM Sodium Dodecylsulfate
10 mM Tris, pH 8.3 (Trizma pre-set crystals, Sigma)
molecular-grade water to 10 microliter final volume
Composition of Cell Wash Buffer:
Phosphate buffered saline without $Ca^{++}$ or $Mg^{++}$ (Sigma, Cat. No. D-8537)
0.1% Polyvinylpyrrolidone (Sigma, Cat. No. PVP40)
Composition of Final Wash Buffer:
Phosphate buffered saline without calcium or magnesium
0.01% Polyvinylpyrrolidone
Composition of PCR Buffer:
1.67×PCR Buffer (Invitrogen)
6.25 mM $MgCl_2$
0.42 mM each of the four deoxyribonucleotide triphosphates (dCTP, dTTP, CDATP, dGTP)
0.083 µM Limiting Primer
1.67 µM Excess Primer
1.0 µM each Molecular Beacon (2 total)
Molecular-grade water to final volume of 235 microliters
CF Primers:

[SEQ ID NO: 7]
Limiting: 5' CCTGGATTATGCCTGGCACCAT 3'

[SEQ ID NO: 24]
Excess: 5' CCTTGATGACGCTTCTGTATCTA 3'

Normal Allele Molecular Beacon:

[SEQ ID NO: 9]
5' FAM-CGCGCTTATCATCTTTGGTGTTTCCTATAGCGCG-Dabcyl 3'

Δ508 Allele Molecular Beacon:

[SEQ ID NO: 23]
5' TET-CGCGCTAAAATATCATTGGTGTTTCCTAAGCGCG-Dabcyl 3'

We claim:

1. An oligonucleotide set comprising a pair of polymerase chain reaction (PCR) primers in a single buffer for amplifying a selected DNA amplification target sequence, said target sequence and primers defining a double-stranded amplification sequence bracketed by the primer pair, said amplification sequence having a melting temperature ($T_m^A$), wherein $T_m^A = 81.5 + 0.41(\% \text{ G} + \% \text{ C}) - 500/L + 16.6 \log 0.07/(1+0.7 (0.07))$, where L is the length in nucleotides, comprising a limiting primer and an excess primer, wherein the ratio (X) of limiting primer to excess primer is not more than 0.05, wherein X=(concentration of limiting primer)/(concentration of excess primer); wherein the limiting primer has a melting temperature ($T_m^L$), wherein $T_m^L = \Delta H/(\Delta S + R \ln(X*10^{-6}/2)) - 273.15 + 12 \log 0.07$, and the excess primer has a melting temperature ($T_m^X$), wherein $T_m^X = \Delta H/(\Delta S + R \ln(10^{-6}/2)) - 273.15 + 12 \log 0.07$, wherein the difference between $T_m^L$ and $T_m^X$ is equal to or higher than 0° C. and, if the limiting primer is not fully complementary to the amplification target sequence, the melting temperature of the imperfect hybrid between the limiting primer and the amplification target sequence ($T_m^{LA}$), wherein $T_m^{LA} = \Delta H/(\Delta S + R \ln(X*10^{-6}/2)) - 273.15 + 12 \log 0.07$, is not more than 5° C. below the melting temperature of the excess primer; and wherein the melting temperature of the amplification sequence does not exceed the melting temperature of the excess primer by more than 18° C., where R is the universal gas constant, and where $\Delta H$ is enthalpy and $\Delta S$ is entropy.

2. The oligonucleotide set according to claim 1 wherein the melting temperature of the limiting primer exceeds the melting temperature of the excess primer by at least 3° C.

3. The oligonucleotide set according to claim 2 wherein the melting temperature of the amplification sequence exceeds the melting temperature of the excess primer by 7-15° C.

4. The oligonucleotide set according to claim 1 wherein the melting temperature of the amplification sequence exceeds the melting temperature of the excess primer by 7-15° C.

5. An oligonucleotide set comprising a pair of polymerase chain reaction (PCR) primers in a single buffer for amplifying a selected DNA amplification target sequence, said target sequence and primers defining a double-stranded amplification sequence bracketed by the primer pair, said amplification sequence having a melting temperature ($T_m^A$), wherein $T_m^A=81.5+0.41(\% \text{ G}+\% \text{ C})500/L+16.6 \log 0.07/(1+0.7(0.07))$, where L is the length in nucleotides, comprising a limiting primer and an excess primer,
   wherein the ratio (X) of limiting primer to excess primer is not more than 0.2, wherein X=(concentration of limiting primer)/(concentration of excess primer); wherein the limiting primer has a melting temperature ($T_m^L$), wherein $T_m^L=\Delta H/(\Delta S+R \ln (X*10^{-6}/2))-273.15+12 \log 0.07$, and the excess primer has a melting temperature ($T_m^X$), wherein $T_m^X=\Delta H/(\Delta S+R \ln(10^{-6}/2))-273.15+12 \log 0.07$, wherein $T_m^L$ exceeds $T_m^X$ by at least 3° C. and, if the limiting primer is not fully complementary to the amplification target sequence, the melting temperature of the imperfect hybrid between the limiting primer and the amplification target sequence ($T_m^{LA}$), wherein $T_m^{LA}=\Delta H/(\Delta S+R \ln(X*10^{-6}/2))-273.15+12 \log 0.07$, is not more than 5° C. below the melting temperature of the excess primer; and wherein the melting temperature of the amplification sequence does not exceed the melting temperature of the excess primer by more than 18° C., where R is the universal gas constant, and where $\Delta H$ is enthalpy and $\Delta S$ is entropy.

6. The oligonucleotide set according to claim 5, wherein X is not more than 0.1.

7. An oligonucleotide set comprising, in a single buffer,
   a) a pair of polymerase chain reaction (PCR) primers in a single buffer for amplifying a selected DNA amplification target sequence, said amplification target sequence and said primers defining a double-stranded amplification sequence bracketed by the primer pair, said amplification sequence having a melting temperature ($T_m^A$), wherein $T_m^A=81.5+0.41(\% \text{ G}+\% \text{ C})-500/L+16.6 \log 0.07/(1+0.7(0.07))$, where L is the length in nucleotides, comprising a limiting primer and an excess primer, wherein the concentration ratio (X) of limiting primer to excess primer is not more than 0.2, wherein X=(concentration of limiting primer)/(concentration of excess primer); and
   b) at least one labeled hybridization probe consisting essentially of conventional nucleotides that hybridizes to the same strand of the amplification sequence as does the limiting primer and that emits a detectable signal upon hybridization, wherein Y is the concentration ratio of the probe to the excess primer, wherein Y=(concentration of probe)/(concentration of excess primer) and wherein the melting temperature of the at least one probe-amplification sequence hybrid ($T_m^{PA}$) measured at a concentration of Y μM is at least 5° C. below the melting temperature of the limiting primer ($T_m^L$), wherein $T_m^L=\Delta H/(\Delta S+R \ln(X*10^{-6}/2))-273.15+12 \log 0.07$, where R is the universal gas constant, and where $\Delta H$ is enthalpy and $\Delta S$ is entropy.

8. The oligonucleotide set according to claim 7 wherein the difference between $T_m^L$ and the melting temperature of the excess primer ($T_m^X$), wherein $T_m^X=\Delta H/(\Delta S+R \ln(10^{-6}/2))-273.15+12 \log 0.07$, is equal to or higher than 0° C. and, if the limiting primer is not fully complementary to the amplification target sequence, the melting temperature of the imperfect hybrid between the limiting primer and the amplification target sequence ($T_m^{LA}$), wherein $T_m^{LA}=\Delta H/(\Delta S+R \ln(X*10^{-6}/2))-273.15+12 \log 0.07$, is not more than 5° C. below the melting temperature of the excess primer.

9. The oligonucleotide set according to claim 8, wherein the melting temperature of the limiting primer exceeds the melting temperature of the excess primer by at least 3° C.

10. The oligonucleotide set according to claim 8, wherein X is not more than 0.1.

11. The oligonucleotide set according to claim 8, wherein the melting temperature of the amplification sequence exceeds the melting temperature of the excess primer by not more than 18° C.

12. The oligonucleotide set according to claim 11, wherein the melting temperature of the at least one probe-amplification sequence hybrid is at least 10° C. below the melting temperature of the limiting primer.

13. The oligonucleotide set according to claim 8, wherein said at least one probe comprises a first hybridization probe specific for a first allele and a second hybridization probe specific for a second allele.

14. The oligonucleotide set according to claim 8, wherein the melting temperature of the at least one probe-amplification sequence hybrid is at least 10° C. below the melting temperature of the limiting primer.

15. The oligonucleotide set according to claim 7, wherein said at least one probe comprises a first hybridization probe specific for a first allele and a second hybridization probe specific for a second allele.

16. The oligonucleotide set according to claim 7, wherein said at least one hybridization probe is a DNA probe.

17. The oligonucleotide set according to claim 7, wherein the melting temperature of the at least one probe-amplification sequence hybrid is at least 10° C. below the melting temperature of the limiting primer.

18. An oligonucleotide set comprising, in a single buffer,
   a) a pair of polymerase chain reaction (PCR) primers in a single buffer for amplifying a selected DNA amplification target sequence, said amplification target sequence and said primers defining a double-stranded amplification sequence bracketed by the primer pair, said amplification sequence having a melting temperature ($T_m^A$), wherein $T_mA=81.5+0.41(\% \text{ G}+\% \text{ C})-500/L+16.6 \log 0.07/(1+0.7(0.07))$, where L is the length in nucleotides, comprising a limiting primer and an excess primer, wherein the concentration ratio (X) of limiting primer to excess primer is not more than 0.2, wherein X=(concentration of limiting primer)/(concentration of excess primer); and
   b) at least one labeled hybridization probe that hybridizes to the same strand of the amplification sequence as does the limiting primer and that emits a detectable signal upon hybridization, wherein Y is the concentration ratio of the probe to the excess primer, wherein Y=(concentration of probe)/(concentration of excess primer), and wherein the melting temperature of the at least one probe-amplification sequence hybrid measured at a concentration of Y μM is at least 10° C. below the melting temperature of the limiting primer ($T_m^A$), wherein $T_m^A=\Delta H/(\Delta S+R \ln(X*10^{-6}/2))-273.15+12 \log 0.07$, where R is the universal gas constant, and where $\Delta H$ is enthalpy and $\Delta S$ is entropy.

19. A kit of reagents for performing a homogenous polymerase chain reaction (PCR) assay for at least one pre-selected DNA amplification target sequence comprising a thermostable DNA polymerase, dNTP's and, for each amplification target sequence, an oligonucleotide set comprising, in a single buffer,
- a) a pair of polymerase chain reaction (PCR) primers in a single buffer for amplifying a selected DNA amplification target sequence, said amplification target sequence and said primers defining a double-stranded amplification sequence bracketed by the primer pair, said amplification sequence having a melting temperature ($T_m^A$), wherein $T_m^A = 81.5 + 0.41(\% \text{ G} + \% \text{ C}) - 500/L + 16.6 \log 0.071(1+0.7(0.07))$, where L is the length in nucleotides, comprising a limiting primer and an excess primer, wherein the concentration ratio (X) of limiting primer to excess primer is not more than 0.2, wherein X=(concentration of limiting primer)/(concentration of excess primer); and
- b) at least one labeled hybridization probe consisting essentially of conventional nucleotides that hybridizes to the same strand of the amplification sequence as does the limiting primer and that emits a detectable signal upon hybridization, wherein Y is the concentration ratio of the probe to the excess primer, wherein Y=(concentration of probe)/(concentration of excess primer), and wherein the melting temperature of the at least one probe-amplification sequence hybrid measured at a concentration of Y μM is at least 5° C. below the melting temperature of the limiting primer ($T_m^L$), wherein $T_m^L = \Delta H/(\Delta S + R \ln(X*10^{-6}/2)) - 273.15 + 12 \log 0.07$, where R is the universal gas constant, and where $\Delta H$ is enthalpy and $\Delta S$ is entropy.

20. The kit according to claim 19 wherein the difference between $T_m^L$ and the melting temperature of the excess primer ($T_m^X$), wherein $T_m^X = \Delta H/(\Delta S + R \ln(10^{-6}/2)) - 273.15 + 12 \log 0.07$, is equal to or higher than 0° C. and, if the limiting primer is not fully complementary to the amplification target sequence, the melting temperature of the imperfect hybrid between the limiting primer and the amplification target sequence ($T_m^{LA}$), wherein $T_m^{LA} = \Delta H/(\Delta S + R \ln(X*10^{-6}/2)) - 273.15 + 12 \log 0.07$, is not more than 5° C. below the melting temperature of the excess primer.

21. The kit according to claim 20, wherein the melting temperature of the limiting primer exceeds the melting temperature of the excess primer is at least 3° C.

22. The kit according to claim 21, wherein: X is not more than 0.05.

23. The kit according to claim 20, wherein the melting temperature of the amplification sequence exceeds the melting temperature of the excess primer by not more than 18° C.

24. The kit according to claim 23, wherein the melting temperature of the at least one probe-amplification sequence hybrid is at least 10° C. below the melting temperature of the limiting primer.

25. The kit according to claim 20, wherein said at least one probe comprises a first hybridization probe specific for a first allele and a second hybridization probe specific for a second allele.

26. The kit according to claim 20, wherein the melting temperature of the at least one probe-amplification sequence hybrid is at least 10° C. below the melting temperature of the limiting primer.

27. The kit according to claim 19, wherein said at least one probe comprises a first hybridization probe specific for a first allele and a second hybridization probe specific for a second allele.

28. The kit according to claim 19, wherein said at least one hybridization probe is a DNA probe.

29. The kit according to claim 28, wherein the melting temperature of the at least one probe-amplification sequence hybrid is at least 10° C. below the melting temperature of the limiting primer.

30. A kit of reagents for performing a homogenous polymerase chain reaction (PCR) assay for at least one pre-selected DNA amplification target sequence comprising a thermostable DNA polymerase, dNTP's and, for each amplification target sequence, an oligonucleotide set according to claim 18.

* * * * *

SEQUENCE LISTING

<160> NUMBER OF SEQ ID NOS: 24

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
ccttctctct gccccctggt                                                    20

<210> SEQ ID NO 2
<211> LENGTH: 22
<212> TYPE: DNA
<213> ORGANISM: Artificial Sequence
<220> FEATURE:
<223> OTHER INFORMATION: primer

<400> SEQUENCE: 2
gccaggggtt ccactacgta ga                                                 22

<210> SEQ ID NO 3
<211> LENGTH: 22
<212> TYPE: DNA
<213> ORGANISM: Artificial Sequence
<220> FEATURE:
<223> OTHER INFORMATION: primer

<400> SEQUENCE: 3
gcccttctct ctgccccctg gt                                                 22

<210> SEQ ID NO 4
<211> LENGTH: 18
<212> TYPE: DNA
<213> ORGANISM: Artificial Sequence
<220> FEATURE:
<223> OTHER INFORMATION: primer

<400> SEQUENCE: 4
gattatgcct ggcaccat                                                      18

<210> SEQ ID NO 5
<211> LENGTH: 23
<212> TYPE: DNA
<213> ORGANISM: Artificial Sequence
<220> FEATURE:
<223> OTHER INFORMATION: primer

<400> SEQUENCE: 5
ctttgatgac gcttctgtat cta                                                23

<210> SEQ ID NO 6
<211> LENGTH: 19
<212> TYPE: DNA
<213> ORGANISM: Artificial Sequence
<220> FEATURE:
<223> OTHER INFORMATION: primer

<400> SEQUENCE: 6
ggattatgcc tggcaccat                                                     19

```
<210> SEQ ID NO 7
<211> LENGTH: 22
<212> TYPE: DNA
<213> ORGANISM: Artificial Sequence
<220> FEATURE:
<223> OTHER INFORMATION: primer

<400> SEQUENCE: 7
cctggattat gcctggcacc at                                              22

<210> SEQ ID NO 8
<211> LENGTH: 24
<212> TYPE: DNA
<213> ORGANISM: Artificial Sequence
<220> FEATURE:
<223> OTHER INFORMATION: primer

<400> SEQUENCE: 8
ccgcccttct ctctgccccc tggt                                            24

<210> SEQ ID NO 9
<211> LENGTH: 34
<212> TYPE: DNA
<213> ORGANISM: Artificial Sequence
<220> FEATURE:
<223> OTHER INFORMATION: probe

<400> SEQUENCE: 9
cgcgcttatc atctttggtg tttcctatag cgcg                                 34

<210> SEQ ID NO 10
<211> LENGTH: 19
<212> TYPE: DNA
<213> ORGANISM: Artificial Sequence
<220> FEATURE:
<223> OTHER INFORMATION: primer

<400> SEQUENCE: 10
tgattatgcc tggcaccat                                                  19

<210> SEQ ID NO 11
<211> LENGTH: 21
<212> TYPE: DNA
<213> ORGANISM: Artificial Sequence
<220> FEATURE:
<223> OTHER INFORMATION: primer

<400> SEQUENCE: 11
cttgattatg cctggcacca t                                               21

<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
tggattatgc ctggcaccat                                                 20

<210> SEQ ID NO 13
<211> LENGTH: 21
<212> TYPE: DNA
<213> ORGANISM: Artificial Sequence
<220> FEATURE:
<223> OTHER INFORMATION: primer
```

<400> SEQUENCE: 13
ctggattatg cctggcacca t                                         21

<210> SEQ ID NO 14
<211> LENGTH: 23
<212> TYPE: DNA
<213> ORGANISM: Artificial Sequence
<220> FEATURE:
<223> OTHER INFORMATION: primer

<400> SEQUENCE: 14
tcctggatta tgcctggcac cat                                       23

<210> SEQ ID NO 15
<211> LENGTH: 29
<212> TYPE: DNA
<213> ORGANISM: Artificial Sequence
<220> FEATURE:
<223> OTHER INFORMATION: primer

<400> SEQUENCE: 15
cagttttcct ggattatgcc tggcaccat                                 29

<210> SEQ ID NO 16
<211> LENGTH: 30
<212> TYPE: DNA
<213> ORGANISM: Artificial Sequence
<220> FEATURE:
<223> OTHER INFORMATION: primer

<400> SEQUENCE: 16
tcagttttcc tggattatgc ctggcaccat                                30

<210> SEQ ID NO 17
<211> LENGTH: 16
<212> TYPE: DNA
<213> ORGANISM: Artificial Sequence
<220> FEATURE:
<223> OTHER INFORMATION: primer

<400> SEQUENCE: 17
gacgcttctg tatcta                                               16

<210> SEQ ID NO 18
<211> LENGTH: 17
<212> TYPE: DNA
<213> ORGANISM: Artificial Sequence
<220> FEATURE:
<223> OTHER INFORMATION: primer

<400> SEQUENCE: 18
tgacgcttct gtatcta                                              17

<210> SEQ ID NO 19
<211> LENGTH: 18
<212> TYPE: DNA
<213> ORGANISM: Artificial Sequence
<220> FEATURE:
<223> OTHER INFORMATION: primer

<400> SEQUENCE: 19
atgacgcttc tgtatcta                                             18

```
<210> SEQ ID NO 20
<211> LENGTH: 20
<212> TYPE: DNA
<213> ORGANISM: Artificial Sequence
<220> FEATURE:
<223> OTHER INFORMATION: primer

<400> SEQUENCE: 20
tgatgacgct tctgtatcta                                              20

<210> SEQ ID NO 21
<211> LENGTH: 24
<212> TYPE: DNA
<213> ORGANISM: Artificial Sequence
<220> FEATURE:
<223> OTHER INFORMATION: primer

<400> SEQUENCE: 21
gctttgatga cgcttctgta tcta                                         24

<210> SEQ ID NO 22
<211> LENGTH: 29
<212> TYPE: DNA
<213> ORGANISM: Artificial Sequence
<220> FEATURE:
<223> OTHER INFORMATION: primer

<400> SEQUENCE: 22
ggcatgcttt gatgacgctt ctgtatcta                                    29

<210> SEQ ID NO 23
<211> LENGTH: 34
<212> TYPE: DNA
<213> ORGANISM: Artificial Sequence
<220> FEATURE:
<223> OTHER INFORMATION: probe

<400> SEQUENCE: 23
cgcgctaaaa tatcattggt gtttcctaag cgcg                              34

<210> SEQ ID NO 24
<211> LENGTH: 23
<212> TYPE: DNA
<213> ORGANISM: Artificial Sequence
<220> FEATURE:
<223> OTHER INFORMATION: primer

<400> SEQUENCE: 24
ccttgatgac gcttctgtat cta                                          23
```